US012195801B2

(12) United States Patent
Abdueva

(10) Patent No.: US 12,195,801 B2
(45) Date of Patent: Jan. 14, 2025

(54) METHODS FOR CHARACTERIZING CELL-FREE NUCLEIC ACID FRAGMENTS

(71) Applicant: Aqtual, Inc., Hayward, CA (US)

(72) Inventor: Diana Abdueva, Orinda, CA (US)

(73) Assignee: Aqtual, Inc., Hayward, CA (US)

( * ) Notice: Subject to any disclaimer, the term of this patent is extended or adjusted under 35 U.S.C. 154(b) by 0 days.

(21) Appl. No.: 18/419,411

(22) Filed: Jan. 22, 2024

(65) Prior Publication Data

US 2024/0158858 A1 May 16, 2024

Related U.S. Application Data

(63) Continuation of application No. 18/336,901, filed on Jun. 16, 2023, now Pat. No. 11,993,818, which is a continuation of application No. 18/056,951, filed on Nov. 18, 2022, which is a continuation of application No. PCT/US2021/033508, filed on May 20, 2021.

(60) Provisional application No. 63/029,328, filed on May 22, 2020.

(51) Int. Cl.
C12Q 1/6883 (2018.01)
C12Q 1/6869 (2018.01)

(52) U.S. Cl.
CPC ......... *C12Q 1/6883* (2013.01); *C12Q 1/6869* (2013.01); *C12Q 2600/158* (2013.01)

(58) Field of Classification Search
CPC ............... C12Q 1/6883; C12Q 1/6869; C12Q 2600/158
See application file for complete search history.

(56) References Cited

U.S. PATENT DOCUMENTS

| | | | |
|---|---|---|---|
| 2014/0349859 A1 | 11/2014 | Oliphant et al. | |
| 2014/0371078 A1 | 12/2014 | Abdueva | |
| 2016/0224730 A1 | 8/2016 | Yu et al. | |
| 2019/0024127 A1* | 1/2019 | Yeh | C40B 40/06 |
| 2019/0287654 A1* | 9/2019 | Curtis | C12Q 1/6886 |
| 2019/0330684 A1* | 10/2019 | Fina | C12Q 1/6806 |
| 2019/0371429 A1 | 12/2019 | Azab et al. | |
| 2019/0390253 A1 | 12/2019 | Kennedy et al. | |
| 2021/0009990 A1 | 1/2021 | Stray et al. | |
| 2023/0287500 A1 | 9/2023 | Abdueva | |
| 2023/0383355 A1 | 11/2023 | Abdueva | |

FOREIGN PATENT DOCUMENTS

| | | | | |
|---|---|---|---|---|
| EP | 2426217 | A1 | 3/2012 | |
| EP | 4154255 | | 3/2023 | |
| GB | 2552461 | A | 1/2018 | |
| WO | WO-2014130890 | A1 | 8/2014 | |
| WO | WO-2016015058 | A2 * | 1/2016 | .......... C12Q 1/6869 |
| WO | WO-2016067029 | A1 * | 5/2016 | ......... C12N 15/1003 |
| WO | WO-2016189388 | A1 | 12/2016 | |
| WO | WO-2018009723 | A1 | 1/2018 | |
| WO | WO-2018064629 | A1 | 4/2018 | |
| WO | WO-2018094031 | A1 * | 5/2018 | .......... C12Q 1/6806 |
| WO | WO-2018140452 | A1 * | 8/2018 | ............. C12N 15/10 |
| WO | WO-2018170511 | A1 | 9/2018 | |
| WO | WO-2018227202 | A1 * | 12/2018 | .......... C12Q 1/6869 |
| WO | WO-2019110750 | A1 * | 6/2019 | .......... C12Q 1/6806 |
| WO | WO-2019170773 | A1 | 9/2019 | |
| WO | WO-2021236993 | | 11/2021 | |

OTHER PUBLICATIONS

Underhill et al. PLoS Genetics. 2016. 12(7):e1006162, 24 pages. (Year: 2016).*
Diaz et al. Journal of Clinical Oncology. 2014. 32(6):579-586. (Year: 2014).*
Albert, et al. Direct selection of human genomic loci by microarray hybridization. Nat Methods. Nov. 2007;4(11):903-5. Epub Oct. 14, 2007.
Co-pending U.S. Appl. No. 18/419,406, inventor Abdueva; Diana, filed Jan. 22, 2024.
Ferenczy et al., Diagnostic performance of Hybrid Capture human papillomavirus deoxyribonucleic acid assay combined with liquid-based cytologic study. Am J Obstet Gynecol. Sep. 1996;175(3 Pt 1):651-6. doi: 10.1053/ob.1996.v175.a73868.
Filiatrault, et al., Transcriptome analysis of Pseudomonas syringae identifies new genes, noncoding RNAs, and antisense activity, Journal of bacteriology, Feb. 15, 2010 vol. 192, No. 9, pp. 2359-2372.
Gnirke et al., Solution hybrid selection with ultra-long oligonucleotides for massively parallel targeted sequencing. Nat Biotechnol. Feb. 2009;27(2):182-9. doi: 10.1038/nbt.1523. Epub Feb. 1, 2009.
Hummel et al., Cell-free DNA release under psychosocial and physical stress conditions. Translational Psychiatry vol. 8, Article No. 236 (2018).
Kanamori-Katayama et al., Unamplified cap analysis of gene expression on a single-molecule sequencer. Genome Res. Jul. 2011;21(7):1150-9. doi: 10.1101/gr.115469.110. Epub May 19, 2011.
Katevatis, Constantinos, et al. Low Concentration DNA Extraction and Recovery Using a Silica Solid Phase. PLOS One, vol. 12, No. 5 (2017): p. e0176848.
Kozarewa et al., Overview of Target Enrichment Strategies. Curr Protoc Mol Biol. Oct. 1, 2015;112:7.21.1-7.21.23.
Lesnik and Freier et al., Relative Thermodynamic Stability of DNA, RNA, and DNA:RNA Hybrid Duplexes: Relationship with Base Composition and Structure. Biochemistry 1995, 34, 34, 10807-10815.

(Continued)

*Primary Examiner* — Joseph G. Dauner
(74) *Attorney, Agent, or Firm* — WILSON SONSINI GOODRICH & ROSATI

(57) ABSTRACT

The present disclosure provides methods and systems for various uses of cell-free nucleic acid (cfNA). Functional typing of cfNA fragmentation patterns may be utilized in the non-invasive detection, diagnosis, and monitoring of disease. One embodiment may determine a stage of cancer in a subject, the progression of cancer in a subject, or the responsiveness to treatment of a cancer in a subject. Another embodiment disclosed herein may include sequencing-free diagnostic methods.

21 Claims, 38 Drawing Sheets

(56) References Cited

OTHER PUBLICATIONS

Liu, et al., Enrichment of short mutant cell-free DNA fragments enhanced detection of pancreatic cancer. EbioMedicine, 2019,41: 345-356.
Liu, L. et al. Size-selective separation of DNA fragments by using lysine-functionalized silica particles. Sci Rep 6, 22029 (2016). https://doi.org/10.1038/srep22029.
Liu, L., et al. Supplementary Information: Size-selective separation of DNA fragments by using lysine-functionalized silica particles. Sci Rep 6, 22029 (2016). https://doi.org/10.1038/srep22029.
Noguchi et al., FANTOM5 CAGE profiles of human and mouse samples. Sci Data. 2017; 4: 170112.
Oreskovic, et al., Ultrasensitive hybridization capture: Reliable detection of 1 copy/mL short cell-free DNA from large-volume urine samples. PLoS One. Feb. 26, 2021;16(2):e0247851. doi: 10.1371/journal.pone.0247851. eCollection 2021.
PCT/US2021/033508 International Search Report and Written Opinion dated Sep. 30, 2021.
Raymond, et al., Ultraprep is a scalable, cost-effective, effective-bead-based method for purifying cell-free DNA. PLoS One, 2020, 15(6): e0231854, 11 Pages.
Sadeh et al., ChIP-seq of plasma cell-free nucleosomes identifies gene expression programs of the cells-of-origin. Nat Biotechnol. May 2021;39(5):586-598. doi: 10.1038/s41587-020-00775-6. Epub Jan. 11, 2021.
Ulz et al., Inferring expressed genes by whole-genome sequencing of plasma DNA. Nat Genet. Oct. 2016;48(10):1273-8. doi: 10.1038/ng.3648. Epub Aug. 29, 2016.
U.S. Appl. No. 18/336,901 Notice of Allowance dated Jan. 23, 2024.
U.S. Appl. No. 18/336,901 Office Action dated Oct. 4, 2023.
Vandeventer, Peter et al. DNA Adsorption to and Elution from Silica Surfaces: Influence of Amino Acid Buffers. The journal of physical chemistry. B vol. 117, 37 (2013): 10742-10749.
Warnmark et al., Activation functions 1 and 2 of nuclear receptors: molecular strategies for transcriptional activation. Mol Endocrinol . Oct. 2003;17(10):1901-9. doi: 10.1210/me.2002-0384. Epub Jul. 31, 2003.
Xiao, et al., Performance of probe polymerization-conjunction-agarose gel electrophoresis in the rapid detection of KRAS gene mutation. Genetics and Molecular Biology, 2018, 41(3): 555-561.
Zhang, B. et al., High-resolution DNA size enrichment using a magnetic nano-platform and application in non-invasive prenatal testing†, Analyst, 2020, 145, 5733-5739.
European Patent Application 21808790.6 Extended European Search Report dated Jun. 17, 2024.
Chan, Rebecca WY. et al. Plasma DNA Aberrations in Systemic Lupus Erythematosus Revealed by Genomic and Methylomic Sequencing. Proceedings of the National Academy of Sciences 111(49):E5302-E5311 (2014).
U.S. Appl. No. 18/056,951 Office Action dated Sep. 10, 2024.
U.S. Appl. No. 18/419,406 Corrected Notice of Allowability dated Aug. 23, 2024.

* cited by examiner

METHODS FOR CHARACTERIZING CELL-FREE NUCLEIC ACID FRAGMENTS

CROSS-REFERENCE

The present application is a continuation of U.S. Non-Provisional application Ser. No. 18/336,901, filed on Jun. 16, 2023, which is a continuation application of U.S. Non-Provisional application Ser. No. 18/056,951, filed on Nov. 18, 2022, which is a continuation application of International Application No. PCT/US2021/033508, filed on May 20, 2021, which claims the benefit of priority to U.S. Provisional Application No. 63/029,328 filed May 22, 2020, which is incorporated herein by reference.

BACKGROUND

Cell-free nucleic acid (cfNA) may comprise cell-free deoxyribonucleic acid (cfDNA), cell-free ribonucleic acid (cfRNA) or some combination thereof and is present in circulating plasma, urine, and other bodily fluids of humans. cfDNA comprises both single and double-stranded DNA fragments that may be at a low concentration in the circulating plasma of healthy individuals. However, cfDNA levels may be increased in patients with chronic and acute pathologies and may provide a non-invasive method to quantify or observe tissue damage, cell death, or cell turnover. cfDNA derived from tumors may be useful in the non-invasive detection of tumor presence, type, or location and may allow for the early detection of tumors or other malignancies. cfDNA of fetal origin has been observed in maternal circulation and may be used as a non-invasive method of prenatal screening. Donor-derived cfDNA has also been detected in the circulating fluids of transplant recipients and may be a biomarker for acute rejection in these populations. Given the risks associated with invasive diagnostic procedures in treating broad pathologies, it may be important to use non-invasive cfDNA-based diagnostics.

SUMMARY

In some aspects, the present disclosure provides a method of characterizing cell-free nucleic acid (cfNA) fragments derived from a genomic region, comprising: contacting a composition comprising cfNA with an oligonucleotide bait comprising a sequence complementary to a sequence of the genomic region, and characterizing a fragmentation pattern of the cfNA fragments that hybridize to the oligonucleotide bait, wherein characterizing the fragmentation pattern does not comprise identifying genomic locations or lengths of the cfNA fragments. In some embodiments, characterizing the fragmentation pattern of the cfNA fragments comprises analyzing abundance of the cfNA fragments that hybridize to the oligonucleotide bait. In some embodiments, the characterizing a fragmentation pattern of the cfNA fragments comprises analyzing sizes of the cfNA fragments that hybridize to the oligonucleotide bait. In some embodiments, characterizing a fragmentation pattern of the cfNA fragments comprises calculating a transcriptional activity score (TAS). In some embodiments, the analyzing sizes of the cfNA fragments comprises performing an electrophoretic separation. In some embodiments, the electrophoretic separation comprises gel or capillary electrophoresis. In some embodiments, the electrophoretic separation comprises microfluidic separation of cfNA fragments. In some embodiments, the analyzing sizes of the cfNA fragments comprises comparing mobilities of the cfNA fragments to a known standard. In some embodiments, calculating a TAS comprises determining a fraction of total cfNA having lengths of at least 230, 255, 270, 285 or 310 nucleotides. In some embodiments, calculating a TAS comprises determining a fraction of total cfNA having lengths of 230-600 nucleotides. In some embodiments, calculating a TAS comprises determining a fraction of total cfNA that is protected by a DNA polymerase or transcription factor. In some embodiments, an increased TAS is indicative of a medical condition. In some embodiments, an increase or decrease in TAS is indicative of a medical condition.

In some embodiments, the characterizing cfNA fragments comprises: i) sequencing cfNA fragments that hybridize to the oligonucleotide bait, and ii) performing an alignment-free sequence comparison of the cfNA fragment nucleotide sequences to a reference sequence; wherein the genomic region comprises the reference sequence. In some embodiments, the method further comprises quantifying a relative amount of cfNA fragment sequences aligning to sequences distal to a first end of the oligonucleotide bait versus cfNA fragment sequences aligning to sequences distal to a second end of the oligonucleotide bait. In some embodiments, the characterizing a fragmentation pattern of the cfNA fragments comprises: a) sequencing cfNA fragments that hybridize to the oligonucleotide bait, b) identifying two or more subregions within the genomic region, and c) counting a number of cfNA fragments comprising a sequence matching each subregion, wherein the oligonucleotide bait comprises a sequence complementary to a sequence of the genomic region. In some embodiments, a cfNA fragment matches a subregion if a sequence of the cfNA fragment has no more than one mismatch over 40 contiguous bases to a sequence of the subregion.

In some embodiments, the method comprises a) contacting the composition with the oligonucleotide bait and a second oligonucleotide bait, b) analyzing the cfNA fragments that hybridize to the oligonucleotide bait, and c) analyzing the cfNA fragments that hybridize to the second oligonucleotide bait, wherein the oligonucleotide bait and the second oligonucleotide bait comprise sequences complementary to sequences of the genomic region. In some embodiments, the method further comprises comparing the cfNA fragments that hybridize to the oligonucleotide bait with cfNA fragments that hybridize to the second oligonucleotide bait. In some embodiments, the analyzing the cfNA fragments that hybridize to the oligonucleotide bait and the second oligonucleotide bait comprises measuring an amount of cfNA fragments that hybridize to the oligonucleotide bait and an amount of cfNA fragments that hybridize to the second oligonucleotide bait. In some embodiments, the analyzing the cfNA fragments that hybridize to the oligonucleotide bait and the second oligonucleotide bait comprises analyzing sizes of the cfNA fragments. In some embodiments, the method further comprises a) quantifying a relative amount of cfNA fragment sequences aligning to sequences distal to a first end of the oligonucleotide bait versus cfNA fragment sequences aligning to sequences distal to a second end of the oligonucleotide bait, b) quantifying a relative amount of cfNA fragment sequences aligning to sequences distal to a first end of the second oligonucleotide bait versus cfNA fragment sequences aligning to sequences distal to a second end of the second oligonucleotide bait. In some embodiments, the method further comprises quantifying a relative amount of cfNA fragment sequences aligning to sequences distal to an end of the oligonucleotide bait versus cfNA fragment sequences aligning to sequences distal to a second end of the first oligonucleotide bait.

In some aspects, the present disclosure provides a method of characterizing cfNA fragments comprising a sequence of a genomic region, comprising comparing an amount of the cfNA fragments from a composition comprising cfNA that comprise a first portion of the genomic region with an amount of the cfNA fragments that comprise a second portion of the genomic region. In some embodiments, the amounts of cfNA fragments that comprise the first portion and the second portion of the genomic region are determined by a method comprising amplification of the portions of the genomic region. In some embodiments, the amplification is performed by PCR, loop mediated isothermal amplification, nucleic acid sequence-based amplification, strand displacement amplification, or multiple displacement amplification.

In some aspects, the present disclosure provides a method of characterizing cfNA fragments comprising a sequence of a genomic region, comprising sequencing the cfNA fragments and comparing an amount of cfNA fragment sequences matching a first set of reference sequences representing a first fragmentation pattern to an amount of cfNA fragment sequences matching a second set of reference sequences representing a second fragmentation pattern. In some embodiments, the cfNA fragment sequences matching the first and second sets of reference sequences are identified by an alignment-free sequence comparison.

In some aspects, the present disclosure provides a method of analyzing a cfNA fragmentation pattern comprising characterizing cfNA fragments comprising a sequence of two or more genomic regions according to the methods disclosed herein. In some embodiments, the oligonucleotide bait is conjugated to an affinity tag. In some embodiments, the affinity tag is biotin. In some embodiments, the oligonucleotide bait is conjugated to a solid surface. In some embodiments, the solid surface is a bead. In some embodiments, the solid surface is a planar surface. In some embodiments, the cfNA fragments are cell-free deoxyribonucleic acid (cfDNA) fragments. In some embodiments, the cfNA fragments are cell-free ribonucleic acid (cfRNA) fragments. In some embodiments, the composition comprising cfNA is plasma, serum, saliva, urine, blood components, cerebrospinal fluid, pleural fluid, amniotic fluid, peritoneal fluid, ascitic fluid, abdominopelvic washings/lavage, serous effusions, tracheobronchial or bronchoalveolar lavage. In some embodiments, the composition comprising cfNA is plasma. In some embodiments, the genomic region comprises at least one nucleotide of a promotor, a transcriptional start site, a DNase I-hypersensitive site, a Pol II pausing site, a first exon, or an intron to exon boundary. In some embodiments, the genomic region comprises a first exon. In some embodiments, the genomic region comprises an active transcriptional start site.In some embodiments, the genomic region comprises a start site or first exon of a steroid responsive gene. In some embodiments, steroid responsive gene is a glucocorticoid responsive gene, an anti-inflammatory gene, or a neutrophil activation signature gene. In some embodiments, the steroid responsive gene is DUSPI or SAE1. In some embodiments, the genomic region comprises a start site or first exon of a vascular marker gene. In some embodiments, the endothelial cell marker gene is VWF or EPHB4. In some embodiments, the genomic region is selected from first 5 exons of EPHB4.

In some aspects, the present disclosure provides a method of evaluating a medical condition in a subject comprising characterizing a fragmentation pattern of cfNA fragments comprising a sequence of a genomic region according to any one of the methods disclosed herein.

In some aspects, the present disclosure provides a method of adaptive immunotherapy for the treatment of cancer in a subject comprising: a) administering a first course of a first immunotherapy compound to the subject; b) acquiring a longitudinal cell-free DNA fragmentation profile for one or more genes associated with angiogenesis and/or vasculogenesis from the subject; and c) administering a second course of immunotherapy to the subject; wherein the second course of immunotherapy comprises: i. a second immunotherapy compound if the cell-free DNA fragmentation profile is indicative of an insufficient response to the first immunotherapy compound; or ii. a second course of the first immunotherapy compound if the cell-free DNA fragmentation profile is not indicative of an insufficient response to the first immunotherapy compound.

In some aspects, the present disclosure provides a method of treating a medical condition in a subject comprising: administering a course of therapy to the subject, and acquiring a longitudinal cell-free DNA fragmentation profile of one or more genomic regions from the subject; wherein the a longitudinal cell-free DNA fragmentation profile indicates that the subject has responded to the course of therapy.

In some aspects, the present disclosure provides a method of treating a medical condition in a subject comprising: acquiring a cell-free DNA fragmentation profile of one or more genomic regions from the subject; and administering a course of therapy to the subject, wherein the cell-free DNA fragmentation profile indicates that the course of therapy is indicated for the subject.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
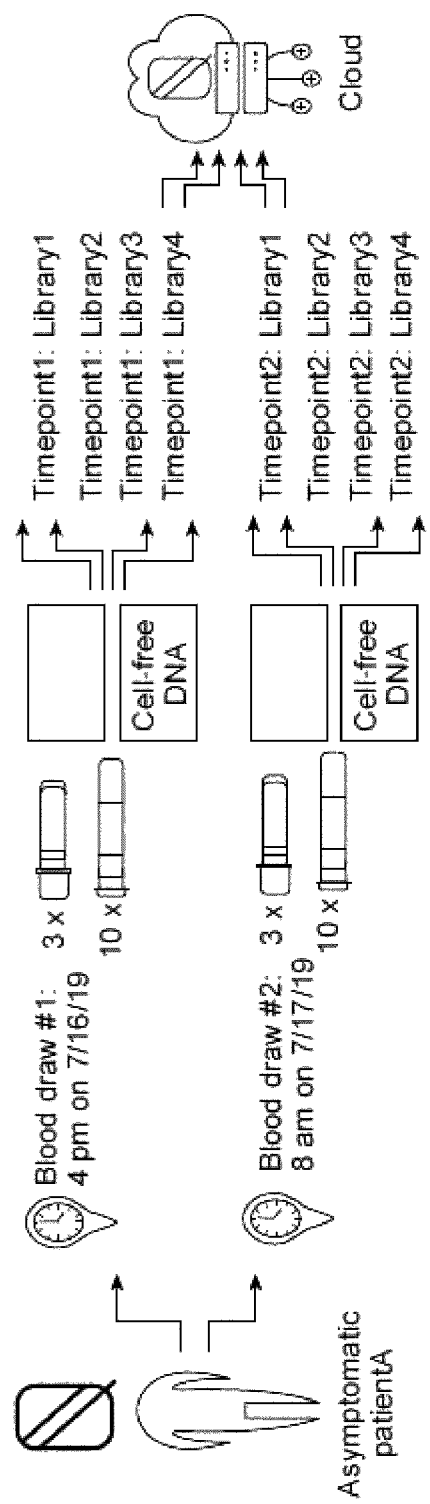
FIG. 1 illustrates a schematic wherein a female subject received a single daily dose of 40 mg prednisolone, an effective anti-inflammatory drug used extensively to treat many diseases, after administering a blood draw. A second blood draw was performed 16 hours later.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the term "nucleic acid," generally refers to a polymeric form of nucleotides of any length (e.g., at least 2, 3, 4, 5, 6, 7, 8, 9, 10, 100, 500, 1000 or more nucleotides), either deoxyribonucleotides or ribonucleotides, or analogs thereof. A nucleic acid may include one or more subunits selected from adenosine (A), cytosine (C), guanine (G), thymine (TO, and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that is specific to one of more complementary A, C, G, T, or U, or complementary to a purine (e.g., A or G, or variant thereof) or pyrimidine (e.g., C, T, or U, or variant thereof). In some examples, a nucleic acid may be single-stranded or double stranded, in some cases, a nucleic acid molecule is circular. Non-limiting examples of nucleic acids include deoxyribonucleic acid (DNA) and ribonucleic acid (RNA). Nucleic acids can include coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid molecule may comprise one or more modified nucleotides, such as methylated nucleotides and nucleotide analogs.

As used herein, the terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be the to be "expressed" by the cell. An expression product can be characterized as intracellular, extracellular or transmembrane. The term "intracellular" means something that is inside a cell. The term "extracellular" means something that is outside a cell. The term transmembrane means something that has an extracellular domain outside the cell, a portion embedded in the cell membrane and an intracellular domain inside the cell.

The term "sample", "biological sample", or "patient sample" as used herein, generally refers to any sample containing or suspected of containing a nucleic acid molecule. For example, a sample can be a biological sample containing one or more nucleic acid molecules. The biological sample can be obtained (e.g., extracted or isolated) from or include blood (e.g., whole blood), plasma, serum, umbilical cord blood, chorionic villi, amniotic fluid, lavage fluid (e.g., bronchoalveolar, gastric, peritoneal, ductal, ear, arthroscopic), biopsy sample (e.g., from pre-implantation embryo), celocentesis sample, fetal nucleated cells or fetal cellular remnants, bile, breast milk, urine, saliva, mucosal excretions, sputum, stool, sweat, vaginal fluid, fluid from a hydrocele (e.g., of the testis), vaginal flushing fluids, pleural fluid, ascitic fluid, cerebrospinal fluid, bronchoalveolar lavage fluid, discharge fluid from the nipple, aspiration fluid from different parts of the body (e.g., thyroid, breast), tears, embryonic cells, or fetal cells (e.g., placental cells). In some embodiments, a blood sample is obtained by a heel or finger prick, from scalp veins, or by ear lobe puncture. The biological sample can be a fluid or tissue sample (e.g., skin sample). The biological sample can include any tissue or material derived from a living or dead subject. A biological sample can be a cell-free sample. A biological sample can comprise a nucleic acid (e.g., DNA or RNA) or a fragment thereof.

The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). In some examples, the sample is obtained from a cell-free bodily fluid, such as whole blood. In such instance, the sample may include cell-free DNA and/or cell-free RNA. In some examples, the majority of DNA in a biological sample that may be enriched for cfDNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis. In some examples, the sample can include circulating tumor cells or circulating fetal cells.

The term "whole blood sample", as used herein, generally refers to a whole blood sample that has not been fractionated or separated into its component parts. Whole blood may be combined with an anticoagulant such as EDTA or ACD during the collection process but is generally otherwise unprocessed. "Whole Blood" may refer to a specific standardized product for transfusion or further processing, or to any unmodified collected blood.

The term "blood fractionation", as used herein, generally refers to the process of fractionating whole blood or separating it into its component parts. This may be done by centrifuging the blood. The resulting components may be a clear solution of blood plasma in the upper phase (which can be separated into its own fractions), a buffy coat, which is a thin layer of leukocytes (white blood cells) mixed with platelets in the middle, and erythrocytes (red blood cells) at the bottom of a centrifuge tube in the hematocrit faction.

The terms "blood plasma" or "plasma", as used herein, generally refers to the straw-colored/pale-yellow liquid component of blood that normally holds the blood cells in whole blood in suspension. Blood plasma makes up about 55% of total blood by volume. It is the intravascular fluid part of [extracellular fluid] (all body fluid outside of cells). It is mostly water (93% by volume), and contains dissolved proteins including albumins, immunoglobulins, and fibrinogen, glucose, clotting factors, electrolytes ($Na^+$, $Ca^{2+}$, $Mg^{2+}$, $HCO_3^-Cl^-$ etc.), hormones and carbon dioxide. Blood serum is blood plasma without fibrinogen or the other clotting factors (i.e., whole blood minus both the cells and the clotting factors).

As used herein, the term "cell-free deoxyribonucleic acid" (cfDNA), as used herein, generally refers to non-encapsulated DNA in bodily fluids, particularly blood. cfDNA are nucleic acid fragments that may enter the bloodstream during necrosis or apoptosis. Fragments of non-encapsulated DNA may be engulfed by macrophages or other immune cells. cfDNA fragments average around 170 base pairs in length and may be present in both early and late stage disease. cfDNA may be of fetal origin circulating in a pregnant mother, derived from recipient tissues in donated organs or cells, or may be released from malignancies. cfDNA may be utilized as a biomarker for the presence or progression of any pathology.

The term "liquid biopsy," as used herein, generally refers to a non-invasive or minimally invasive laboratory test or assay (e.g., of a biological sample or cell-free DNA). In some instances, a liquid biopsy is performed on a plasma or serum sample obtained by a simple needle stick. Blood can be drawn at any time during the course of therapy and allow for dynamic monitoring of molecular changes rather than relying on a static time point. Such "liquid biopsy" assays may report measurements (e.g., minor allele frequencies, gene expression, or protein expression) of one or more pathology associated marker genes.

The term "fragment" (e.g., a cfDNA fragment), as used herein, can refer to a portion of a polynucleotide or polypeptide sequence that comprises at least 3 contiguous nucleotides. A nucleic acid fragment can retain the biological activity and/or some characteristics of the parent polynucleotide. cfDNA may be shed as a fragment with different genetic and epigenetic profiles and in various lengths. A fragment may be a short (small) fragment or a long (large) fragment and the size patterns of fragments, such as cfDNA fragments, may vary in pathological conditions.

The term "fragmentation pattern", as used herein, generally refers to a collection of fragments, such as cfDNA fragments, present in a subject. The composition of a fragmentation pattern may depend upon a tissue of origin, pathological state, or progression of a disease.

As used herein, the terms "genomic region", "genomic position", "genomic site", or "genomic location" generally refer to a physical location on a genome or chromosome, which may be associated with a gene or a set of genes, or a portion of a nucleic acid polymer (e.g., a chromosome) that is contained within the human genome complement. The term can relate to a specific length of DNA. The location of a genome can be defined with respect to either a chromosomal band in the human genome or one or more specific nucleotide positions in the human genome.

The terms "size profile" and "size distribution", as used herein, generally relate to the sizes of DNA fragments in a biological sample. A size profile can be a histogram that provides a distribution of an amount of DNA fragments at a variety of sizes. Various statistical parameters (also referred to as size parameters or just parameter) can distinguish one size profile from another. One parameter can be the percentage of DNA fragment of a size or range of sizes relative to all DNA fragments or relative to DNA fragments of another size or range. A "size profile" or "size distribution" may represent the size of cfDNA fragments derived from a specific locus or specified loci of the genome.

As used herein, the term "exome" generally refers to the subset of the genome composed of exons, the sequences which, when transcribed, remain within the mature RNA after introns are removed by RNA splicing and contribute to the final protein product encoded by that gene.

As used herein, the term "nucleosome" generally refers to a section of DNA that is wrapped around a core of proteins responsible in part for the compactness of a chromosome. In the nucleus, DNA forms a complex with proteins called chromatin which allows the DNA to be condensed into a smaller volume. A nucleosome is the fundamental subunit of chromatin. A nucleosome is composed of approximately two turns of DNA wrapped around a set of eight core histones.

The term "oligonucleotide", as used herein, generally refers to a nucleic acid molecule comprising at least one nucleotide that may have various lengths such as either deoxyribonucleotides or ribonucleotides or analogs thereof. An oligonucleotide may comprise at least about 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 400, 500, 600, 700, 800, 900, 1,000, 5,000, 10,000, 50,000, 100,000 or more nucleotides. An oligonucleotide may comprise at most about 100,000, 50,000, 10,000, 5,000, 1,000, 900, 800, 700, 600, 500, 400, 300, 250, 200, 175, 150, 125, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, or less nucleotides. An oligonucleotide may be unbound (e.g., in solution) or bound (e.g., chemically bonded to a substrate). Oligonucleotides may include one or more nonstandard nucleotide(s), nucleotide analog(s), modified nucleotides, or any combination thereof.

The term "bait", as used herein, generally refers to a synthetic oligonucleotide which, when left to hybridize over a period of time, can capture a nucleic acid fragment with a complementary sequence. Baits may be various sizes, may be labeled or unlabeled, and can target multiple overlapping and/or non-overlapping genomic regions. Baits may enable preferential capture of nucleic acid fragments associated with molecular functions of interest.

The term "bait pool", as used herein, generally refers to a collection or panel of baits with a targeted capture profile. A bait pool may represent an optimized combination of bait sequences that target cfNA fragments of interest.

The term "functional typing", as used herein, generally refers to predicting a pathological condition probability based on a comparison between the estimated fractional representation and a predetermined association of one or more distinct components with clinical reference data. Functional typing may be determined through a feature profile for the designed bait pools and estimating the fractional representation of one or more pool components relative to a combination of other components based on a set of regression coefficients.

The term "chromatin", as used herein, generally refers to the nucleoprotein structure that comprises the cellular genome. Cellular chromatin includes nucleic acid, primarily DNA, and protein, including histones and non-histone chromosomal proteins. The majority of the eukaryotic cellular chromatin is in the form of nucleosomes, with one nucleosome core comprising about 150 DNA base pairs associated with an octamer comprising two each of the histones H2A, H2B, H3 and H4. Linker DNA (of variable length depending on the organism) extends between nucleosome nuclei. A histone H1 protein is generally associated with the linker DNA. Cellular chromatin includes both chromosomal and episomal chromatin.

The term "epigenetic", as used herein, generally refers to refers to information encoded "on top of" or "in addition to" the traditional genetic basis for inheritance, i.e. typically does not include modifications to the underlying sequence (genetic code). An epigenetic alteration is a stable alteration in gene expression potential mediated by mechanisms other than alterations in the primary nucleotide sequence of a gene. The epigenome is an aggregate of heritable cellular markers, such as histone modifications or DNA methylation, that may control the differential expression of genes. An epigenetic alteration may be due to environmental conditions causing chemical modifications to these heritable cellular markers. These alterations may be transgenerational. Assessing or determining an epigenetic profile includes detecting changes in the transcriptome and reaction of DNA with bisulfite to modify unmethylated cysteines.

The term "cell death", as used herein, generally refers to an irreversible event in which a cell ceases to carry out its functions. Cell death may occur within a broader physiological context such as in embryonic development or tissue renewal, or it may be a pathologic response to cell injury or infectious pathogens. Apoptosis is a programmed form of cell death in multicellular organisms. Cell death may occur due to autophagy wherein there is sequestration of cytoplasm and organelles in double or multimembrane vesicles and delivery to the cells own lysosomes for subsequent degradation. Cell death may be due to necrosis, a toxic process, where the cell follows an energy independent mode of death and degradative processes that occur after cell death. While apoptosis may be accompanied by cell shrinkage, pyknosis, and karyorrhexis, oncosis is a process induced by energy depletion that leads to necrosis with karyolysis characterized by cell swelling. Cell death may also occur through pyroptosis, an inflammatory programmed cell death triggered by pathologic stimuli or inflammatory host factors which may form an immune response to such pathological conditions.

The term "cellular debris" or "cell debris", as used herein, generally refers to the organic waste left over after a cell dies. Cellular debris may be further processed and catabolized by phagocytes.

The term "hybridization," as used herein, generally refers to the phenomenon in which a single stranded nucleic acid anneals to a nucleic acid with a complementary sequence.

The term "cancer" or "malignancy" as used herein, generally refers to abnormal and unregulated growth of tissue or cells wherein. A mass of tissue (a tumor) or uncontrolled cells can be defined as "benign" or "malignant" depending on the following characteristics: degree of cellular differentiation including morphology and functionality, rate of growth, local invasion and metastasis. A "benign" mass of tissue or cells can be well differentiated, have characteristically slower growth than a malignant mass of tissue or cells and remain localized to the site of origin. In addition, in some cases a benign mass of tissue or cells does not have the capacity to infiltrate, invade or metastasize to distant sites. A "malignant" mass of tissue or cells can be a poorly differentiated (anaplasia), have characteristically rapid growth accompanied by progressive infiltration, invasion, and destruction of the surrounding tissue. Furthermore, a malignant tumor can have the capacity to metastasize to distant sites.

The term "disease progression" or "level of pathology", as used herein, may refer to whether a disease or pathology exists (i.e., a presence or absence), a stage of a disease, the total burden of the body, and/or other measure of a severity of a disease. The level of pathology can be used in various ways. For example, screening can check if a pathology is present in someone who is not known previously to have the pathology. Assessment can investigate someone who has been diagnosed with a pathology to monitor the progress of the condition over time, study the effectiveness of therapies or to determine the prognosis. Detection can comprise 'screening' or can comprise checking if someone, with suggestive features of a pathology (e.g., symptoms or other positive tests), has the pathological condition. A "level of pathology" can refer to level of pathology associated with a pathogen.

The term "cancer progression" or "level of cancer" can refer to whether cancer exists (i.e., presence or absence), a stage of a cancer, a size of tumor, presence or absence of metastasis, the total tumor burden of the body, and/or other measure of a severity of a cancer (e.g., recurrence of cancer). The level of cancer can be a number or other indicia, such as symbols, alphabet letters, and colors. The level can be zero. The level of cancer can also include premalignant or precancerous conditions (states) associated with mutations or several mutations. When the cancer is associated with a pathogen, a level of cancer can be a type of a level of pathology. The prognosis can be expressed as the chance of a patient dying of cancer, or the chance of the cancer progressing after a specific duration or time, or the chance of cancer metastasizing.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The use of the word "a" or "an," when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "about" is used to indicate that a value includes the inherent variation of error for the device, the method being employed to determine the value, or the variation that exists among the study subjects. Unless otherwise specified based upon the above values, the term "about" means ±5% of the listed value.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

The term "sequence context" as used herein refers to the nucleic acid sequence composition (e.g., DNA sequence composition). DNA sequence composition can be used to derive several context metrics that are relevant to underlying transcriptional status of the locus, such as individual base composition, GC percentage, number of CpG sites, number of informative differentially methylated CpGs (iDMCs), number of dinucleotide repeat motifs (DRM), occurrence profiles of known TF motifs, etc.

The term "transcriptional activity score" or "TAS" as used herein refers to a weighted ratio of longer (non-canonical) fragment counts to a total abundance of fragments at a locus. It may also involve different features of a NA fragment length distribution, such as clusters, gaps, peaks, and outliers. Anomalies in observed fragment length distribution may also be summarized using deep learning that finds anomalous length patterns associated with transcription. It may involve learning and training using previously generated data.

We confirmed that distribution of circulating NA fragments length at transcriptionally active loci is indicative of transcriptional activity of live cell prior/during its death. Thus, a transcriptional activity score can be derived based on the distribution and a particular fragment length band and the associated mode of the distribution can be identified as canonical-chromatin organization of the DNA unperturbed by protein binding, while the rest of the bands (or some of the remaining bands) and associated peaks would be labeled as non-canonical and represent NA fragments associated with protein binding, indicative of transcription.

The discovery of circulating DNA and RNA in the plasma of healthy individuals and patients was made by Mandel and Metais in 1948 (Mandel and Metais, 1948) which was furthered in 1966 by Tan et al who observed an anomalous pattern of cell-free deoxyribonucleic acid (cfDNA) in patients who suffered from systemic lupus erythematosus (Tan et al. 1966)-an autoimmune disease in which the major antigen is nucleosomal self-DNA. Despite these early discoveries, the relevance of circulating nucleic acids (CNAs) did not begin to be explored until the 1990s when the presence of tumor-derived oncogenic DNA was observed in the plasma of patients with cancer (Sorenson et al. 1994) and DNA of fetal origin was detected in the maternal circulation (Lo et al. 1997). These findings led to the subsequent understanding that cfDNA levels are increased in patients with chronic and acute pathologies, including autoimmune diseases, stroke and trauma (Butt and Swaminathan 2008, Wagner 2012), suggesting the concentration of cfDNA could serve as a non- invasive blood biomarker to reflect the rate of tissue damage, cellular death and turnover.

Circulating cfDNA are relatively short double-stranded DNA fragments, averaging approximately 170 base pairs, and present in circulating plasma, urine, and other bodily fluids. In the plasma of healthy individuals, cfDNA may be derived primarily from the apoptosis of cells of hematopoietic origin, however other tissues may contribute to the composition of cfDNA in bodily fluids. While cfDNA has been used in specialties such as reproductive medicine, oncology, and transplant medicine, its use as a non-invasive method to screen for, diagnose, determine prognosis, and provide guidance in treatment may be applicable to many other pathologies and conditions.

cfDNA may be analyzed with regard to the representation and distribution of specific sequences and epigenetic features, such as DNA digestion and/or methylation patterns. In addition to pathology-associated genetic variants, analysis of cfDNA may reveal epigenetic footprints and signatures of phagocytic removal of dying cells, which may result from an aggregate nucleosomal occupancy profile of present pathologies as well as their microenvironment components, such as tumor malignancies. cfDNA may be released by various host cells such as neutrophils, macrophages, eosinophils, as well as tumor cells and may accumulate in circulating plasma as a consequence of increased cell death and/or activation, impaired clearance of cfDNA, and/or decreases in levels of endogenous DNase enzymes. cfDNA circulating in a subject's bloodstream may be packed into membrane-coated structures such as apoptotic bodies and may be subsequently analyzed for the effects of these structures on the characteristics of cfDNA fragments.

In a cell nucleus, DNA may exist in nucleosomes, structures comprising a section of DNA approximately 145 base pairs wrapped around a core histone octamer, allowing DNA to be condensed into a smaller volume into a chromatin complex. Electrostatic and hydrogen-bonding interactions of DNA and histone dimers may result in energetically unfavorable bending of DNA over the protein surface. Such bending may be sterically prohibitive to other DNA-binding proteins and may serve to regulate access to DNA in a cell nucleus. Nucleosome positioning in a cell may fluctuate dynamically over time and across various cell states and conditions such as partially unwrapping and rewrapping spontaneously. Since a fragmentation pattern may reflect histone-protected DNA fragments that originated from a configuration influenced by nucleosomal units, nucleosome stability and dynamics may influence such a fragmentation pattern. These nucleosome dynamics may stem from a variety of factors, such as post-translational modifications of histones through processes such as acetylation, methylation, phosphorylation, or ubiquitination, which may influence chromatin structure.

Chromatin organization may differ depending on factors such as global cellular identity, metabolic state, regional regulatory state, local gene activity, cell death, and mechanisms of DNA clearance. All of these factors can influence to the manner in which DNA is fragmented after cell death, and consequently, the fragmentation pattern. However, cfDNA fragmentation patterns may be only partially attributed to the underlying chromatin architecture of contributing cells. The fragmentation pattern may also be indicative of the method of chromatin compaction during cell death and DNA protection from enzymatic digestion. The genomic structure of a given cell type or cell lineage type may only partially contribute to the heterogeneity of DNA accessibility due to changes in nucleosome stability, conformation, and composition at various stages of cell death or cellular debris trafficking. Additional filtering mechanisms depending on factors such as the mode and mechanism of death or cell clearance may influence cfDNA clearance and release into circulation, resulting in preferential presence or absence of specific cfDNA fragments.

Informative cfDNA fragments may be generated in a cell and released into blood circulation or they may form as a consequence of nuclear DNA fragmentation during processes such as apoptosis, necrosis, autophagy, karyolysis, or pyroptosis wherein different nuclease enzymes act on DNA at difference stages of cell death. The transcriptional status of a cell before it dies may have equally important effects on the fragmentation pattern. cfDNA from all of these sources is intermingled in circulating blood. The resulting sequence-specific DNA cleavage patterns may be analyzed in cfDNA as clinically relevant markers. The intermingled cfDNA fragments can be classified into distinct components corresponding to the different states from which they were derived. These components and clearance factors may represent markers that can be used to differentiate between different states. A fragmentation pattern may be analyzed by identifying specific regions or features where one or more genetic or epigenetic states, or one or more clearance mechanisms, are sufficiently different to be used as a marker indicative of genetic aberrations or pathological conditions. Genetic aberrations that can be measured or inferred by fragmentation pattern analysis may comprise epigenetic variants or changes which may allow fragmentation pattern analysis to determine variations in chromatin organization or structures, which may be a consequence of genomic aberrations or epigenetic changes in DNA.

Another way to distinguish these patterns associated with cell function prior to death and/or the nature of cell death may be through mapping cfNA fragments to custom reference sequences representing different types of fragmentation and quantifying cfNA fragments associated with each reference. The cfNA fragments associated with different custom references may vary by size.

A collection of synthetic oligonucleotide baits comprising sequences complementary to the sequences of specified genomic locations may capture cfNA fragments with high sequence homology to the baits. Novel baits may be designed to capture cell-free fragments that are specific to a given genomic location and size. Baits may be various sizes, labeled, unlabeled, and can represent multiple overlapping and/or non-overlapping genomic regions. Baits may enable preferential capture of specific fragments of various sizes associated with molecular functions of interest. Baits may be constructed based on a custom reference and target those subsequences that are most unique to a given fragmentation. A collection of baits with a targeted capture profile, a bait pool, may represent an optimized combination of bait sequences to target disease-related cfNA fragments and juxtapose pathological and normal states of fragment sizes or abundances. Analysis of fragments captured by a bait pool may enable functional typing by estimating the fractional representation of one or more pool components relative to a combination of other components. Bait sequence design may be driven by various factors such as the expected or empirically observed nucleic acid fragment density in a targeted region, sequence-specific thermodynamics with the free energy of the bait with nucleic acid hybridization described by a nearest neighbor (NN) model, and baits of various size to enable preferential capture of specific fragment lengths associated with a molecular function of interest. Different fragmentation patterns may be distinguished by targeting a genomic region with a combination of baits configured to capture nucleic acid fragments having overlapping sequences but varying in size. For example, custom references (keywords) may be designed to represent NA fragments that are abundantly or selectively present in a given fragmentation pattern in a genomic region. Other sets of custom references may target different sequences within the same genomic region representing different fragmentation patterns. The relative abundance of short and long fragments derived from a genomic site (region) in a biological sample can be quantified by mapping the sequences of captured fragments to these keywords. Fragments can be capture by baits with the same or different sequences from keywords. This method does not require determining the absolute length of each captured fragment, mapping fragment sequences to a reference genome, or identifying the ends of individual fragments. cfNA fragments derived from a genomic region may be sequenced and the sequences matched using alignment-free methods to the keywords of a Custom References. The percentage of cfNA fragments matching each keyword or set of keywords correlates with the relative abundance of different fragmentation patterns.

Characterization and Analysis of cfNA Fragments

Aspects of the present disclosure may extract cell-free nucleic acids from the bloodstream for use as a non-invasive method of detecting disease and monitoring pathological progression or a response to treatment. cfNA may be utilized as a biomarker diagnostic determining the presence of a given disease, prognostic determining the outcome for a subject with a disease, or predictive, determining the response of an individual to a given therapy. Whole blood may be obtained through a minimally invasive method such as a blood draw or fingerstick. Plasma may be isolated from the blood. Circulating nucleic acids may be extracted from this plasma through a nucleic acid extraction protocol, a custom workflow may reduce the complexity in plasma with no nucleic acid extraction, or nucleic acids may be directing enriched from peripheral blood such as through loop-mediated isothermal amplification (LAMP) or CRISPR-mediated, amplification-free target enrichment.

Fragmented DNA and the small amounts of DNA common in cfNA applications, may be amplified prior to analysis. Nucleic acid amplification may refer to generating one or more copies or of a nucleic acid. Nucleic acids may be amplified by the polymerase chain reaction (PCR) for DNA or RT-PCR for RNA. Other nucleic amplification methods include rolling circle amplification (RCA) (Demidov, 2002), strand displacement amplification (SDA) (Walker et al., 1992), helicase-dependent amplification (HDA) (Vincent et al., 2004), nucleic acid sequence-based amplification (NASBA) (Deiman et al., 2002), and loop-mediated amplification (LAMP) (Notomi et al., 2000a). DNA may be amplified generating several millions of copies of a specific segment of DNA from a small amount of starting material, the template. Its specificity may rely on sequence hybridization and its sensitivity may rely on enzyme-based amplification. A PCR amplification method may comprise a series of temperature cycles repeated wherein each cycle denatures DNA duplexes, hybridizes DNA oligonucleotides (primers) flanking the target sequence, and elongates those primers by a DNA polymerase. A cfDNA fragment may be amplified using only one primer hybridizing to the fragment by ligating a common primer site to the ends of every fragment. Additionally, a nucleic acid amplification technique that utilizes a polymerase with helicase activity may be employed. The helicase activity may allow for amplification of DNA at a constant temperature, isothermal amplification, and may be facilitated by primers that form stem-loop DNA structures. Once formed, the stem-loop structures may become the template DNA for further amplification.

Reducing the complexity of circulating nucleic acids to a clinically relevant cell-free fragment representation may comprise several distinct methods or a combination thereof such as selective enrichment, selective capture, or amplicon-based target enrichment. Selective enrichment may comprise using collections of synthetic nucleic acid baits which, when left to hybridize over a period of time, may capture cell-free NA fragments with high homology to these baits, and can represent multiple overlapping and/or non-overlapping genomic regions. NA fragments of specific sizes can be enriched by solid phase reversible immobilization on magnetic beads. The desired NAs may then be eluted from the beads. Amplicon-based target enrichment via PCR-amplification of target regions of interest may comprise using pre-determined specific primers.

Nucleic acid thermodynamics may offer a unique approach in liquid biopsy designs. Many liquid biopsy designs may involve uniformly tiling a genome with overlapping baits that may comprise distinct thermodynamic parameters such as resting temperature. These thermodynamic incongruities may result in significant capture bias which may mask underlying fragment distributions, indicative of disease conditions. For example, hybridization in bulk may be characterized using a model that assumes the process occurs in two steps—the binding of the end of one strand with the complementary end of the other strand followed by a "zipping" of the remaining bases to create a double helix. Such model can be established and then trained using specific synthetic baits to produce custom bait panels with targeted capture profile. Aspects of the present disclosure may estimate and empirically test thermodynamic parameters of a given cell free nucleic acid sequence using approximation of the nearest-neighbor model of nucleic duplex formation constrained by observed nucleosomal occupancy. Enrichment bias may be minimized by thermodynamically protecting an optimized combination of bait sequences which target disease-related cfNA fragments and stabilize the melting temperature of cfNA to bait duplexes. These aspects may enable prioritization and targeting of specific cfNA fragments associated with cell type as related to a function of a disease of interest and juxtapose pathological states of fragment sizes or abundances to normal states. Aspects of the present disclosure may not preserve or maintain the underlying cell-free fragment abundance during enrichment and may distort the underlying cell-free fragment abundance. The presence of cell-free fragments alone may be sufficient for an accurate readout.

Aspects of the present disclosure may detect changes in keyword representation in a set of cfNA fragments through hybridization capture or amplification of non-genomic sequences that may not involve base mapping or positional awareness. A keyword sequence may be a short sequence. A keyword sequence may be 10, 20, 30, 40, 50, 60, 70, 80, 90, 100, 150, 200, 250, 300, 350, 400, 450, 500, 1000, 1500, or more than 1500 nucleotides. A keyword sequence may be 1500, 1000, 500, 450, 400, 350, 300, 250, 200, 150, 100, 90, 80, 70, 60, 50, 40, 30, 20, 10, or less than 10 nucleotides. These keyword sequences may be mapped to the human genome but need not be. It may be important to know only the sequence of these keywords. Each keyword in a list of cfNA fragments may be substring searched and simply counted if it is found. Some cfNA fragments may have one keyword hit while some cfNA fragments will have all keywords and some cfNA fragments will have no keyword hits. A substring match may comprise fuzzy pattern mapping or may be straightforward where an exact subsequence on a cfNA fragment sequence is seen. Positionality of a keywording a fragment may be irrelevant compared to just if a keyword is found in a fragment. cfNA sequence information may not be necessary in detecting changes in keyword representation if baits are designed using these keywords to capture fragments using hybridization and homology. Baits may be mapped to the human genome but may not be mapped to the human genome as such mapping may not be necessary to identify keywords in cfNA fragments. Keywords may be designed to represent NA fragments that are most abundantly or selectively present in a given fragmentation pattern in a genomic region. Keywords may represent underlying transcriptional states thus enabling the sorting of keyword membership in a cfNA fragment and determination of changes in molecular function between timepoints and conditions. Targeting genomic regions with keywords may enable diagnosis of any physiological or pathological condition, or monitor the progression of any disease or pathological condition, treated or untreated, including determining the progression of a cancer, such as pancreatic cancer, or detecting gene expression changes during a course of treatment, such as with steroids by comparing the size or abundance of captured cfNAs with a fragmentation pattern correlating with a molecular function of interest.

An aspect of the present disclosure provides systems and methods for characterizing a fragmentation pattern of cell-free nucleic acid (cfNA) fragments derived from genomic origin as a non-invasive method to screen for, diagnose, determine prognosis, and provide guidance in treatment, and may be applicable to a variety of pathologies and conditions. cfNA may be a non-encapsulated polymeric form of nucleotides of any length (e.g., at least 2, 3, 4, 5, 6, 7, 8, 9, 10, 100, 500, 1000 or more nucleotides), either deoxyribonucleotides or ribonucleotides, or analogs thereof. A nucleic acid may include one or more subunits selected from adenosine (A), cytosine (C), guanine (G), thymine (TO, and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that is specific to one of more complementary A, C, G, T, or U, or complementary to a purine (e.g., A or G, or variant thereof) or pyrimidine (e.g., C, T, or U, or variant thereof). In some examples, a nucleic acid may be single-stranded or double stranded, in some cases, a nucleic acid molecule is circular. Non-limiting examples of nucleic acids include deoxyribonucleic acid (DNA) and ribonucleic acid (RNA). Nucleic acids can include coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid molecule may comprise one or more modified nucleotides, such as methylated nucleotides and nucleotide analogs. cfNA may comprise a singular fragment or may comprise a plurality of cfNA fragments. There may be 1, 2, 3, 4, 5, 6, 7, 8, 9, 10, 15, 20, 25, 30, 35, 40, 45, 50, 60, 70, 80, 90, 100, or more than 100 cfNA fragments in a plurality of cfNA fragments. There may be fewer than about 100, 90, 80, 70, 60, 50, 45, 40, 35, 30, 25, 20, 15, 10, 9, 8, 7, 6, 5, 4, 3, 2, 1 or less than 1 cfNA fragments in a plurality of cfNA fragments.

The presence of circulating nucleic acids (DNA and RNA) detectable in the plasma and serum of subjects with pathological conditions may be investigated to serve as markers for diagnostic or prognostic purposes due to the potential non-invasive nature of sample acquisition. For example, in cancer patients, it has been cfNA markers within the plasma may be identical to the ones found in the carcinogenic tissue of the patient. Circulating nucleic acids may comprise cell-free DNA or cell-free RNA. Circulating RNA may particularly of interest for use in early detection cancer screenings due to RNA markers close association with malignancy.

cfNA may be derived from a biological sample from a subject. A biological sample may be any sample containing or suspected of containing a nucleic acid molecule. For example, a sample can be a biological sample containing one or more nucleic acid molecules. The biological sample can be obtained (e.g., extracted or isolated) from or include blood (e.g., whole blood), plasma, serum, umbilical cord blood, chorionic villi, amniotic fluid, lavage fluid (e.g., bronchoalveolar, gastric, peritoneal, ductal, ear, arthroscopic), biopsy sample (e.g., from pre-implantation embryo), celocentesis sample, fetal nucleated cells or fetal cellular remnants, bile, breast milk, urine, saliva, mucosal excretions, sputum, stool, sweat, vaginal fluid, fluid from a hydrocele (c.g., of the testis), vaginal flushing fluids, pleural fluid, ascitic fluid, cerebrospinal fluid, bronchoalveolar lavage fluid, discharge fluid from the nipple, aspiration fluid from different parts of the body (e.g., thyroid, breast), tears, embryonic cells, or fetal cells (e.g., placental cells). The biological sample can be a fluid or tissue sample (e.g., skin sample). The biological sample can include any tissue or material derived from a living or dead subject. A biological sample can be a cell-free sample. A biological sample can comprise a nucleic acid (e.g., DNA or RNA) or a fragment thereof.

A sample may be heterogeneous, wherein more than one type of nucleic acid species may be present in the sample. For example, heterogeneous nucleic acids can include, but are not limited to, (i) fetal derived and maternal derived nucleic acids, (ii) cancer and non-cancer nucleic acids, (iii) pathogen and host nucleic acids, and more generally, (iv) mutated and wild-type nucleic acids. A sample may be heterogeneous because more than one cell type is present, such as a fetal cell and a maternal cell, a cancer and non-cancer cell, or a pathogenic and host cell. A minority nucleic acid species and a majority nucleic acid species may be present.

Subjects can be humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. A subject can be of any age. Subjects can be, for example, elderly adults, adults, adolescents, pre-adolescents, children, toddlers, infants. A subject may be a patient with a disease and/or a lab animal with a condition.

A composition comprising cfNA may be contacted with an oligonucleotide bait. An oligonucleotide bait comprising synthetic nucleic acid bases complementary to a genomic location may capture cfNA fragments with high homology to the baits. An oligonucleotide may be synthesized, or amplification products may be generated as baits for genomic targets of interest and affixed to a capture modality such as biotinylation and bound to streptavidin coated magnetic beads for solution-based capture. Bound nucleic acids may serve as bait for capturing homologous cfNA fragments. Homologous cfNA fragments from a library that match the bait sequence may serve as targets. After purification of the target enriched library, cfNA fragments with homology to the baits may be enriched, and non-targeted sequences removed. An oligonucleotide bait may be of natural origin. Novel baits may be designed to capture targeted cell-free fragments that are specific to a given genomic location and size. Baits may be various sizes. An oligonucleotide bait may be may comprise at least about 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 400, 500, 600, 700, 800, 900, 1,000, 5,000, 10,000, 50,000, 100,000 or more nucleotides. An oligonucleotide bait may comprise at most about 100,000, 50,000, 10,000, 5,000, 1,000, 900, 800, 700, 600, 500, 400, 300, 250, 200, 175, 150, 125, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, or less nucleotides. An oligonucleotide bait may be unbound (e.g., in solution) or bound (e.g., chemically bonded to a substrate). Oligonucleotide baits may include one or more nonstandard nucleotide(s), nucleotide analog(s), modified nucleotides, or any combination thereof. Oligonucleotide baits may be labeled or unlabeled and may represent multiple overlapping and/or non-overlapping genomic regions. There may be one oligonucleotide bait or a plurality of oligonucleotide baits. There may be greater than about 1, 2, 3, 4, 5, 6, 7, 8, 9, 10, 15, 20, 25, 30, 35, 40, 45, 50, 60, 70, 80, 90, 100, or more than 100 oligonucleotide baits in a plurality of oligonucleotide baits. There may be fewer than about 100, 90, 80, 70, 60, 50, 45, 40, 35, 30, 25, 20, 15, 10, 9, 8, 7, 6, 5, 4, or 3 oligonucleotide baits in a plurality of oligonucleotide baits. An oligonucleotide bait may be conjugated to an affinity tag. An affinity tag may be but is not limited to biotin, albumin binding protein, alkaline phosphatase, horseradish peroxidase, chloramphenicol acetyl transferase, maltose binding protein, hexahistidine tag, glutathione-S-transferase, or β galactosidase.

A bait may comprise a plurality of sets of oligonucleotides with each set specific to a different molecular function of interest. In a plurality of oligonucleotide baits each oligonucleotide bait may comprise a distinct affinity label, such as a fluorescent label. A labeling reagent may be a thiol containing fluorophore. A fluorophore may be a xanthene dye such as a rhodamine dye, Alexa Fluor® dye, an Atto dye, a fluorescent peptide or protein, or a quantum dot. Fluorescent methods may employ such fluorescent techniques such as fluorescence polarization, fluorimetry and fluorescence microscopy, Förster resonance energy transfer (FRET), or time-resolved fluorescence. Fluorescence microscopy may be used to determine the presence of one or more fluorophores.

Baits of various size may enable preferential capture of specific fragment length associated with molecular functions of interest. Baits may be constructed based on the custom reference and target those subsequences that are most representative of or best able to a given fragmentation state. A bait pool or collection of baits with a targeted capture profile, a bait pool, may represent an optimized combination of bait sequences to target disease-related cfNA fragments and juxtapose pathological and normal states of fragment sizes or abundances. cfNA fragments captured by a bait pool may enable functional typing by estimating the fractional representation of one or more pool components relative to a combination of other components a fragment may hybridize to.

An oligonucleotide bait may be conjugated to a solid surface. A solid surface may be any suitable material which can be surface modified to incorporate a binding partner to an immobilization tag. A solid surface may comprise magnetic beads which facilitate removal of bait and captured target of interest. A solid surface may comprise the surface of resins, gels, quartz particles, or combinations thereof. In some non-limiting examples, the methods contemplate using oligonucleotide baits that have been immobilized on the support of an aminosilane modified surface, crosslinked polystyrene/polyethylene glycol (e.g. Tentagel®) beads, crosslinked polystyrene/polyethylene glycol (e.g. Tentagel®) resins, or other similar beads or resins. The surface used herein may be a hydrogel, such as alginate. The surface used herein may be coated with a polymer, such as polyethylene glycol. Fluoropolymers (Teflon™-AF (Dupont), Cytop® (Asahi Glass, Japan)), aromatic polymers (polyxylenes (Parylene, Kisco, Calif.), polystyrene, polymethmethylacrytate) and metal surfaces (gold coating)), coating schemes (spin-coating, dip-coating, electron beam deposition for metals, thermal vapor deposition and plasma enhanced chemical vapor deposition) and functionalization methodologies (polyallylamine grafting, use of ammonia gas in PECVD, doping of long chain end-functionalized fluorous alkanes etc) may be used in the methods described herein as a useful surface. A solid support may be conjugated with different addressable makers.

A solid surface may be a bead. A bead may be a polymer such as a polystyrene bead or polystyrene cross-linked with divinylbenzene. The solid support bead may comprise an iron oxide core. A bead may comprise a metal salt such as a copper salt, a magnesium salt, a calcium salt, or a manganese salt. A bead may be cellulose, cellulose derivatives, gelatin, acrylic resins, glass, silica gels, polyvinyl pyrrolidine (PVP), co-polymers of vinyl and acrylamide, polyacrylamides, latex gels, dextran, crosslinked dextrans (e.g., Sephadex™), rubber, silicon, plastics, nitrocellulose, natural sponges, metal, and agarose gel (Sepharose™). The bead diameter may depend on the density of the oligonucleotide bait or sample assayed requiring smaller or larger beads. The bead may have a diameter of at least about 1 micrometer (μm), 5 μm, 10 μm, 25 μm, 50 μm, 75 μm, 100 μm, 150 μm, 200 μm, 250 μm, 300 μm, 400 μm, 500 μm, 750 μm, 1,000 μm, or more micrometers. The bead may have a diameter of at most about 1,000 μm, 750 μm, 500 μm, 400 μm, 300 μm, 250 μm, 200 μm, 150 μm, 100 μm, 75 μm, 50 μm, 25 μm, 10 μm, 5 μm, 1 μm, or less than 1 micrometers.

A. oligonucleotide bait may be coupled to a functional unit on the surface of the bead. A bead may be a single bead or may be among a plurality of beads. The plurality of beads may comprise at least 1,000 wells. There may be 2, 3, 4, 5, 6, 7, 8, 9, 10, 15, 20, 25, 30, 35, 40, 45, 50, 60, 70, 80, 90, 100, 200, 300, 400, 500, 1000, 1500, 2000, 3000, 4000, 5000, 10,000, 100,000, 1,000,000 or more than 1,000,000 wells in a plurality of beads.

A solid support may be a planar surface. A planar surface may be the interior of a well. A well may have a dimension of x by y by z, where x, y, and z are each independently at least about 0.1 µm, 1 µm, 5 µm, 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 110 µm, 120 µm, 130 µm, 140 µm, 150 µm, 160 µm, 170 µm, 180 µm, 190 µm, 200 µm, 250 µm, 300 µm, 400 µm, 500 µm, 600 µm, 700 µm, 800 µm, 900 µm, 1,000 µm, or more micrometers. A well may have a dimension of x by y by z, where x, y, and z are each independently at most about 1,000 µm, 900 µm, 800 µm, 700 µm, 600 µm, 500 µm, 400 µm, 300 µm, 250 µm, 200 µm, 190 µm, 180 µm, 170 µm, 160 µm, 150 µm, 140 µm, 130 µm, 120 µm, 110 µm, 100 µm, 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 10 µm, 5 µm, 1 µm, 0.1 µm, or less micrometers. For example, a well can have an x dimension of 434 µm, a y dimension of 30 µm, and a z dimension of 510 µm. In another example, a well can have an x and y dimension of 16 µm and a z dimension of 1 µm. The planar surface may be a well among a plurality of wells. The plurality of wells may comprise at least two wells. The plurality of wells may comprise at least 1,000 wells. There may be 2, 3, 4, 5, 6, 7, 8, 9, 10, 15, 20, 25, 30, 35, 40, 45, 50, 60, 70, 80, 90, 100, 200, 300, 400, 500, 1000, 1500, 2000, 3000, 4000, 5000, 10,000, 100,000, 1,000,000 or more than 1,000,000 wells in a plurality of wells. A well may comprise a bead or a planar surface may incorporate a bead.

An oligonucleotide bait may hybridize to and capture cfNA fragments and the fragmentation pattern of the captured cfNA fragments may be characterized. The plurality of cell-free nucleic acids that hybridize to a bait oligonucleotide may be at least about 70%, 75%, 80%, 85%, 90%, 95%, 97%, 98%, 99%, or more complementary to an oligonucleotide bait sequence or plurality of oligonucleotide bait sequences. The plurality of cell-free nucleic acid molecules may be at most about 99%, 98%, 97%, 95%, 90%, 85%, 80% or less complementary to an oligonucleotide bait sequence or plurality of oligonucleotide bait sequences. Non-hybridized cfNA sequences may be separated from hybridized target sequences, thereby uniformly enriching a population of cell-free DNA fragments with high discrimination potential.

A fragmentation pattern may detect, diagnose, monitor the progress of a condition over time, study the effectiveness of therapies, or determine the prognosis of a disease or pathological condition. Non-limiting examples of diseases or conditions that may be diagnosed or monitored with a non-invasive cfNA diagnostic may include hematological malignancies, solid tumor malignancies, metastatic cancer, benign tumors, HIV/AIDS, autoimmune disease, hepatitis B, hepatitis C, rheumatoid arthritis, multiple sclerosis, psoriasis, uveitis, scleroderma, systemic lupus erythematosus, diabetes mellitus, eczema, Parkinson's disease, congenital disease, genetic abnormalities, or Alzheimer's disease.

A fragmentation pattern may detect, diagnose, monitor the progress of a cancer over time, study the effectiveness of therapies, or determine the prognosis of a cancer. While individual malignancies may provide unique genomes of malignant cells, fragment analysis may also comprise those of normal non-aberrant cells associated with the presence of a tumor. Such fragment analysis may be diagnostic and clinically relevant but may not be directly of a cancerous origin as tumor vasculature may comprise normal cells as well as malignant cells. Non-limiting examples of cancers that may be diagnosed or monitored with a non-invasive cfNA diagnostic include: acute lymphoblastic leukemia, acute myeloid leukemia, adrenocortical carcinoma, AIDS-related cancers, AIDS-related lymphoma, anal cancer, appendix cancer, astrocytoma, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/ malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pincal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma Merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

Aspects of the present disclosure may comprise a method of characterizing a fragmentation pattern of cfNA fragments derived from a genomic region wherein characterizing the fragmentation pattern of the cfNA fragments comprises analyzing sizes or abundance of the cfNA fragments. Characterizing a fragmentation pattern may comprise identifying genomic locations or lengths of cfNA fragments or may not comprise identifying genomic locations of lengths of the cfNA fragments. Fragments may be comprised of small/ short or large/long fragments. The term "small fragment" and the term "short fragment" are interchangeable. The term "large fragment" and the term "long fragment" are interchangeable. A small fragment may comprise fewer nucleotides than a large fragment. A small fragment may comprise about 1, 2, 3, 4, 5, 6, 7, 8, 9, 10, 11, 12, 13, 14, 15, 20. 25. 30, 35, 40, 45, 50, 60, 70, 80, 90, 100, 150, 200, 230, or more than 230 base pairs. A small fragment may comprise about less than 230, 200, 150, 100, 90, 80, 70, 60, 50, 45, 40, 35, 30, 25, 20, 15, 10, 9, 8, 7, 6, 5, 4, 3, 2, or 1 base pair. A small fragment may have a distribution centered around approximately 170 base pairs and may be indicative of mononucleosomal protection. A large fragment may comprise about, 50, 55, 60, 65, 70, 75, 80, 85, 90, 100, 150, 200, 250, 300, 350, 400, 450, 500, 600, 700, 800, 900, 1000, or more than 1000 base pairs. A large fragment may comprise about 1000, 900, 800, 700, 600, 500, 450, 400, 350, 300, 250, 200, 150, 100, 90, 80, 70, 60, 50, or less than 50 base pairs. A large fragment length may have a size distribution centered around approximately 330 base pairs and may be indicative of dinucleosomal protection. The determination of a large or a small cfNA may be if a fragment is larger or smaller than 230 base pairs in length. An amount of large cfNA fragments comprising at least 230 nucleotides may be compared to a small cfNA fragment comprising less than 230 nucleotides. A large cfNA fragment may comprise at least 185, 190, 200, 210, 220, 230, 240, 250, 255, 270, or 310 nucleotides. A small cfNA fragment may comprise less than 220, 205, 190, 175, 170, 160, 150, 140, 130, 120, or 110 nucleotides. An increased abundance of large cfNA fragments may be indicative of a medical condition. A ratio of large cfNA fragments to small cfNA fragments of at least 0.01, 0.05, 0.1, 0.2, 0.25, 0.3, 0.35 or 0.4 may be indicative of a medical condition. A ratio of large cfNA fragments to small cfNA fragments may be at least 0.1, 0.15, 0.2, 0.25, 0.3, 0.35, 0.4, 0.45, 0.5, 0.6, 0.7, 0.8, 0.9, or 1 and may be indicative of a medical condition. A ratio of large cfNA to small cfNA fragments may be less than 1, 0.9, 0.8, 0.7, 0.6, 0.5, 0.45, 0.4, 0.35, 0.3, 0.25, 0.2, 0.15, 0.1, or less than 0.1.

Large and short cfNA fragments may span one exon or may span multiple exons. cfNA fragments may be analyzed with regard to the representation and distribution of specific sequences or epigenetic features such as DNA digestion or methylation patterns. Fragmented DNAs may be generated in a cell and released as cfDNA into blood circulation as a result of nuclear DNA fragmentation during cell processes such as apoptosis and necrosis. Such fragmentation may be produced as a result of different nuclease enzymes acting on DNA in different stages of cells, resulting in sequence-specific DNA cleavage patterns which may be analyzed in cfDNA fragmentation patterns. Classifying such clearance patterns may be a clinically relevant marker of cell environments (e.g., tumor microenvironments, inflammation, disease states, etc.). Fragmentation patterns may be analyzed by classifying cfDNA fragments into distinct components corresponding to the different chromatin states from which they were derived. For example, a fragmentation pattern may be expressed as a sum of components representing different underlying chromatin states.

A specific genomic region may be identified as profile discriminators using public databases and/or empiric experimental data. For example, a subset of designed baits may exhibit enrichment bias for cfNA fragments observed in healthy non-diseased cfNA samples while another subset of baits may target genomic regions enriched in all or some pathological conditions examined during bait design. Cell-free NA targets that are bound to baits may be quantified.

Methods for analyzing sizes of cfNA fragments or quantifying cfNAs may include, but are not limited to, gas chromatography, supercritical fluid chromatography, liquid chromatography (including partition chromatography, adsorption chromatography, ion exchange chromatography, size exclusion chromatography, thin-layer chromatography, and affinity chromatography), electrophoresis (including capillary electrophoresis, capillary zone electrophoresis, capillary isoelectric focusing, capillary electrochromatography, micellar electrokinetic capillary chromatography, isotachophoresis, transient isotachophoresis and capillary gel electrophoresis), comparative genomic hybridization (CGH), microarrays, bead arrays, and high-throughput genotyping such as with the use of molecular inversion probe (MIP). Pathological conditions may be predicted with a pathological condition probability based on a comparison between the estimated fractional representation and a predetermined association of the one or more distinct components with clinical reference data.

cfNA fragments may be separated with microfluidic separation. Microfluidic separation may comprise a microfluidic cassette or "chip". A microfluidic chip may comprise a solid surface such as a polystyrene which may combine nucleic acid isolation by solid-phase extraction; isothermal enzymatic amplification such as Loop-mediated AMPlification (LAMP), Nucleic Acid Sequence Based Amplification (NASBA), or Recombinase Polymerase Amplification (RPA); and real-time optical detection of cfNA analytes. A microfluidic cassette may incorporate an embedded nucleic acid binding membrane in an amplification reaction chamber. Target nucleic acids extracted from a lysate may be captured on the membrane and amplified at a constant incubation temperature. The amplification product may be labeled with a fluorophore reporter but need not be. A fluorophore reporter may be excited with a LED light source and monitored in situ in real time with a photodiode or a CCD detector. For whole blood analysis, a filtration device that separates plasma from whole blood to provide cell-free samples may be utilized. A microfluidic chip may utilize a consistent flow design or an oscillatory flow design. In a consistent flow design, nucleic acids, droplets, or solution may be in continuous-flow. A solution may be viscous or non-viscous. Nucleic acids, droplets, or solution may be stationary or semi-stationary. Nucleic acids, droplets, or solution may be in motion. A microfluidic chip may utilize oscillating or bidirectional flow. A microfluidic chip may combine the cycling flexibility of a stationary chamber-based system and the fast dynamics of a continuous flow system. Nucleic acids, droplets, or solution may be transported back and forth through a single channel or may be transported in multiple channels or capillaries. The channel(s) may span various temperature zones. A microfluidic chip may be attached to a pumping system such as but not limited to external pumps and integrated micropumps. There may be on board power or an external power source. Centrifugal force and/or capillary forces may be used to control the fluid flow. A compact disc format may be used to house the reaction chambers or other components. A droplet may serve as a reactor environment allowing for fast reagent mixing and minimum surface adsorption. Interfacial chemistry may be used to create such a reactor droplet (e.g. an oil-water plug may be flowed through a fluid capillary to create a water-in-oil droplet).

To connect specific baits representative of a molecular function, a deconvolution analysis may be performed. A molecular function may be assigned to bait capture products with a series of calibrating experiments where a benchmark dataset may represent a known molecular function state. For example, 50 baits most enriched for molecular functions can be identified using moderated t-tests and fold changes. Scores for each molecular function signature may be assessed in disease profiles by computing fragment counts in that subtype relative to all others and calculating an arithmetic mean of the fragment counts. Scores may be grouped by hierarchical clustering according to Euclidian distance. Alternative deconvolution methods may be used, such as maximum likelihood/Conjugate gradient, quadratic programming, non-negative Matrix Factorization, v-Support Vector Regression, quadratic programming, Unified Particle Swarm Optimization, or a Latent Dirichlet Allocation (LDA) model. Using fragment counts associated with one of collection of baits, mixture proportions may be estimated based on benchmark counting data, or the number of cell/tissues type de novo may be inferred using the following approach:

If S is an n×k bait-specific fragment count matrix that contains k cell types and n genes, W may be a k×p matrix where each column of W contains the frequencies of k cell types in a particular observation, and O may be an n×p count matrix that may contain the observed bait-specific fragment counts level, where n may represent the number of genes and p may be the number of observed tissue samples. The mixing process can be modeled through a linear model:

$$O = S \times W \quad \text{(Equation 1)}$$

where S may represent the source signal, W may be the weight matrix for cell type frequencies, and O may be the observation on tissue samples. In a typical fragment counts profiling setting, O may be measured through microarray or RNA-seq. Both W, a cell type frequency matrix, and S may be unknown, where both S and W may need be estimated. W may be estimated using cell type specific markers and a linear model solved using the estimated W.

As a set of genes may have high fragment counts in a specific cell type and low counts in all other cell types, the proportion of each cell type present in a blood sample may be predicted using these genes. For example, $X_S$ may be an m×k matrix that contains m cell type specific genes for k cell types. In each cell type, there may be multiple cell type specific genes. As each gene may have higher bait-specific fragment counts in a single cell type, an average of all the genes that are highly expressed in a single cell type may be determined and solve the matrix as $\tilde{X}_S$:

$$X_S = \begin{pmatrix} g_{11} & 0 & \cdots & 0 \\ g_{21} & 0 & \cdots & 0 \\ 0 & g_{32} & \cdots & 0 \\ 0 & g_{42} & \cdots & 0 \\ 0 & g_{52} & \cdots & 0 \\ 0 & 0 & \ddots & \vdots \\ 0 & 0 & \cdots & g_{mk} \end{pmatrix} \Rightarrow \tilde{X}_S = \begin{pmatrix} \bar{g}_1 & 0 & \cdots & 0 \\ 0 & \bar{g}_2 & \cdots & 0 \\ 0 & 0 & \ddots & 0 \\ 0 & 0 & \cdots & \bar{g}_k \end{pmatrix}$$

$\tilde{X}_S$ may be unknown, however, the corresponding fragment counts for cell type specific markers, $O_S$ and $\tilde{O}_S$ may be measured on the observed mixed samples. Substituting $\tilde{X}_S$ and $\tilde{O}_S$ to Equation 1, it may be obtained $$\tilde{O}_S = \tilde{X}_S \times W \quad \text{(Equation 2)}$$

$\tilde{X}_S$ may be a diagonal matrix, thus each side of Equation 2 may be multiplied by the $\tilde{X}^{-1}S$ and Equation 3 may be obtained:

$$\tilde{X}_S^{-1} \tilde{O}_S = W \quad \text{(Equation 3)}$$

As W may be a frequency matrix and each column of W may sum to 1, a system of linear questions of k unknown parameters, g⁻1 . . . g⁻k, may be formed where:

$$\sum_{i=1}^{k} \left( \tilde{X}_S^{-1} \tilde{O}_S \right)_{ij} = 1 \quad \text{(Equation 4)}$$

Where the number of observations on the mixed samples are greater the number of cell types involved that is p>k, the system of equations may be solved with k unknown parameters. Where g⁻1 . . . g⁻k may be known, $\tilde{X}^{-1}S$ may be taken into Equation 3 and the cell type frequency matrix may be computed.

In digital sorting on blood samples, cfNA fragment count data in blood samples and a set of gene symbols known to have high bait-specific fragment counts in a specific cell type may be input to obtain a fragment count profile for each of the cell types in a blood sample. If W is not known, W may be estimated using $X_S$ and Equation 3. If W is known, S may be estimated through quadratic programming where O may be the fragment counts profile in blood samples, S may be the bait-specific fragment count profile for pure cell types, W may be the weight matrix estimated using the marker genes, and $t_1$ and $t_2$ may be the maximum and minimum measurable fragment counts level:

$$\min_{S} \|O - SW\|_2$$

$$\text{s.t } S < t_1 \text{ and } S > t_2$$

Aspects of the present disclosure may comprise a method of characterizing a fragmentation pattern of cell-free nucleic acid fragments derived from a genomic region comprising contacting a composition comprising cfNA with an oligonucleotide bait or baits and analyzing abundance of cfNA fragments that hybridize to the oligonucleotide bait or baits, wherein the oligonucleotide bait or baits comprise a sequence complementary to a sequence of the genomic region and where analyzing the size or abundance of the cfNA fragments comprises sequencing of the cfNA fragments and performing alignment-free sequence comparison of the cfNA nucleotide sequences to a local reference sequence. A next generation sequencing library may be prepared by sequencing cell-free NA fragments and by documenting the genomic distribution of the cfNA fragments into a database. The database may be processed for signal transformation for some embodiments. A local reference sequence may comprise a known genomic region associated with a pathological condition probability based on a comparison between the estimated fractional representation and a predetermined association of the one or more distinct components with clinical or empirical reference data. A reference sequence may comprise data from the human genome or another mammalian genome or may comprise individual subject data. Characterizing cfNA fragments. derived from a genomic region may comprise comparing mobilities of cfNA fragments to a known standard. A known standard may comprise the human genome or a mapped animal genome or may comprise clinical or empirical data.

An aspect of the present disclosure may comprise a method of characterizing cfNA fragments derived from a genomic region, comprising contacting a composition comprising cfNA with an oligonucleotide bait, and analyzing sizes of cfNA fragments that hybridize to the oligonucleotide bait, wherein the oligonucleotide bait comprises a sequence complementary to a sequence of the genomic region and wherein analyzing the sizes of cfNA fragments may comprise stretching cfNA fragments, and acquiring an image of the cfNA fragments. Analyzing the sizes of cfNA fragments may comprise capturing an end of a cfNA fragment in an optical trap or flow-stretching a cfNA fragment. An image of cfNA fragments may be acquired with commercially available optical devices such as, light microscopes, confocal microscopes, fluorescent microscopes, optical sequencers, or imaging platforms. For example, a conventional microscope equipped with total internal reflection illumination and an intensified charge-couple device (CCD) detector may be available. Imaging with a high sensitivity CCD camera may allow the instrument to simultaneously record the fluorescent intensity of multiple individual (i.e., single) peptide molecules distributed across a surface. Image collection may be performed using an image splitter that directs light through two band pass filters (one suitable for each fluorescent molecule) to be recorded as two side-by-side images on the CCD surface.

An aspect of the present disclosure may comprise a method of characterizing cfNA fragments derived from a genomic region, comprising contacting a composition comprising cfNA with an oligonucleotide bait, and analyzing sizes of cfNA fragments that hybridize to the oligonucleotide bait, wherein the oligonucleotide bait comprises a sequence complementary to a sequence of the genomic region and wherein analyzing the sizes of cfNA fragments may comprise contacting a cfNA fragment with a dye, separating the cfNA fragments into droplets, flowing the droplets past a detector, measuring the fluorescence of each cfNA fragment, and calculating a size from the fluorescent intensity, wherein the fluorescence of the dye is enhanced by contact with the cfNA fragments. cfNAs, droplets, or solutions in a microfluidic device, in a well, attached to a support, or in an array may be incubated, split, and merged in a microfluidic device. Droplets may vary in size. Droplets may be at least about 0.5 micrometers (μ), 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70μ, 80, μm, 90 μm, 100 μm, 150 μm, 200 μm, 250 μm, 300 μm, 350 μm, 400 μm, 450 μm, 500 μm, 600 μm, 700 μm, 800 μm, 900 μm, 1000 μm or more in diameter. They may be less than or greater than these diameters or any value in between. cfNA, droplet, or solution formation frequency may be at least about 0.5 Hertz (Hz), 1 Hz, 2 Hz, 3 Hz, 4 Hz, 5 Hz, 6 Hz, 7 Hz, 8 Hz, 9 Hz, 10 Hz, 20 Hz, 30 Hz, 40 Hz, 50 Hz, 60Hz, 70 Hz, 80 Hz, 90 Hz, 100 Hz, 200 Hz, 300 Hz, 400 Hz, 500 Hz, 600 Hz, 700 Hz, 800 Hz, 900Hz, 1,000 Hz, 2,000 Hz, 3,000 Hz, 4,000 Hz, 5,000 Hz, 6,000 Hz, 7,000 Hz, 8,000 Hz, 9,000 Hz, 10,000 Hz or more. The frequency may be less than or greater than those listed here or any value in between.

A solution comprising the cfNA molecules may be flowed at a flow rate about 1 microliter (μL)/minute (min) to about 12 μL/min. The solution comprising the cfNA molecules may be flowed at a flow rate about 1 μL/min to about 2 μL/min, about 1 μL/min to about 3 μL/min, about 1 μL/min to about 4 μL/min, about 1 μL/min to about 5 μL/min, about 1 μL/min to about 6 μL/min, about 1 μL/min to about 7 μL/min, about 1 μL/min to about 8 μL/min, about 1 μL/min to about 9 μL/min, about 1 μL/min to about 10 μL/min, about 1 μL/min to about 11 μL/min, about 1 μL/min to about 12 μL/min, about 2 μL/min to about 3 μL/min, about 2 μL/min to about 4 μL/min, about 2 μL/min to about 5 μL/min, about 2 μL/min to about 6 μL/min, about 2 μL/min to about 7 μL/min, about 2 μL/min to about 8 μL/min, about 2 μL/min to about 9 μL/min, about 2 μL/min to about 10 μL/min, about 2 μL/min to about 11 μL/min, about 2 μL/min to about 12 μL/min, about 3 μL/min to about 4 μL/min, about 3 μL/min to about 5 μL/min, about 3 μL/min to about 6 μL/min, about 3 μL/min to about 7 μL/min, about 3 μL/min to about 8 μL/min, about 3 μL/min to about 9 μL/min, about 3 μL/min to about 10 μL/min, about 3 μL/min to about 11 μL/min, about 3 μL/min to about 12 μL/min, about 4 μL/min to about 5 μL/min, about 4 μL/min to about 6 μL/min, about 4 μL/min to about 7 μL/min, about 4 μL/min to about 8 μL/min, about 4 μL/min to about 9 μL/min, about 4 μL/min to about 10 μL/min, about 4 μL/min to about 11 μL/min, about 4 μL/min to about 12 μL/min, about 5 μL/min to about 6 μL/min, about 5 μL/min to about 7 μL/min, about 5 μL/min to about 8 μL/min, about 5 μL/min to about 9 μL/min, about 5 μL/min to about 10 μL/min, about 5 μL/min to about 11 μL/min, about 5 μL/min to about 12 μL/min, about 6 μL/min to about 7 μL/min, about 6 μL/min to about 8 μL/min, about 6 μL/min to about 9 μL/min, about 6 μL/min to about 10 μL/min, about 6 μL/min to about 11 μL/min, about 6 μL/min to about 12 μL/min, about 7 μL/min to about 8 μL/min, about 7 μL/min to about 9 μL/min, about 7 μL/min to about 10 μL/min, about 7 μL/min to about 11 μL/min, about 7 μL/min to about 12 μL/min, about 8 μL/min to about 9 μL/min, about 8 μL/min to about 10 μL/min, about 8 μL/min to about 11 μL/min, about 8 μL/min to about 12 μL/min, about 9 μL/min to about 10 μL/min, about 9 μL/min to about 11 μL/min, about 9 μL/min to about 12 μL/min, about 10 μL/min to about 11 μL/min, about 10 μL/min to about 12 μL/min, or about 11 μL/min to about 12 μL/min. The solution comprising the cfNA molecules may be flowed at about 1 μL/min, about 2 μL/min, about 3 μL/min, about 4 μL/min, about 5 μL/min, about 6 μL/min, about 7 μL/min, about 8 μL/min, about 9 μL/min, about 10 μL/min, about 11 μL/min, or about 12 μL/min. The solution comprising the cfNA molecules may be flowed at least about 1 μL/min, about 2 μL/min, about 3 μL/min, about 4 μL/min, about 5 μL/min, about 6 μL/min, about 7 μL/min, about 8 μL/min, about 9 μL/min, about 10 μL/min, or about 11 μL/min. The solution comprising the polypeptide molecules may be flowed at most about 2 μL/min, about 3 μL/min, about 4 μL/min, about 5 μL/min, about 6 μL/min, about 7 μL/min, about 8 μL/min, about 9 μL/min, about 10 μL/min, about 11 μL/min, or about 12 μL/min.

An aspect of the present disclosure may comprise a method of characterizing cfNA fragments derived from a genomic region, comprising: contacting a composition comprising cfNA with an oligonucleotide bait, and sequencing cfNA fragments that hybridize to the oligonucleotide bait and performing alignment-free sequence comparison of the cfNA fragment nucleotide sequences to a local reference sequence, wherein the oligonucleotide bait may comprise a sequence complementary to a sequence of the genomic region. cfNAs may be sequenced with a variety of methods including but not limited to next generation sequencing, somatic mutation analysis, amplicon sequencing, massive parallel sequencing, Maxam-Gilbert sequencing, Sanger sequencing, deNovo sequencing, shotgun sequencing, short read sequencing, long read sequencing, transcriptome profiling, single molecule real time sequencing, ion semiconductor sequencing, pyrosequencing, sequencing by synthesis, nanopore sequencing, polony sequencing, massively parallel signature sequencing, DNA nanoball sequencing, or sequencing by ligation. Alignment-free sequence comparison of cfNA fragment nucleotide sequences to a local reference sequence may comprise any method of quantifying sequence similarity or dissimilarity that does not use or produce alignment, for example assignment of residue-residue correspondence. Alignment-free methods may not rely on dynamic programming, may be resistant to shuffling or recombination events, may be applicable when low sequence conservation cannot be handled reliably by alignment, and therefore may be suitable for whole genome comparisons. Alignment-free methods may comprise those based on k-mer/word frequency, length of common substrings, number of word matches, based on micro-alignments, based on information theory, or methods based on graphical representation.

Multiple sequence lengths of a genome of interest may be isolated without sequencing. Multiple genomes of interest from a biological sample may be simultaneously isolated without sequencing. A biological sample may be contacted with a plurality of sets of pathogen-specific oligonucleotides. In one example, at least one set of baits may comprise polyribonucleotides and at least one set of baits may comprise polydeoxyribonucleotides. Thus, the biological sample may be contacted with a plurality of sets of pathogen-specific polyribonucleotides and a plurality of sets of pathogen-specific polydeoxyribonucleotides. Each set of pathogen-specific oligonucleotides may be provided with a different immobilization tag.

An aspect of the present disclosure may comprise a method of characterizing cfNA fragments derived from a genomic region, comprising: contacting a composition comprising cfNA with an oligonucleotide bait, and sequencing cfNA fragments that hybridize to the oligonucleotide bait and performing alignment-free sequence comparison of the cfNA fragment nucleotide sequences to a local reference sequence, wherein the oligonucleotide bait may comprise a sequence complementary to a sequence of the genomic region quantifying a relative amount of cfNA fragment sequences aligning to sequences distal to an end of the oligonucleotide bait versus cfNA fragment sequences aligning to sequences distal to a second end of the oligonucleotide bait.

Aspects of the present disclosure may comprise a method of characterizing cfNA fragments derived from a genomic region, comprising: contacting a composition comprising cfNA with an oligonucleotide bait, and sequencing cfNA fragments that hybridize to the oligonucleotide bait and identifying two or more subregions within the genomic region and counting a number of cfNA fragments matching each subregion, wherein the oligonucleotide bait may comprise a sequence complementary to a sequence of the genomic region. A subregion within a genomic region may comprise a group of genomic segments with similar functional characteristics such as untranslated regions (UTRs), predicted exon, or transcription factor binding sites. A cfNA fragment may match a subregion if a sequence of the fragment is identical to the sequence of the subregion or a sequence of the fragment is assigned to the subregion via approximate string matching. Once the counts and size distributions for each reference sequence match are obtained, a weighted score can be re-defined using parametric (such as linear regression), a non-parametric (such as artificial neural networks) models, e.g. an arbitrary ratio. Approximate string matching (fuzzy string searching) may comprise a. technique of finding strings that match a pattern approximately as opposed to exactly. The closeness of a match may be measured in terms of the edit distance, the number of primitive operations necessary to convert the string into an exact match between the string and the pattern such as by characterizing matching insertions, deletions, transpositions, or substitutions. A cfNA fragment may match a subregion if a sequence of the fragment is at least about 70%, 75%, 80%, 85%, 90%, 95%, 97%, 98%, 99%, or more complementary to an oligonucleotide bait sequence or plurality of oligonucleotide bait sequences.

An aspect of the present disclosure may comprise a method of characterizing cfNA fragments derived from a genomic region, comprising: contacting a composition comprising cfNA with a first oligonucleotide bait and a second oligonucleotide bait, analyzing the cfNA fragments that hybridize to the first oligonucleotide bait, and analyzing the cfNA fragments that hybridize to the second oligonucleotide bait, wherein the first oligonucleotide bait and the second oligonucleotide bait comprise sequences complementary to sequences of the genomic region, and wherein the method does not comprise identifying genomic locations or lengths of the cfNA fragments. cfNA fragments that hybridize to the first bait may be compared to cfNA fragments that hybridize to the second bait thus allowing inference or comparison of distinct pathological states in a sample. One or a plurality of oligonucleotide baits may be targeted toward cfNA fragments derived from a genomic region. There may be 1, 2, 3, 4, 5, 6, 7, 8, 9, 10, 15, 20, 25, 30, 35, 40, 45, 50, 60, 70, 80, 90, 100, or more than 100 oligonucleotide baits in a plurality of oligonucleotide baits. There may be fewer than about 100, 90, 80, 70, 60, 50, 45, 40, 35, 30, 25, 20, 15, 10, 9, 8, 7, 6, 5, 4, or 3 oligonucleotide baits in a plurality of oligonucleotide baits. For example, two oligonucleotide baits may be targeted to a cfNA fragment derived from a genomic region. A plurality of overlapping oligonucleotide baits spanning a pathogenic genomic region of interest may be targeted to a cfNA fragment derived from a genomic region. Providing a set of oligonucleotide baits with different immobilization tags specific to different binding partners may allow the selective identification of multiple distinct pathogenic or host genomes as different immobilization tags may be used. Oligonucleotide baits may comprise various sizes, labels, and may represent multiple overlapping and/or non-overlapping genomic regions. A first oligonucleotide bait and a second oligonucleotide bait may be conjugated to an affinity tag wherein the affinity tag may be but is not limited to biotin, albumin binding protein, alkaline phosphatase, horseradish peroxidase, chloramphenicol acetyl transferase, maltose binding protein, hexahistidine tag, glutathione-S-transferase, or β galactosidase.

A first oligonucleotide bait and a second oligonucleotide bait may be conjugated to a solid surface. A solid surface may comprise magnetic beads which facilitate removal of bait and captured target of interest. A solid surface may comprise the surface of resins, gels, quartz particles, or combinations thereof. In some non-limiting examples, the methods contemplate using oligonucleotide baits that have been immobilized on the support of an aminosilane modified surface, crosslinked polystyrene/polyethylene glycol (e.g. Tentagel®) beads, crosslinked polystyrene/polyethylene glycol (e.g. Tentagel®) resins, or other similar beads or resins. The surface used herein may be a hydrogel, such as alginate. The surface used herein may be coated with a polymer, such as polyethylene glycol. Fluoropolymers (Teflon™-AF (Dupont), Cytop® (Asahi Glass, Japan)), aromatic polymers (polyxylenes (Parylene, Kisco, Calif.), polystyrene, polymethmethylacrytate) and metal surfaces (gold coating)), coating schemes (spin-coating, dip-coating, electron beam deposition for metals, thermal vapor deposition and plasma enhanced chemical vapor deposition) and functionalization methodologies (polyallylamine grafting, use of ammonia gas in PECVD, doping of long chain end-functionalized fluorous alkanes etc) may be used in the methods described herein as a useful surface. A solid support may be conjugated with different addressable makers.

A solid surface may be a bead. A bead may be a polymer such as a polystyrene bead or polystyrene cross-linked with divinylbenzene. The solid support bead may comprise an iron oxide core. A bead may comprise a metal salt such as a copper salt, a magnesium salt, a calcium salt, or a manganese salt. A bead may be cellulose, cellulose derivatives, gelatin, acrylic resins, glass, silica gels, polyvinyl pyrrolidine (PVP), co-polymers of vinyl and acrylamide, polyacrylamides, latex gels, dextran, crosslinked dextrans (e.g., SephadexTM), rubber, silicon, plastics, nitrocellulose, natural sponges, metal, and agarose gel (Sepharosc™M). The bead diameter may depend on the density of the oligonucleotide bait or sample assayed requiring smaller or larger beads. The bead may have a diameter of at least about 1 micrometer (μm), 5 μm, 10 μm, 25 μm, 50 μm, 75 μm, 100 μm, 150 μm, 200 μm, 250 μm, 300 μm, 400 μm, 500 μm, 750 μm, 1,000 μm, or more micrometers. The bead may have a diameter of at most about 1,000 μm, 750 μm, 500 μm, 400 μm, 300 μm, 250 μm, 200 μm, 150 μm, 100 μm, 75 μm, 50 μm, 25 μm, 10 μm, 5 μm, 1 μm, or less than 1 micrometers. A. oligonucleotide bait may be coupled to a functional unit on the surface of the bead. A bead may be a single bead or may be among a plurality of beads. The plurality of beads may comprise at least 1,000 wells. There may be 2, 3, 4, 5, 6, 7, 8, 9, 10, 15, 20, 25, 30, 35, 40, 45, 50, 60, 70, 80, 90, 100, 200, 300, 400, 500, 1000, 1500, 2000, 3000, 4000, 5000, 10,000, 100,000, 1,000,000 or more than 1,000,000 wells in a plurality of beads.

A solid support may be a planar surface. A planar surface may be the interior of a well. A well may have a dimension of x by y by z, where x, y, and z are cach independently at least about 0.1 μm, 1 μm, 5 μm, 10 μm, 15 μm, 20 μm, 25 μm, 30 μm, 35 μm, 40 μm, 4 5μm, 50 μm, 55 μm, 60 μm, 65 μm, 70 μm, 75 μm, 80 μm, 85 μm, 90 μm, 95 μm, 100 μm, 110 μm, 120 μm, 130 μm, 140 μm, 150 μm, 160 μm, 170 μm, 180 μm, 190 μm, 200 μm, 250 μm, 300 μm, 400 μm, 500 μm, 600 μm, 700 μm, 800 μm, 900 μm, 1,000 μm, or more micrometers. A well may have a dimension of x by y by z, where x, y, and z are each independently at most about 1,000 μm, 900 μm, 800 μm, 700 μm, 600 μm, 500 μm, 400 μm, 300 μm, 250 μm, 200 μm, 190 μm, 180 μm, 170 μm, 160 μm, 150 μm, 140 μm, 130 μm, 120 μm, 110 μm, 100 μm, 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 10 μm, 5 μm, 1 μm, 0.1 μm, or less micrometers. For example, a well can have an x dimension of 434 μm, a y dimension of 30 μm, and a z dimension of 510 μm. In another example, a well can have an x and y dimension of 16 μm and a z dimension of 1 μm. The planar surface may be a well among a plurality of wells. The plurality of wells may comprise at least two wells. The plurality of wells may comprise at least 1,000 wells. There may be 2, 3, 4, 5, 6, 7, 8, 9, 10, 15, 20, 25, 30, 35, 40, 45, 50, 60, 70, 80, 90, 100, 200, 300, 400, 500, 1000, 1500, 2000, 3000, 4000, 5000, 10,000, 100,000, 1,000,000 or more than 1,000,000 wells in a plurality of wells. A well may comprise a bead or a planar surface may incorporate a bead. A cfNA fragment may comprise any non-encapsulated polymeric form of nucleotides of any length (e.g., at least 2, 3, 4, 5, 6, 7, 8, 9, 10, 100, 500, 1000 or more nucleotides), either cell-free deoxyribonucleotides (cfDNA) or cell-free ribonucleotides (cfRNA), or analogs thereof.

Analyzing the cfNA fragments that hybridize to a first oligonucleotide bait and a second oligonucleotide bait may comprise measuring an amount of cfNA fragments that hybridize to a first oligonucleotide bait and an amount of cfNA fragments that hybridize to a second oligonucleotide bait may comprise analyzing sizes of the cfNA fragments. Analyzing the size and abundance of cfNA fragments may allow for the targeted investigation of specific cfNA fragments associated with a cell type or function of disease of interest. Fragment abundance may be quantified using a method such as real-time polymerase chain reaction (rtPCR) or quantitative polymerase chain reaction (qPCR). Nucleic acid amplification may be performed using a custom protocol or device or a commercial PCR instrument. A commercial PCR instrument may comprise a combination PCR thermal cycler and fluorescence reader and may be available from commercial vendors such as Agilent (Mx3000P qPCR System), Bio-Rad Laboratories (e.g., CFX96 Touch™M Real-Time PCR Detection System), Illumina® (Eco Real-Time PCR System), Life Technologies (c.g., QuantStudioTM 12K Flex System), Qiagen® (Rotor-Gene Q), Roche Applied Science (LightCycler® systems), or Thermo Scientific (the PikoReal™ Real-Time PCR System), among others. Amplified cfNA fragments may be quantified with a platform such as a NanoDrop™M which measures UV absorbance or QubitTM fluorometer, a DNA quantification device based on the fluorescence intensity of fluorescent dye binding to double-stranded DNA (dsDNA). Quantification of bait pools may be done en masse using microarrays. Fragment size may be quantified using a method such as gel electrophoresis using either a custom device and protocol or a commercial system, commercial capillary electrophoresis, microfluidic separation of cfNA fragments, modified flow cytometry such as DNA fragment sizing based on intercalating dyes which may show a constant ratio of base pairs per dye molecule resulting in the fluorescence of a single DNA fragment being proportional to the fragment length, or a fully integrated microfluidic instrument that may directly count and size single NA fragments in flow with integrated sample volume measurement for concentration determination. Analyzing sizes of cfNA fragments may also comprise sequencing the cfNA fragments and performing alignment-free sequence comparison of cfNA fragment nucleotide sequences to a local reference. In quantifying sizes of cfNA fragments, cfNA fragment mobilities may be compared to a known standard. Analyzing the sizes of cfNA fragments may comprise stretching the cfNA fragments and acquiring an image of the cfNA fragments. Stretching cfNA fragments may comprise capturing an end of a cfNA fragment using a method such as an optical trap or flow-stretching a cfNA fragment. An integrated microfluidic instrument may provide a multiplexed solution for quantifying both abundance as well as fragment size. Such an instrument may include a multiplex PCR amplification in a microfluidic chip. Such a device can be based on the hybridization of a custom bait to circulating NAs immobilized on a membrane and subsequent chemiluminescent or colorimetric detection. In solution, hybridization of the custom bait may trigger enzymatic reactions resulting in the production of light that can be measured using a luminometer.

Analyzing sizes of cfNA fragments may comprise analyzing the sizes of cfDNA by contacting cfDNA fragments with a dye, separating cfDNA fragments into droplets, flowing droplets past a detector, measuring fluorescence of each cfDNA fragment, and inferring fragment size from the fluorescence intensity, wherein fluorescence of the dye may be enhanced by contact with the cfDNA fragments. A fluorescent dye may comprise green fluorescent protein, fluorescein isothiocyanate, fluorescein, tetramethylrhodamine-5- and 6)-isothiocyanate, rhodamine, cyanine, AlexaFluor, DAPI, Hoechst, propidium iodide, acridine orange, or tetramethylrosamine.

cfDNA droplets may vary in size. Droplets may be at least about 0.5 micrometers (μm), 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80, μm, 90 μm, 100 μm, 150 μm, 200 μm, 250 μm, 300 μm, 350 μm, 400 μm, 450 μm, 500 μm, 600 μm, 700 uμ, 800 μm, 900 μm, 1000 μm or more in diameter. They may be less than or greater than these diameters or any value in between. cfDNA, droplet, or solution formation frequency may be at least about 0.5 Hertz (Hz), 1 Hz, 2 Hz, 3 Hz, 4 Hz, 5 Hz, 6 Hz, 7 Hz, 8 Hz, 9 Hz, 10 Hz, 20 Hz, 30 Hz, 40 Hz, 50 Hz, 60 Hz, 70 Hz, 80 Hz, 90 Hz, 100 Hz, 200 Hz, 300 Hz, 400 Hz, 500 Hz, 600 Hz, 700 Hz, 800 Hz, 900 Hz, 1,000 Hz, 2,000 Hz, 3,000 Hz, 4,000 Hz, 5,000 Hz, 6,000 Hz, 7,000 Hz, 8,000 Hz, 9,000 Hz, 10,000 Hz or more. The frequency may be less than or greater than those listed here or any value in between.

A solution comprising the cfDNA molecules may be flowed past a detector at a flow rate about 1 microliter (μL)/minute (min) to about 12 μL/min. The solution comprising the cfDNA molecules may be flowed past a detector at a flow rate about 1 μL/min to about 2 μL/min, about 1 μL/min to about 3 μL/min, about 1 μL/min to about 4 μL/min, about 1 μL/min to about 5 L/min, about 1 μL/min to about 6 μL/min, about 1 μL/min to about 7 μL/min, about 1 μL/min to about 8 μL/min, about 1 μL/min to about 9 μL/min, about 1 μL/min to about 10 μL/min, about 1 μL/min to about 11 μL/min, about 1 L/min to about 12 μL/min, about 2 μL/min to about 3 μL/min, about 2 μL/min to about 4 μL/min, about 2 μL/min to about 5 μL/min, about 2 μL/min to about 6 L/min, about 2 μL/min to about 7 μL/min, about 2 μL/min to about 8 μL/min, about 2 μL/min to about 9 μL/min, about 2 L/min to about 10 μL/min, about 2 μL/min to about 11 μL/min, about 2 μL/min to about 12 μL/min, about 3 μL/min to about 4 μL/min, about 3 μL/min to about 5 L/min, about 3 μL/min to about 6 μL/min, about 3 μL/min to about 7 μL/min, about 3 μL/min to about 8 μL/min, about 3 μL/min to about 9 μL/min, about 3 μL/min to about 10 μL/min, about 3 μL/min to about 11 μL/min, about 3 μL/min to about 12 μL/min, about 4 μL/min to about 5 L/min, about 4 μL/min to about 6 μL/min, about 4 μL/min to about 7 L/min, about 4 μL/min to about 8 μL/min, about 4 μL/min to about 9 μL/min, about 4 μL/min to about 10 μL/min, about 4 μL/min to about 11 L/min, about 4 μL/min to about 12 μL/min, about 5 μL/min to about 6 μL/min, about 5 μL/min to about 7 μL/min, about 5 μL/min to about 8 μL/min, about 5 L/min to about 9 μL/min, about 5 μL/min to about 10 μL/min, about 5 L/min to about 11 μL/min, about 5 μL/min to about 12 μL/min, about 6 μL/min to about 7 μL/min, about 6 μL/min to about 8 μL/min, about 6 μL/min to about 9 μL/min, about 6 μL/min to about 10 μL/min, about 6 L/min to about 11 L/min, about 6 μL/min to about 12 μL/min, about 7 μL/min to about 8 μL/min, about 7 μL/min to about 9 μL/min, about 7 μL/min to about 10 L/min, about 7 μL/min to about 11 μL/min, about 7 L/min to about 12 μL/min, about 8 μL/min to about 9 μL/min, about 8 μL/min to about 10 μL/min, about 8 μL/min to about 11 μL/min, about 8 μL/min to about 12 μL/min, about 9 μL/min to about 10 μL/min, about 9 μL/min to about 11 μL/min, about 9 μL/min to about 12 L/min, about 10 μL/min to about 11 μL/min, about 10 μL/min to about 12 μL/min, or about 11 μL/min to about 12 μL/min. The solution comprising the cfDNA molecules may be flowed at about 1 μL/min, about 2 μL/min, about 3 μL/min, about 4 μL/min, about 5 μL/min, about 6 μL/min, about 7 μL/min, about 8 L/min, about 9 μL/min, about 10 μL/min, about 11 μL/min, or about 12 μL/min. The solution comprising the cfDNA molecules may be flowed past a detector at least about 1 L/min, about 2 μL/min, about 3 μL/min, about 4 μL/min, about 5 μL/min, about 6 μL/min, about 7 L/min, about 8 μL/min, about 9 μL/min, about 10 μL/min, or about 11 μL/min. The solution comprising the polypeptide molecules may be flowed past a detector at most about 2 μL/min, about 3 μL/min, about 4 μL/min, about 5 μL/min, about 6 μL/min, about 7 μL/min, about 8 μL/min, about 9 μL/min, about 10 μL/min, about 11 μL/min, or about 12 μL/min.

Analyzing a cfNA fragment that hybridize to a first oligonucleotide bait and a second oligonucleotide bait may comprise analyzing sizes of cfNA fragments. Analyzing sizes of cfNA fragments may comprise comparing an amount of large cfNA fragments comprising at least 230 nucleotides to an amount of small cfNA fragments comprising less than 230 nucleotides. A large cfNA fragment may comprise at least 185, 255, 270, or 310 nucleotides. A large fragment may comprise about, 50, 55, 60, 65, 70, 75, 80, 85, 90, 100, 150, 200, 250, 300, 350, 400, 450, 500, 600, 700, 800, 900, 1000, or more than 1000 base pairs. A large fragment may comprise about 1000, 900, 800, 700, 600, 500, 450, 400, 350, 300, 250, 200, 150, 100, 90, 80, 70, 60, 50, or less than 50 base pairs. A small cfNA fragment may comprise less than 220, 205, 190, or 175 nucleotides. A small fragment may comprise about 1, 2, 3, 4, 5, 6, 7, 8, 9, 10, 11, 12, 13, 14, 15, 20. 25. 30, 35, 40, 45, 50, 60, 70, 80, 90, 100, 150, 200, 230, or more than 230 base pairs. A small fragment may comprise about less than 230, 200, 150, 100, 90, 80, 70, 60, 50, 45, 40, 35, 30, 25, 20, 15, 10, 9, 8, 7, 6, 5, 4, 3, 2, or 1 base pair. A small cfNA fragment may comprise less than 220, 205, 190, or 175 nucleotides. An increased abundance of large cfNA fragments may be indicative of a medical condition. A ratio of large cfNA fragments to small cfNA fragments of at least 0.2, 0.25, 0.3, 0.35 or 0.4 may be indicative of a medical condition. A ratio of large cfNA fragments to small cfNA fragments may be at least 0.1, 0.15, 0.2, 0.25, 0.3, 0.35, 0.4, 0.45, 0.5, 0.6, 0.7, 0.8, 0.9, or 1 and may be indicative of a medical condition. A ratio of large cfNA to small cfNA fragments may be less than 1, 0.9, 0.8, 0.7, 0.6, 0.5, 0.45, 0.4, 0.35, 0.3, 0.25, 0.2, 0.15, 0.1, or less than 0.1.

Analyzing cfNA fragments that hybridize to a first oligonucleotide bait and a second oligonucleotide bait may comprise sequencing cfNA fragments and performing alignment-free sequence comparison of the cfNA fragment nucleotide sequences to a local reference. Characterizing cfNA fragments derived from a genomic region, may comprise contacting a composition comprising cfNA with an oligonucleotide bait, and sequencing cfNA fragments that hybridize to the oligonucleotide bait and identifying two or more subregions within the genomic region counting a number of cfNA fragments matching each subregion, wherein the oligonucleotide bait may comprise a sequence complementary to a sequence of the genomic region. Quantifying a relative amount of cfNA fragment sequences may comprise aligning to sequences distal to a first end of the first oligonucleotide bait versus cfNA fragment sequences aligning to sequences distal to a second end of the first oligonucleotide bait. Quantifying a relative amount of cfNA fragment sequences may comprise aligning to sequences distal to a first end of the second oligonucleotide bait versus cfNA fragment sequences aligning to sequences distal to a second end of the second oligonucleotide bait.

Aspects of the present disclosure may comprise a method of characterizing cfNA fragments derived from a genomic region, comprising: collecting a first set of cfNA fragments from a biological sample by hybridization capture with a first oligonucleotide bait comprising a sequence complementary to a first sequence of the genomic region; collecting a second set of cfNA fragments from a biological sample by hybridization capture with a second oligonucleotide bait comprising a sequence complementary to a second sequence of the genomic region; and comparing the first set of cfNA fragments and second set of cfNA fragments, wherein characterizing the fragmentation pattern does not comprise identifying genomic locations or lengths of the first set of cfNA fragments or the second set of cfNA fragments. A first oligonucleotide bait and a second oligonucleotide bait may be conjugated to an affinity tag wherein the affinity tag may comprise biotin. A first oligonucleotide bait and a second oligonucleotide bait may be conjugated to a solid surface, A solid surface may. comprise a bead. A solid surface may comprise a planar surface. A cfNA fragment may comprise any non-encapsulated polymeric form of nucleotides of any length (e.g., at least 2, 3, 4, 5, 6, 7, 8, 9, 10, 100, 500, 1000 or more nucleotides), either cell-free deoxyribonucleotides (cfDNA) or cell-free ribonucleotides (cfRNA), or analogs thereof. Characterizing the fragmentation pattern of cfNA fragments may comprise analyzing sizes or abundances of cfNA fragments.

Each set of molecular function-specific oligonucleotides may facilitate isolation of a different fragmentation pattern associated with a target pathology. Each solid surface may be provided with a binding partner specific to one immobilization tag present on only one set of molecular function-specific or pathology-specific oligonucleotides. Thus, through binding of each different immobilization tag to a specific binding partner the different genomes of interest can be isolated onto different solid surfaces. For example, if a first pathogenic genome of interest is isolated onto a set of magnetic beads and a second pathogenic genome of interest is isolated onto a set of polystyrene or glass beads, a simple magnetic separation can remove the magnetic beads from the polystyrene or glass beads thereby isolating two different pathogenic genomes. It may be possible to isolate multiple different targets on the same solid surface and subsequently utilize sequencing and mapping protocols to separate and identify the different targets.

With multiple pools of enriched nucleic acids, functional typing of these enriched nucleic acids may be performed using functional allele information. Every cell, healthy or with a pathological condition, may carry a specific molecular signature associated an organ role or function. While distinct tissues and cell types may look and operate differently, they may all be derived from the same DNA sequence. A molecular signature of a cell may be governed by chromatin organization and transcriptional regulation. While DNA itself may remain the same throughout distinct cell types, the organization of DNA in the nucleus may vary due to nucleosomal organization. Each cell type, including those of specific pathologies such as cancers, may have an individual chromatin code defining a nucleosomal location and spacing which may govern gene expression. During cell death, the chromatin code may undergo a change that may maintain some cell type and function signatures while breaking others. DNA fragmentation may take place: : irrespective of cell death type via macrophage lysosomal DNaseII as opposed to caspase-activated DNase in apoptosis. These signatures may be traced in cfNA from blood as some cfNA from dead cells may evade or escape phagocytosis and enter the bloodstream resulting in cfNAs present in plasma.

Aspects of the present disclosure may comprise a method of characterizing cfNA fragments derived from a genomic region, comprising collecting a first set of cfNA fragments from a biological sample by hybridization capture with a first oligonucleotide bait comprising a sequence complementary to a first sequence of the genomic region; collecting a second set of cfNA fragments from a biological sample by hybridization capture with a second oligonucleotide bait comprising a sequence complementary to a second sequence of the genomic region; and analyzing the abundance of the first set of cfNA fragments and the second set of cfNA fragments wherein analyzing abundance of the cfNA fragments may comprise sequencing the cfNA fragments and performing alignment-free sequence comparison of the cfNA fragment nucleotide sequences to a local reference. Hybridization capture may allow for the efficient exploitation of current high-throughput sequencing and larger data sets to be generated for multiple target loci as well as for multiple samples in parallel. In hybridization capture a bait molecule may be used to select target regions from nucleic acid libraries for sequencing. An increased abundance of cfNA fragments may be indicative of a medical condition. Fragment abundance may be quantified using a method such as real-time polymerase chain reaction (rtPCR) or quantitative polymerase chain reaction (qPCR). An integrated microfluidic instrument may provide a multiplexed solution for quantifying both abundance as well as fragment size. Analyzing cfDNA size or abundance may comprise a variety of methods such as measuring the optical density of a DNA solution at a wavelength of 260 nm using a spectrophotometer or may comprise gel electrophoresis that separates DNA fragments and subsequently quantify band fluorescence from intercalating dyes to direct quantification of fluorescence from solutions containing DNA and intercalating dyes.

Aspects of the present disclosure may comprise a method of characterizing cfNA fragments derived from a genomic region, comprising: collecting a first set of cfNA fragments from a biological sample by hybridization capture with a first oligonucleotide bait comprising a sequence complementary to a first sequence of the genomic region; collecting a second set of cfNA fragments from a biological sample by hybridization capture with a second oligonucleotide bait comprising a sequence complementary to a second sequence of the genomic region; and analyzing sizes of the first set of cfNA fragments and the second set of cfNA fragments. Analyzing the sizes of cfNA may comprise an electrophoretic separation wherein an electrophoretic separation may comprise gel or capillary electrophoresis. Electrophoretic separation may comprise microfluidic separation of cfNA fragments. Analyzing fragment size of cfNAs may comprise comparing mobilities of cfNA fragments to a known standard. A known standard may be provided from a custom reference library such as one based on clinical or empirical data or may be a commercially available molecular weight reference set. Analyzing the sizes of cfNA fragments, may comprise stretching cfNA fragments and acquiring an image of the cfNA fragments.

Analyzing the sizes of cfNA fragments may comprise capturing an end of a cfNA fragment in an optical trap or flow-stretching a cfNA fragments. Analyzing the sizes of cfNA fragments may comprise contacting the cfNA fragments with a dye, separating the cfNA fragments into droplets, flowing the droplets past a detector, measuring the fluorescence of each cfNA fragment, and calculating a size from the fluorescence intensity, wherein fluorescence of the dye is enhanced by contact with the cfNA fragments.

Analyzing sizes of cfNA fragments may comprise comparing an amount of large cfNA fragments comprising at least 230 nucleotides to an amount of small cfNA fragments comprising less than 230 nucleotides for the first set of cfNA fragments and comparing an amount of large cfNA fragments comprising at least 230 nucleotides to an amount of small cfNA fragments comprising less than 230 nucleotides for the second set of cfNA fragments. A large cfNA fragment may comprise at least 185, 255, 270, or 310 nucleotides. A large fragment may comprise about, 50, 55, 60, 65, 70, 75, 80, 85, 90, 100, 150, 200, 250, 300, 350, 400, 450, 500, 600, 700, 800, 900, 1000, or more than 1000 base pairs. A large fragment may comprise about 1000, 900, 800, 700, 600, 500, 450, 400, 350, 300, 250, 200, 150, 100, 90, 80, 70, 60, 50, or less than 50 base pairs. A small cfNA fragment may comprise less than 220, 205, 190, or 175 nucleotides. A small fragment may comprise about 1, 2, 3, 4, 5, 6, 7, 8, 9, 10, 11, 12, 13, 14, 15, 20. 25. 30, 35, 40, 45, 50, 60, 70, 80, 90, 100, 150, 200, 230, or more than 230 base pairs. A small fragment may comprise about less than 230, 200, 150, 100, 90, 80, 70, 60, 50, 45, 40, 35, 30, 25, 20, 15, 10, 9, 8, 7, 6, 5, 4, 3, 2, or 1 base pair. A small cfNA fragment may comprise less than 220, 205, 190, or 175 nucleotides. An increased abundance of large cfNA fragments in the first set of cfNA fragments may be indicative of a medical condition. A ratio of large cfNA fragments to small cfNA fragments of at least 0.2, 0.25, 0.3, 0.35 or 0.4 in the first set of cfNA fragments may be indicative of a medical condition. A ratio of large cfNA fragments to small cfNA fragments in the first set of cfNA fragments may be at least 0.1, 0.15, 0.2, 0.25, 0.3, 0.35, 0.4, 0.45, 0.5, 0.6, 0.7, 0.8, 0.9, or 1 and may be indicative of a medical condition. A ratio of large cfNA to small cfNA fragments in the first set of cfNA fragments may be less than 1, 0.9, 0.8, 0.7, 0.6, 0.5, 0.45, 0.4, 0.35, 0.3, 0.25, 0.2, 0.15, 0.1, or less than 0.1 and may be indicative of a medical condition.

Aspects of the present disclosure may comprise a method of characterizing cfNA fragments derived from a genomic region, comprising: collecting a first set of cfNA fragments from a biological sample by hybridization capture with a first oligonucleotide bait comprising a sequence complementary to a first sequence of the genomic region; collecting a second set of cfNA fragments from a biological sample by hybridization capture with a second oligonucleotide bait comprising a sequence complementary to a second sequence of the genomic region; sequencing the first set of cfNA fragments and the second set of cfNA fragments; and performing alignment-free sequence comparison of the cfNA fragment nucleotide sequences to a local reference sequence. Quantifying a relative amount of cfNA fragments derived from a genomic region may comprise collecting a first set of cfNA fragments from a biological sample by hybridization capture with a first oligonucleotide bait comprising a sequence complementary to a first sequence of the genomic region; collecting a second set of cfNA fragments from a biological sample by hybridization capture with a second oligonucleotide bait comprising a sequence complementary to a second sequence of the genomic region; sequencing the first set of cfNA fragments and the second set of cfNA fragments; identifying two or more subregions within the genomic region; and counting a number of cfNA fragments matching each subregion. A cfNA fragment may match a subregion if a sequence of the fragment is identical to the sequence of the subregion, or a sequence of the fragment is assigned to the subregion via approximate string matching or a similar method such as Levenshtein distance, BK-Trees, or a Norvig approach.

Aspects of the present disclosure may comprise a method of characterizing cfNA fragments derived from a genomic region, comprising comparing an amount of cfNA fragments that comprise a first portion of the genomic region with an amount of the cfNA fragments that comprise a second portion of the genomic region. Multiple cfNA fragments may be analyzed from the same genomic region or from overlapping genomic regions. Amounts of cfNA fragments may comprise the first portion and the second portion of the genomic region may be determined by a method comprising amplification of the portions of the genomic region. Amplification may be performed using a variety of techniques such as a custom protocol or device or a commercial PCR instrument. A commercial PCR instrument may comprise a combination PCR thermal cycler and fluorescence reader and may be available from commercial vendors such as Agilent (Mx3000P qPCR System), Bio-Rad Laboratories (e.g., CFX96 Touch™ Real-Time PCR Detection System), Illumina® (Eco Real-Time PCR System), Life Technologies (e.g., QuantStudio™ 12K Flex System), Qiagen® (Rotor-Gene Q), Roche Applied Science (LightCycler® systems), or Thermo Scientific (the PikoReal™ Real-Time PCR System), among others. Amplified cfNA fragments may be quantified with a platform such as a NanoDrop™ which measures UV absorbance, Qubit™ fluorometer, a DNA quantification device based on the fluorescence intensity of fluorescent dye binding to double-stranded DNA (dsDNA), or a method such as loop-mediated isothermal amplification. Nucleic acid sequence-based amplification, strand displacement amplification, or multiple displacement amplification.

A composition comprising cfNA may comprise or include blood (e.g., whole blood), plasma, serum, umbilical cord blood, chorionic villi, amniotic fluid, lavage fluid (e.g., bronchoalveolar, gastric, peritoneal, ductal, ear, arthroscopic), tracheobronchial lavage, biopsy sample (e.g., from pre-implantation embryo), celocentesis sample, fetal nucleated cells or fetal cellular remnants, bile, breast milk, urine, saliva, mucosal excretions, sputum, stool, sweat, vaginal fluid, fluid from a hydrocele (e.g., of the testis), vaginal flushing fluids, pleural fluid, ascitic fluid, amniotic fluid, peritoneal fluid, ascitic fluid, abdominopelvic washings/lavage, serous effusions, cerebrospinal fluid, bronchoalveolar lavage fluid, discharge fluid from the nipple, aspiration fluid from different parts of the body (e.g., thyroid, breast), tears, embryonic cells, or fetal cells (e.g., placental cells).

A genomic region may comprise a first exon and/or subsequent exon(s). A genomic region may comprise an active transcriptional start site, at least one nucleotide of a promotor, a transcriptional start site, a DNase I-hypersensitive site, a Pol II pausing site, an intron to exon boundary, or untranslated regions. Expression or post-death fragmentation of the genomic region may be altered in a medical condition. Aspects of the present disclosure may comprise a method of analyzing a cfNA fragmentation pattern comprising characterizing cfNA fragments derived from one, two, or more than two genomic regions.

In some embodiments, a cfNA fragment may be derived from a genomic region indirectly. For example, the number of copies of the HER2 gene is expanded in some breast cancer tumors by the formation of double minute (DM) chromosomes. In these tumors, the HER2 genomic region on the DM chromosome is derived from the HER2 genomic region on chromosome 17. A cfNA fragment derived from the HER2 locus of a DM chromosome could have the same sequence as a cfNA fragment derived from the HER2 locus of chromosome 17 and would align to the HER2 locus on chromosome 17 because the cfNA fragment is derived from the chromosome 17 locus indirectly. In another embodiment, the cfNA fragment is a cfRNA fragment that is derived indirectly from a genomic region by transcription and RNA processing.

A genomic region may comprise a start site or first exon of a specific physiologically relevant or pathologically relevant condition such as the first exon of a steroid responsive gene. Developing biomarkers from such genomic regions may allow the tracking of pharmacokinetics or bioavailability of administered drug that would allow for the monitoring of the magnitude of a response to treatment, dose optimization, or treatment selection. For example, the start site or first exon of a steroid response gene may be used to determine the magnitude of the immune response to a treatment with glucocorticoid. The start site or first exon of a gene with a molecular function associated with vascularization or angiogenesis may be used to determine the response of a malignant tumor to treatment with a chemotherapy. As can be seen in Table 1, a molecular function such as a steroid signature, vascular marker, or angiogenesis may be associated with a molecular pathway such as vessel stability or endothelial cell marker genes through a variety of genes that may be linked to the molecular pathway or function. These features may be traced to a specific chromosome, nucleotide sequence, position, or strand.

TABLE 1

Target genomic regions and keywords for molecular functions associated with steroid treatment response and tumor response to treatment.

| Signature | Molecular Pathway | Gene | Features | chr | Start | End of exon 1 | Strand |
|---|---|---|---|---|---|---|---|
| Steroid signature | Glucocorticoid signature | FKBP5 | 1st exon, all exons, enhancers, locations of promoter-proximal pausing and/or any combination of those | chr6 | 35656509 | 35656692 | − |
| | | ECHDC3 | 2nd exon, all exons, enhancers, locations of promoter-proximal pausing and/or any combination of those | chr10 | 11784365 | 11784745 | + |
| | | IL1R2 | 3rd exon, all exons, enhancers, locations of promoter-proximal pausing and/or any combination of those | chr2 | 102608306 | 102608473 | + |
| | | ZBTB16 | 4th exon, all exons, enhancers, locations of promoter-proximal pausing and/or any combination of those | chr11 | 113930315 | 113930604 | + |
| | Anti-inflammatory signature | DUSP1 | 5th exon, all exons, enhancers, locations of promoter-proximal pausing and/or any combination of those | chr5 | 172197589 | 172198198 | − |
| | | TSC22D3 | 6th exon, all exons, enhancers, locations of promoter-proximal pausing and/or any combination of those | chrX | 106959545 | 106959775 | − |
| | | IRAK3 | 7th exon, all exons, enhancers, locations of promoter-proximal pausing and/or any combination of those | chr12 | 66582659 | 66583212 | + |
| | | CD163 | 8th exon, all exons, enhancers, locations of promoter-proximal pausing and/or any combination of those | chr12 | 7656241 | 7656489 | − |
| | Neutrophil activation signature (anti-apoptotic Mcl-1 pathway) | BCL2 | 9th exon, all exons, enhancers, locations of promoter-proximal pausing and/or any combination of those | chr18 | 60985315 | 60987361 | − |
| | | MCL1 | 10th exon, all exons, enhancers, locations of promoter-proximal pausing and/or any combination of those | chr1 | 150551899 | 150552214 | − |
| Vascular markers | Endothelial cell marker genes | PECAM1 | 10th exon, all exons, enhancers, locations of promoter-proximal pausing and/or any combination of those | chr17 | 62,396,775 | 62,404,856 | − |
| | | CDH5 | 10th exon, all exons, enhancers, locations of promoter-proximal pausing and/or any combination of those | chr16 | 66,400,525 | 66,438,689 | + |
| | | VWF | 10th exon, all exons, enhancers, locations of promoter-proximal pausing and/or any combination of those | chr12 | 6,058,040 | 6,233,936 | − |
| | | EPHB4 | 10th exon, all exons, enhancers, locations of promoter-proximal pausing and/or any combination of those | chr7 | 100,400,187 | 100,425,143 | − |
| | Pericyte marker gene | CSPG4 | 10th exon, all exons, enhancers, locations of promoter-proximal pausing and/or any combination of those | chr15 | 75,966,663 | 76,005,189 | − |
| | | ACTA2 | 10th exon, all exons, enhancers, locations of promoter-proximal pausing and/or any combination of those | chr10 | 90,694,831 | 90,751,147 | + |
| | | DES | 10th exon, all exons, enhancers, locations of promoter-proximal pausing and/or any combination of those | chr2 | 220,283,099 | 220,291,461 | + |
| | Integrins | ITGAV | 10th exon, all exons, enhancers, locations of promoter-proximal pausing and/or any combination of those | chr2 | 187,454,790 | 187,545,628 | + |
| | | ITGB3 | 10th exon, all exons, enhancers, locations of promoter-proximal pausing and/or any combination of those | chr17 | 45,331,208 | 45,421,658 | + |
| Angiogenesis | Angiogenesis, vessel de-stabilization | HIF1AN | 10th exon, all exons, enhancers, locations of promoter-proximal pausing and/or any combination of those | chr10 | 102,288,829 | 102,319,755 | + |
| | | VEGFA | 10th exon, all exons, enhancers, locations of promoter-proximal pausing and/or any combination of those | chr6 | 43,737,921 | 43,754,224 | − |
| | | PGF | 10th exon, all exons, enhancers, locations of promoter-proximal pausing and/or any combination of those | chr14 | 75,408,533 | 75,422,487 | − |
| | | FLT1 | 10th exon, all exons, enhancers, locations of promoter-proximal pausing and/or any combination of those | chr13 | 23,874,483 | 29,069,265 | − |
| | | KDR | 10th exon, all exons, enhancers, locations of promoter-proximal pausing and/or any combination of those | chr4 | 55,944,426 | 55,991,762 | + |
| | | NR4A1 | 10th exon, all exons, enhancers, locations of promoter-proximal pausing and/or any combination of those | chr12 | 52,416,616 | 52,453,291 | + |
| | | FGF2 | 10th exon, all exons, enhancers, locations of promoter-proximal pausing and/or any combination of those | chr4 | 123,747,863 | 123,819,391 | − |
| | | FGFR1 | 10th exon, all exons, enhancers, locations of promoter-proximal pausing and/or any combination of those | chr8 | 38,268,656 | 38,326,352 | − |
| | | FGFR2 | 10th exon, all exons, enhancers, locations of promoter-proximal pausing and/or any combination of those | chr10 | 123,237,844 | 123,357,972 | − |

TABLE 1-continued

Target genomic regions and keywords for molecular functions associated with steroid treatment response and tumor response to treatment.

| Signature | Molecular Pathway | Gene | Features | chr | Start | End of exon 1 | Strand |
|---|---|---|---|---|---|---|---|
| | Vessel stability | ANGPT1 | 10th exon, all exons, enhancers, locations of promoter-proximal pausing and/or any combination of those | chr8 | 108,261,710 | 108,510,283 | − |
| | | ANGPT2 | 10th exon, all exons, enhancers, locations of promoter-proximal pausing and/or any combination of those | chr8 | 6,357,172 | 6,420,930 | + |
| | | TEK | 10th exon, all exons, enhancers, locations of promoter-proximal pausing and/or any combination of those | chr9 | 27,109,139 | 27,290,173 | − |
| | | PDGFB | 10th exon, all exons, enhancers, locations of promoter-proximal pausing and/or any combination of those | chr22 | 39,619,364 | 39,640,957 | − |
| | | PDGFRB | 10th exon, all exons, enhancers, locations of promoter-proximal pausing and/or any combination of those | chr5 | 149,493,400 | 149,535,435 | − |
| | | TGFB1 | 10th exon, all exons, enhancers, locations of promoter-proximal pausing and/or any combination of those | chr19 | 41,807,492 | 41,859,831 | + |
| | | TGFBR1 | 10th exon, all exons, enhancers, locations of promoter-proximal pausing and/or any combination of those | chr9 | 101,866,320 | 101,916,474 | − |
| | | ENG | 10th exon, all exons, enhancers, locations of promoter-proximal pausing and/or any combination of those | chr9 | 130,577,291 | 130,617,047 | − |
| | Vascular morphogenesis/ Notch family | NOTCH1 | 10th exon, all exons, enhancers, locations of promoter-proximal pausing and/or any combination of those | chr9 | 139,388,896 | 139,440,314 | − |
| | | NOTCH3 | 10th exon, all exons, enhancers, locations of promoter-proximal pausing and/or any combination of those | chr19 | 15,270,444 | 15,311,792 | + |
| | | DLL4 | 10th exon, all exons, enhancers, locations of promoter-proximal pausing and/or any combination of those | chr15 | 41,221,531 | 41,231,258 | − |
| | | JAG1 | 10th exon, all exons, enhancers, locations of promoter-proximal pausing and/or any combination of those | chr20 | 10,618,332 | 10,654,694 | |

Table 1: Target genomic regions and keywords for molecular functions associated with steroid treatment response and tumor response to treatment.

A steroid responsive gene may comprise a glucocorticoid responsive gene, an anti-inflammatory gene, or a neutrophil activation signature gene. A glucocorticoid responsive gene may comprise FKBP5, ECHDC3, ILIR2 or ZBTB16 among others. An anti-inflammatory gene may comprise DUSP1, TSC22D3, IRAK3, or CD163 among others. A neutrophil activation signature gene may comprise BCL2 or MCL1 among others. A genomic region may comprise but is not limited to a start site or first exon of a vascular marker gene, endothelial cell marker gene, or an angiogenesis gene. A vascular marker gene may comprise an endothelial cell marker gene, or a pericyte marker gene among others. An endothelial cell marker gene may comprise but is not limited to PECAM1, CDH5, VWF, or EPHB4. A pericyte marker gene may comprise but is not limited to CSPG4, ACTA2, or DES. An integrin gene may comprise but is not limited to ITGAV or ITGB3. An angiogenesis gene may comprise but is not limited to a vessel destability gene, a vessel stability gene, or a notch family gene. A vessel destability gene may comprise but is not limited to HIF1AN, VEGFA, PGF, FLT1, KDR, NR4A1, FGF2, FGFR1, or FGFR2. A vessel stability gene may.: comprise but is not limited to ANGPT1, ANGPT2, TEK, PDGFB, PDGFRB, TGFB1, TGFBR1, or ENG. In some cases, the notch family gene is NOTCH1, NOTCH3, DLL4, or JAG1. A genomic region may be selected from but is not limited to the first 5 exons of an EphB4 gene.

Aspects of the present disclosure may comprise a method of evaluating a medical condition in a subject comprising characterizing a fragmentation pattern of cfNA fragments derived from a genomic region. Characterizing a fragmentation pattern of cfNA fragments derived from a genomic region may include non-invasive tests for detecting and monitoring presence and progression of one or a plurality of physiological or pathological conditions. Interplays of dysregulated cell death between altered epigenetic regulation, genomic regulation, and production of autoimmune antibodies in a given disease may cause abnormal patterns of circulating NAs such as cfDNAs. Customized enrichment panels or optimal assay conditions to delineate biological characteristics of cfNAs in the plasma of a given disease may allow an accurate ability to detect any pathology via a blood draw or similar minimally invasive method. Combinations of molecular assays, targeted panel designs, and bioinformatics pipelines may be associated with design of such methods and downstream interpretation of their results.

Aspects of the present disclosure may comprise a method of adaptive immunotherapy for the treatment of cancer in a subject comprising: administering a first course of a first immunotherapy compound to the subject; acquiring a longitudinal cell-free NA fragmentation profile for one or more genes associated with a cancer-relevant molecular function such as angiogenesis and/or vasculogenesis from the subject; and administering a second course of immunotherapy to the subject; wherein the second course of immunotherapy may comprise a second immunotherapy compound if the cell-free NA fragmentation profile is indicative of an insufficient response to the first immunotherapy compound; or a second course of the first immunotherapy compound if the cell-frec NA fragmentation profile is not indicative of an insufficient response to the first immunotherapy compound. A cancer may comprise but is not limited to cancers such as is lung cancer, melanoma, gastrointestinal carcinoid tumor, colorectal cancer or pancreatic cancer. Acquiring a longitudinal cfNA fragmentation profile for one or more genes associated with a cancer-relevant molecular function may allow for a rapid alteration of treatment from a first line therapy to a second, third, or subsequent therapy which may save time in a treatment course or determine the most effective therapeutic for a subject rapidly. The ability to measure cancer progression or response rate to a therapy may reduce the side effects and costs associated with ineffective therapy. Availability of tumor progression markers may result in improved survival in patients that become available for second line therapy or eligible for second line trials.

An adaptive immunotherapy may comprise any immunotherapy, such as a CAR T-Cell therapy, which may circumvent or mitigate immune tolerance of cancer cells to re-establish anti-tumor immunity. A second and distinct round of immunotherapy or chemotherapy may be utilized after a first course of an immunotherapy or chemotherapy if a cfNA fragmentation profile in a subject does not indicate a sufficient response to the first immunotherapy or chemotherapy compound.

Acquiring a longitudinal cell-free NA fragmentation profile may comprise acquiring a first biological sample from the subject at an initial T0 time-point prior to administering a first dose of the first course of the first immunotherapy compound and acquiring one or more biological samples from the subject after administering the first dose of the first course of the first immunotherapy compound. One or more biological samples may be acquired after administering a first dose of a first course of a first immunotherapy or chemotherapy compound and that acquisition may occur on the same day that a dose of the of the first course of the first immunotherapy compound is administered.

The cell-free NA fragmentation profile may comprise but is not limited to sizes of NA fragments derived from enhancers, promoters, first exons or promoter-proximal transcriptional pause sites of the one or more genes associated with a cancer-relevant molecular function such as but not limited to angiogenesis and/or vasculogenesis. An increase over time of large cell-free NA fragments derived from genomic regions such as but not limited to enhancers, promoters, first exons or promoter-proximal transcriptional pause sites of one or more genes associated with a molecular function relevant to cancer, such as angiogenesis and/or vasculogenesis, may be indicative of an insufficient response to the first immunotherapy or chemotherapy compound. A first immunotherapy or chemotherapy compound and a second immunotherapy or chemotherapy compound may be selected from a group consisting of but not limited to pembrolizumab, nivolumab, atezolizumab, durvalumab, avelumab, axitinib, ipilimumab, altretamine, bendamustine, busulfan, carboplatin, carmustine, chlorambucil, cisplatin, cyclophosphamide, cacarbazine, cfosfamide, lomustine, mechlorethamine, melphalan, oxaliplatin, temozolomide, thiotepa, trabectedin, streptozocin, azacytidine, 5-fluorouracil, 6-mercaptopurine, capecitabine, cladribine, clofarabine, cytarabine, decitabine, floxuridine, fludarabine, gemcitabine, hydroxyurea, methotrexate, nelarabine, pemetrexed, pentostatin, pralatrexate, thioguanine, trifluridine/tipiracil combination, daunorubicin, doxorubicin, epirubicin, idarubicin, valrubicin, bleomycin, dactinomycin, mitomycin-C, mitoxantrone, irinotecan, topotecan, teniposide, etoposide, cabazitaxel, docetaxel, nab-paclitaxel, paclitaxel, vinblastine, vincristine, vinorelbine, arsenic trioxide, asparaginase, eribulin, hydroxyurea, ixabepilone, mitotane, omacctaxine, pegaspargase, procarbazine, romidepsin, or vorinostat.

Aspects of the present disclosure may comprise a method of treating a medical condition in a subject comprising: administering a course of therapy to the subject and acquiring a longitudinal cell-free DNA fragmentation profile for one or more genes from the subject; wherein the longitudinal cell-free DNA fragmentation profile may indicate that the subject has responded to the course of therapy.

Aspects of the present disclosure may comprise a method of treating a medical condition in a subject comprising: acquiring a cell-free NA fragmentation profile for one or more genes from the subject; and administering a course of therapy to the subject, wherein a cell-free NA fragmentation profile indicates that the course of therapy may be indicated for the subject.

Aspects of the present disclosure may comprise a kit which may comprise any combination of but are not limited to diverse reagent kits, instruments, a bioinformatic pipeline, a simple diagnostic kit which may not require laboratory equipment, or a lab-in-a-box custom assay handler system.

Multiple-Bait Systems

The present disclosure provides a multiple-bait system comprising at least two oligonucleotide baits for characterizing cfNA fragments derived from at least two genomic regions. In some aspects, a method of characterizing cfNA fragments derived from at least two genomic regions comprising a first genomic region and a second genomic region is disclosed herein, comprising a) contacting a composition comprising cfNA with a first oligonucleotide bait comprising a sequence complementary to a sequence of the first genomic region, b) contacting the composition with a second oligonucleotide bait comprising a sequence complementary to a sequence of the second genomic region, and c) analyzing abundance, size and sequence context of the cfNA fragments that hybridize to the at least two oligonucleotide baits. In some embodiments, the first oligonucleotide bait enriches a population of short cfNA fragments from the composition and the second oligonucleotide bait enriches a population of long cfNA fragments from the composition. In some embodiments, the method further comprises contacting the composition with a third oligonucleotide bait comprising a sequence complementary to a sequence of the first genomic region. In some embodiments, the third oligonucleotide bait enriches a population of small cfNA fragments from the composition. In some embodiments, the third oligonucleotide bait enriches a population of long cfNA fragments from the composition. In some embodiments, the method further comprises contacting the composition with a fourth oligonucleotide bait comprising a sequence complementary to a sequence of the second genomic region. In some embodiments, the fourth oligonucleotide bait enriches a population of long cfNA fragments from the composition. In some embodiments, step (a) and step (b) occur simultaneously. In some embodiments, the at least two genomic regions further comprises a third genomic region; wherein the method further comprises contacting the composition with a fifth oligonucleotide bait comprising a sequence complementary to a sequence of the third genomic region. In some embodiments, the fifth oligonucleotide bait enriches a population of short cfNA fragments from the composition. In some embodiments, the fifth oligonucleotide bait enriches a population of long cfNA fragments from the composition. In some embodiments, the contacting the composition with the fifth oligonucleotide bait occur simultaneously with step (a) and step (b). In some embodiments, the method further comprises contacting the composition with a sixth oligonucleotide bait comprising a sequence complementary to a sequence of the third genome region. In some embodiments, the sixth oligonucleotide bait enriches a population of long cfNA fragments from the composition. In some embodiments, the sixth oligonucleotide bait enriches a population of short cfNA fragments from the composition. In some embodiments, the contacting the composition with the sixth oligonucleotide bait occur simultaneously with contacting the composition with the fifth oligonucleotide bait, step (a), and step (b). In some embodiments, wherein the analyzing abundance, size and sequence context of the cfNA fragments does not comprise identifying genomic locations or lengths of the cfNA fragments. In some embodiments, the first oligonucleotide bait, the second oligonucleotide bait, the third oligonucleotide bait, the fourth oligonucleotide bait, the fifth oligonucleotide bait, and/or the sixth oligonucleotide bait is conjugated to an affinity tag. In some aspects, the present disclosure provides a method of evaluating a medical condition in a subject comprising characterizing a fragmentation pattern of cfDNA fragments derived from at least two genomic regions according to any of the method disclosed herein.

EXAMPLES

Example 1. Glucocorticoid Treatment Alters the cfDNA Fragmentation Pattern of Glucocorticoid-Responsive Genes Gene expression is mediated by DNA binding proteins (e.g. transcription factors and polymerases) that can protect DNA from cleavage by nucleases, including the nucleases that fragment the DNA of dying cells. Changes in gene expression can alter the fragmentation pattern of cfDNA derived from the promoters and transcriptional start sites of differentially expressed genes.

A healthy female volunteer with previous mild exposure to poison oak was treated with a single dose of 40 mg prednisolone, a common anti-inflammatory drug. A first set of blood samples was obtained prior to prednisolone administration and a second blood sample was obtained 16 hours later (FIG. 1). Blood was collected by venipuncture in a 10 mL EDTA vacutainer and processed within two hours of the blood draw. The blood samples were remixed immediately prior to centrifugation by gently inverting the tube 8 to 10 times. To separate plasma, whole blood was centrifuged at 1600×g for 10 minutes at room temperature. The upper plasma layer was removed and transferred to a new conical tube. The plasma was centrifuged at 16000×g for 10 minutes. Plasma was aliquoted into 1 mL vials as needed and stored at −80° C. to maintain stability and avoid degradation and contamination of DNA. cfDNA was extracted from plasma using a QIAamp Circulating Nucleic Acid kid (Qiagen®, 55114) and the quality of plasma cfDNA was evaluated on a Bioanalyzer 2100 (Agilent Technologies). Four cfDNA sequencing libraries were generated for each timepoint using the Kapa Hyper Prep Kit (Kapa Biosystems). Barcoded libraries were quantified, pooled, and paired-end sequenced using an Illumina® NovaSeq 6000 DNA sequencer. The bioinformatic workflow involved base call generation by Illumina's® RTA software (v2.12), demultiplexing using bcl2fastq and mapping reads to the human reference genome Hg19 using BWA v0.7.1, executed on AWS cloud. Duplicate and low-quality reads were removed by Picard Tools v1.11 and Samtools v0.1.18 and processed using a bioinformatic workflow.

Figure 2:
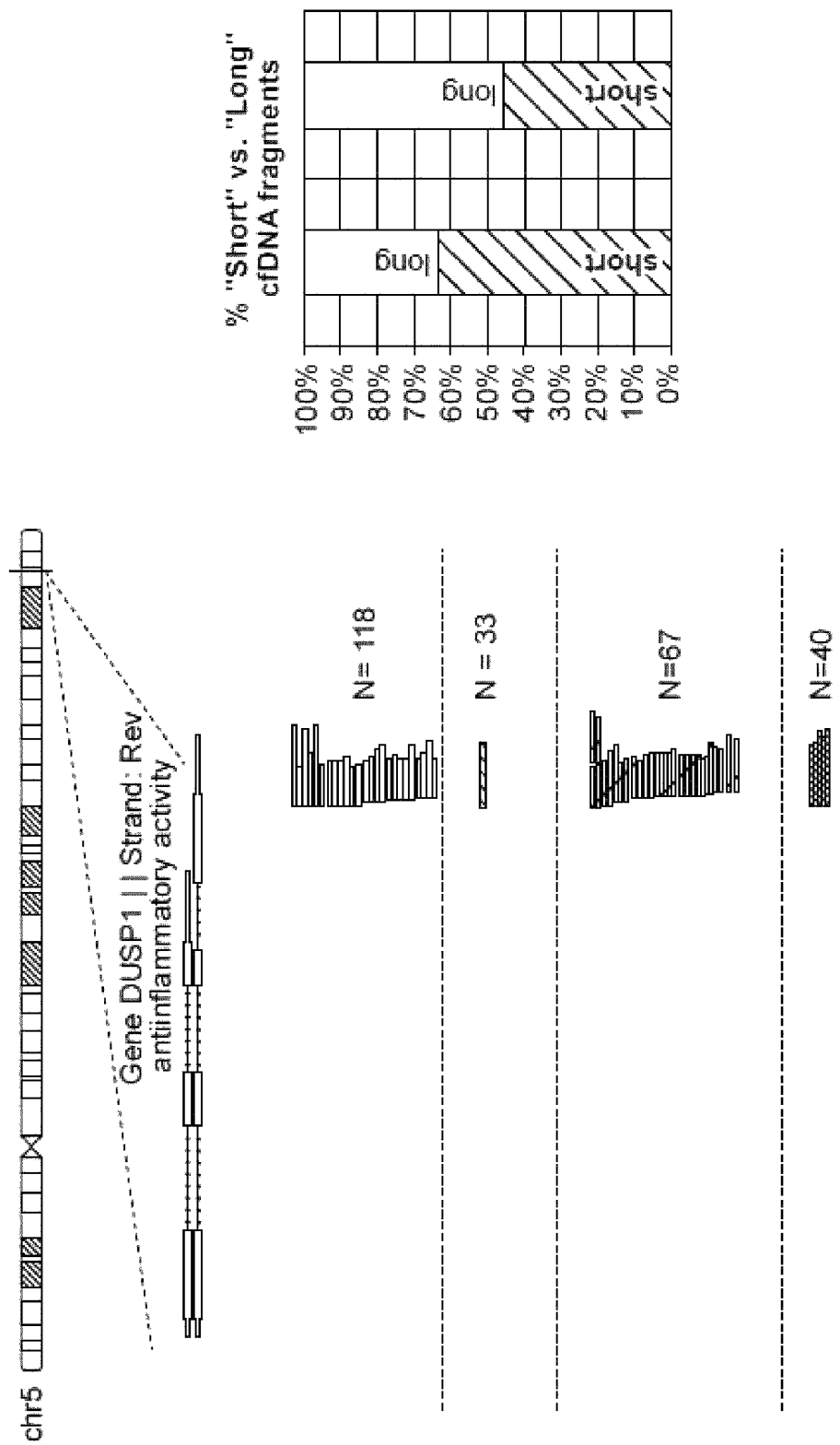
FIG. 2 illustrates anti-inflammatory glucocorticoid treatments induce expression of DUSP1 observed as the relative increase in long read counts at Timepoint 2 vs Timepoint 1.

Anti-inflammatory glucocorticoids are known to induce expression of the DUSPI gene. After prednisolone administration (Timepoint 2), there was a relative increase in the percentage of long cfDNA fragments derived from the promoter and first exon of the DUSPI gene, consistent with the expected increase in transcription factor and RNA polymerase binding to DUSP1(FIG. 2).

Figure 3:
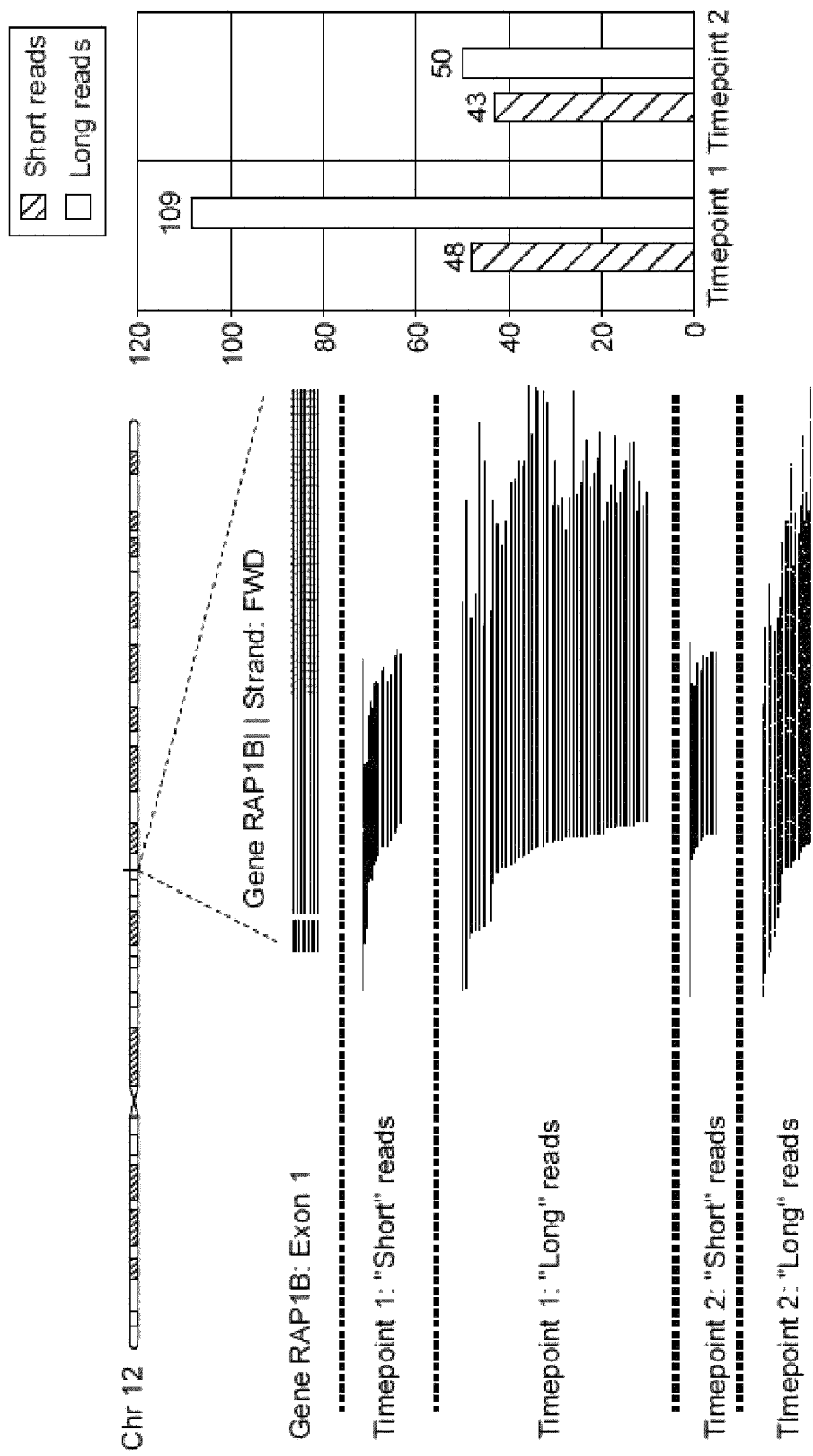
FIG. 3 illustrates glucocorticoid treatments induce expression of miR-708, leading to suppression of RAP1B expression, observed as a relative drop in "long" reads counts at Timepoint 2 vs. Timepoint 1.

Glucocorticoids induce the expression of miR-708 leading to the suppression of RAP1B transcription. cfDNA fragments derived from the promoter and first exon of RAP1B were compared before and after prednisolone administration to observe the effects of suppressing RAP1B. After prednisolone administration, there were relatively fewer long reads, consistent with the expected reduction transcription factor and RNA polymerase binding to the RAP1B promoter (FIG. 3).

Example 2. Monitoring Immunotherapy Responses in cfDNA Fragmentation Patterns Individuals with end-stage pancreatic cancer were treated with combination of 1000 mg/m$^2$ gemcitabine and 125 mg/m$^2$ nab-paclitaxel. Plasma samples were collected at two-month intervals and stored at −80° C. cfDNA was extracted from plasma samples of the three patients who survived to the T3 timepoint and the cfDNA fragments were sequenced on an Illumina® NovaSeq 6000 DNA sequencer as described in Example 1. The fragmentation pattern was interrogated to identify informative correlations between immunotherapy responsiveness and cfDNA fragmentation patterns.

Figure 4:
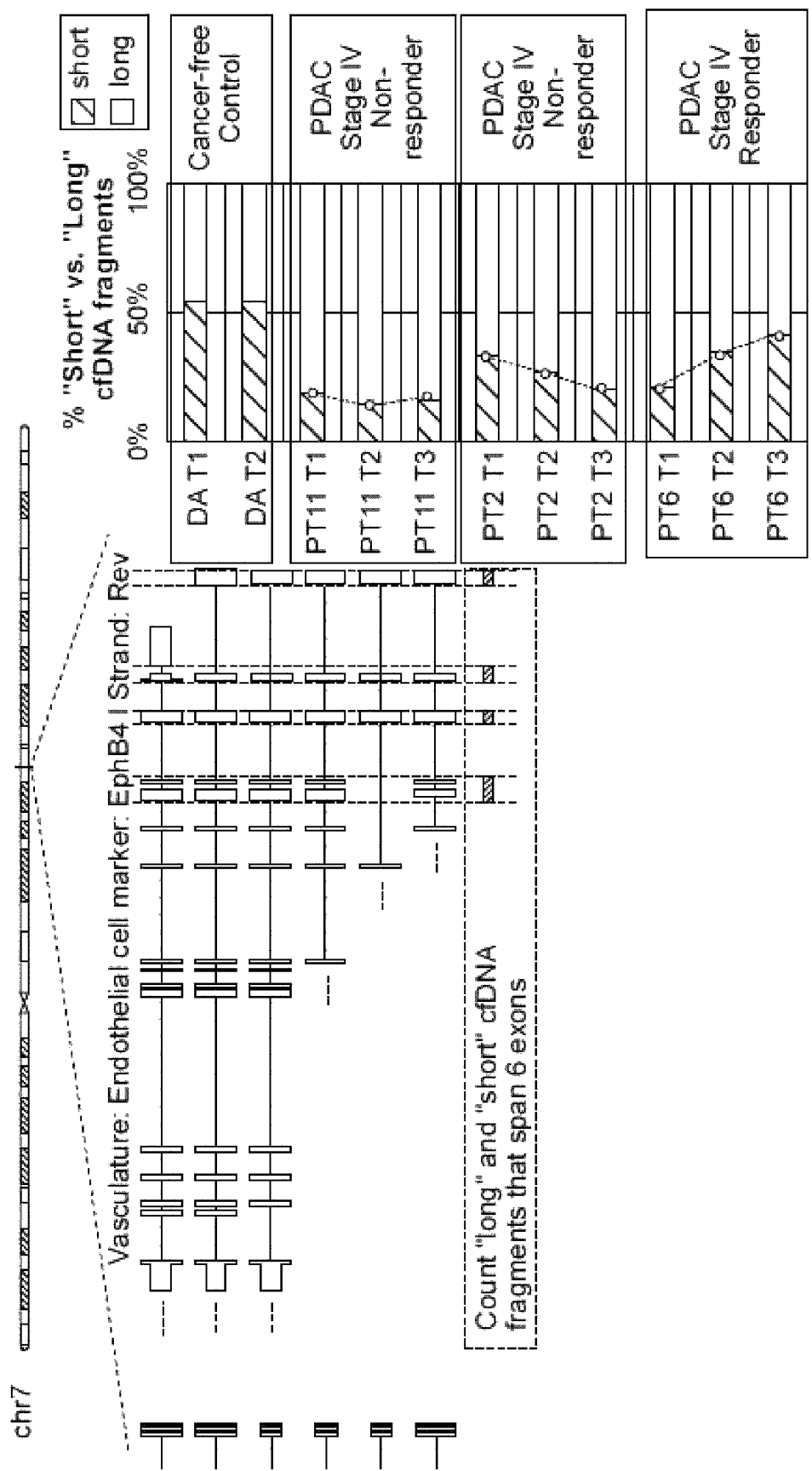
FIG. 4 illustrates characterization of the cfDNA fragmentation pattern of a genomic region of chromosome 7 (EphB4 locus) as determined from a composite signal spanning 6 exons and its use to monitor responses to immunotherapy.
Figure 5:
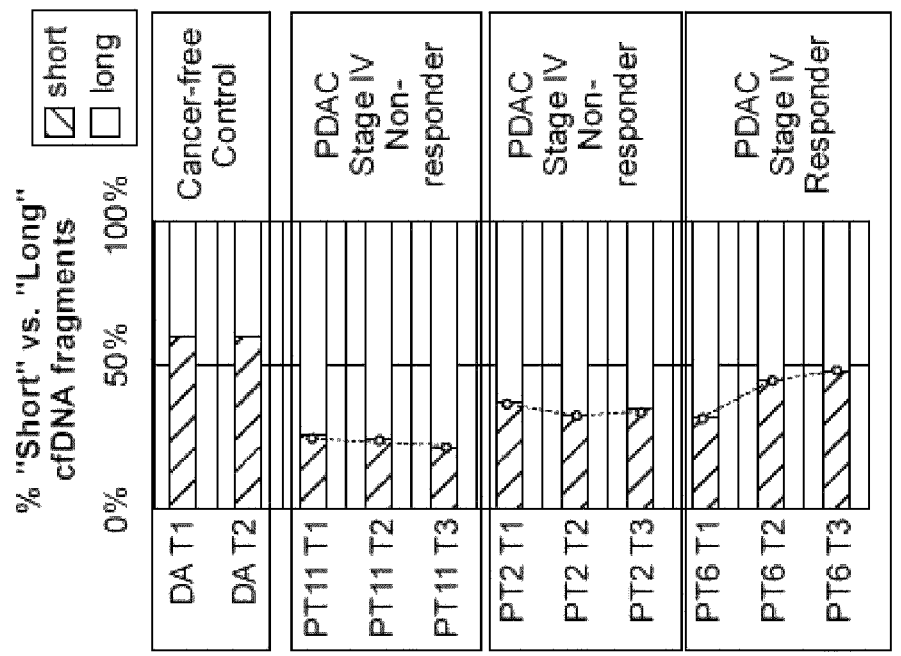
FIG. 5 illustrates characterization of a cfDNA fragmentation pattern comprising two genomic regions representative of a vasculature profile.
Figure 5:
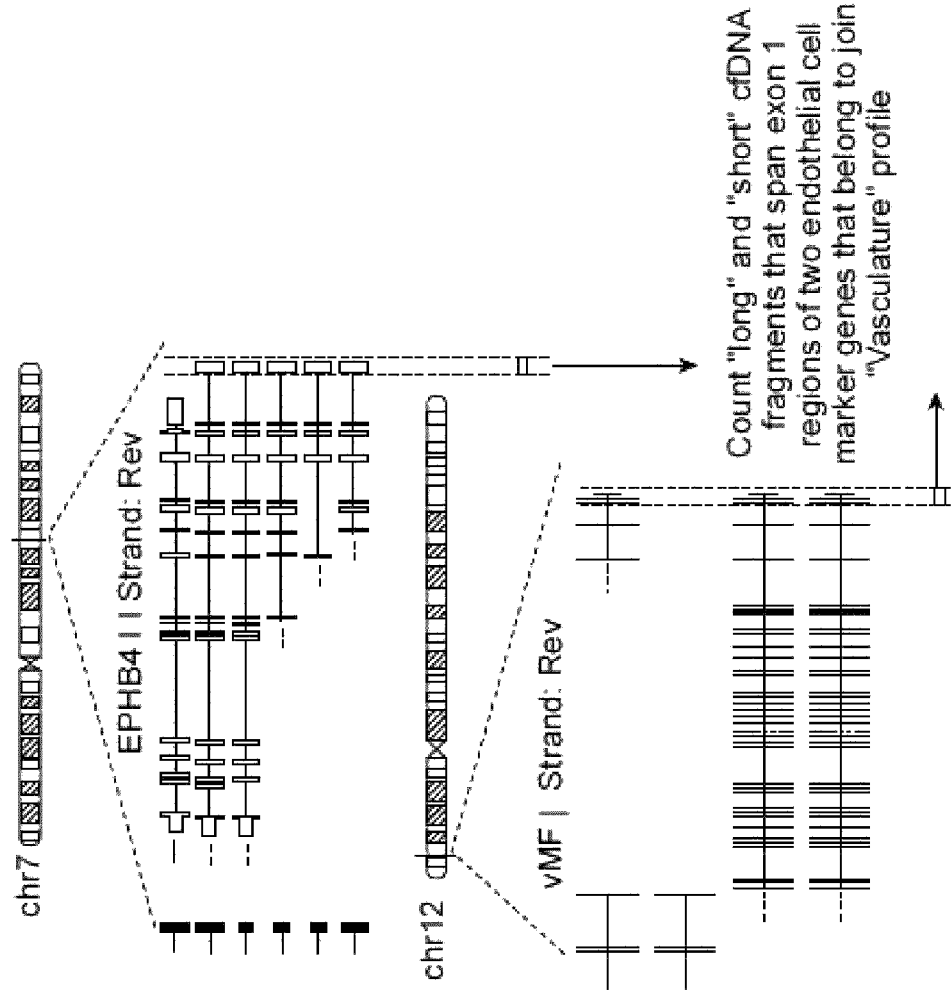

A significant correlation was observed at the EphB4 locus. EphB4 is expressed in endothelial cells which, aside from white blood cells, are the most prominent source of cfDNA. EphB4 functions in vasculogenesis, which creates a blood supply for tumors, suggesting a mechanistic connection between EphB4 expression and responsiveness to immunotherapy. In particular, the percentage of long cfDNA fragments derived from the first 6 exons of EphB4 increased over time in an individual (PT6) whose cancer responded to immunotherapy, and either remained constant or decreased in two individuals (PT11 and PT2) whose cancer did not respond to immunotherapy and in the healthy individual (DA) treated with prednisolone (FIG. 4). Additionally, the final percentage of long fragments in PT6 at the T3 was most similar to the percentage of long EphB4 cfDNA fragments observed in the healthy individual (FIG. 4).

TABLE 2 cfDNA fragment counts for endothelial cell marker EphB4 in a cohort of three pancreatic cancer patients and a cancer-free control subject over a time course study
Vasculature: Endothelial cell marker: EphB4

| | | | Fragment count | |
|---|---|---|---|---|
| | | | Short | Long |
| PoC study | Cancer-free control | DA T1 | 1225 | 823 |
| | | DA T2 | 1126 | 768 |
| Clinical feasibility study | Patient 11 | PT11 T1 | 85 | 238 |
| | | PT11 T2 | 90 | 274 |
| | | PT11 T3 | 75 | 269 |
| | Patient 2 | PT2 T1 | 131 | 218 |
| | | PT2 T2 | 147 | 284 |
| | | PT2 T3 | 117 | 217 |
| | Patient 6 | PT6 T1 | 116 | 240 |
| | | PT6 T2 | 95 | 116 |
| | | PT6 T3 | 167 | 179 |

A similar correlation between immunotherapy responsiveness and cfDNA fragmentation was observed at the vWF locus. The vWF gene also participates in vasculogenesis. A composite vasculogenesis response index was generated from the percentage of long cfDNA fragments derived from the EphB4 gene on chromosome 7 and vWF gene on chromosome 12. By including multiple genes in the composite index, it was possible to focus on fragments spanning the most informative exon, exon 1, while still considering enough total cfDNA fragments to provide a robust signal. The composite index increased over time in the responsive individual (PT6) and decreased in the non-responders (FIG.

5). At T3 (the final timepoint), PT6 had a similar percentage of long EphB4 and vWF fragments as the healthy individual. The same broad patterns were observed using two genes to map a vasculogenesis molecular function as using only EPHB4.

Early detection of immunotherapy responsiveness through a non-invasive test of cfDNA fragmentation patterns can identify responsive patients who should continue treatment and non-responsive patients who might benefit from treatment with a different compound.

Earlier detection may improve with a non-invasive cfDNA diagnostic may allow for molecular function profiles, such as vasculature, to quickly analyze treatment response thus ruling out ineffective treatments and their lengths of course and giving non-responders alternative line therapies earlier on in a treatment cycle. This may save costs, improve quality of life, and increase survival.

Example 3. Improved Methods of Detecting cfNA Fragmentation Patterns

Figure 6:
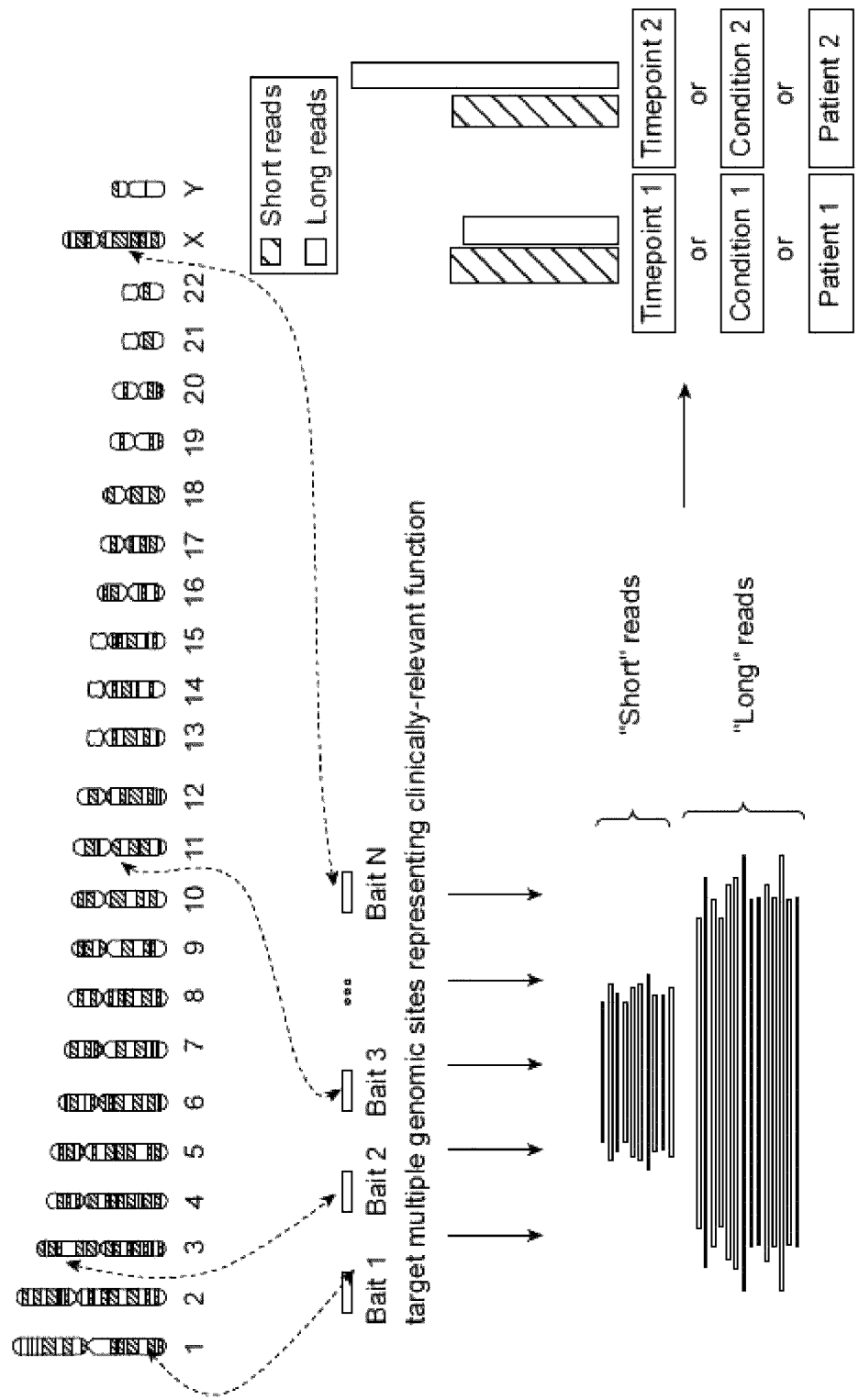
FIG. 6 illustrates a schematic of a method wherein oligonucleotide baits target multiple genomic regions representing clinically relevant functions and cluster them based on fragment length to create a composite signal.
Figure 7:
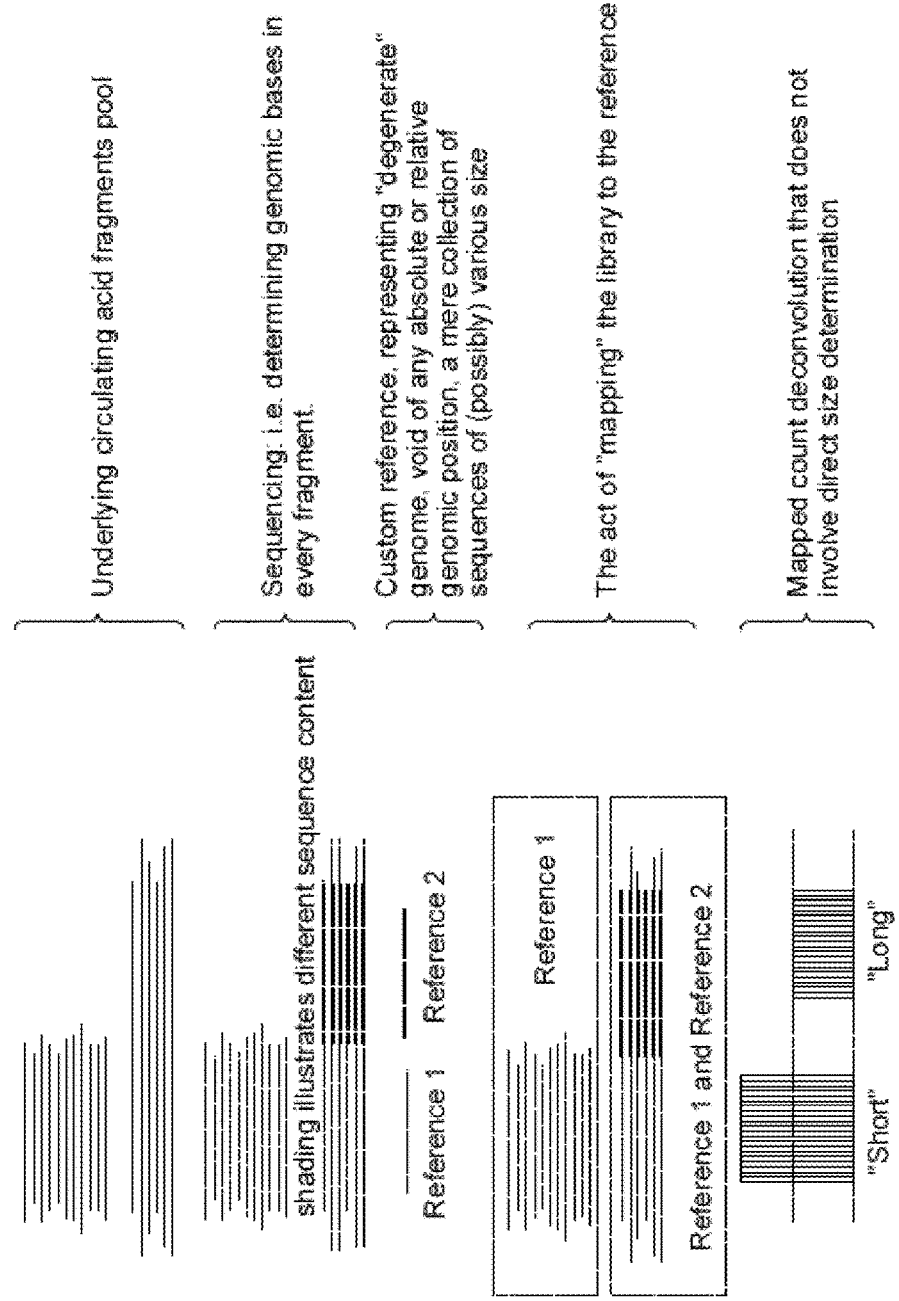
FIG. 7 illustrates sequencing-based deconvolution where a custom reference collection of sequences of various sizes absent absolute or relative genomic position is mapped to a library and the mapped count deconvolution does not involve direct size determination.
Figure 8:
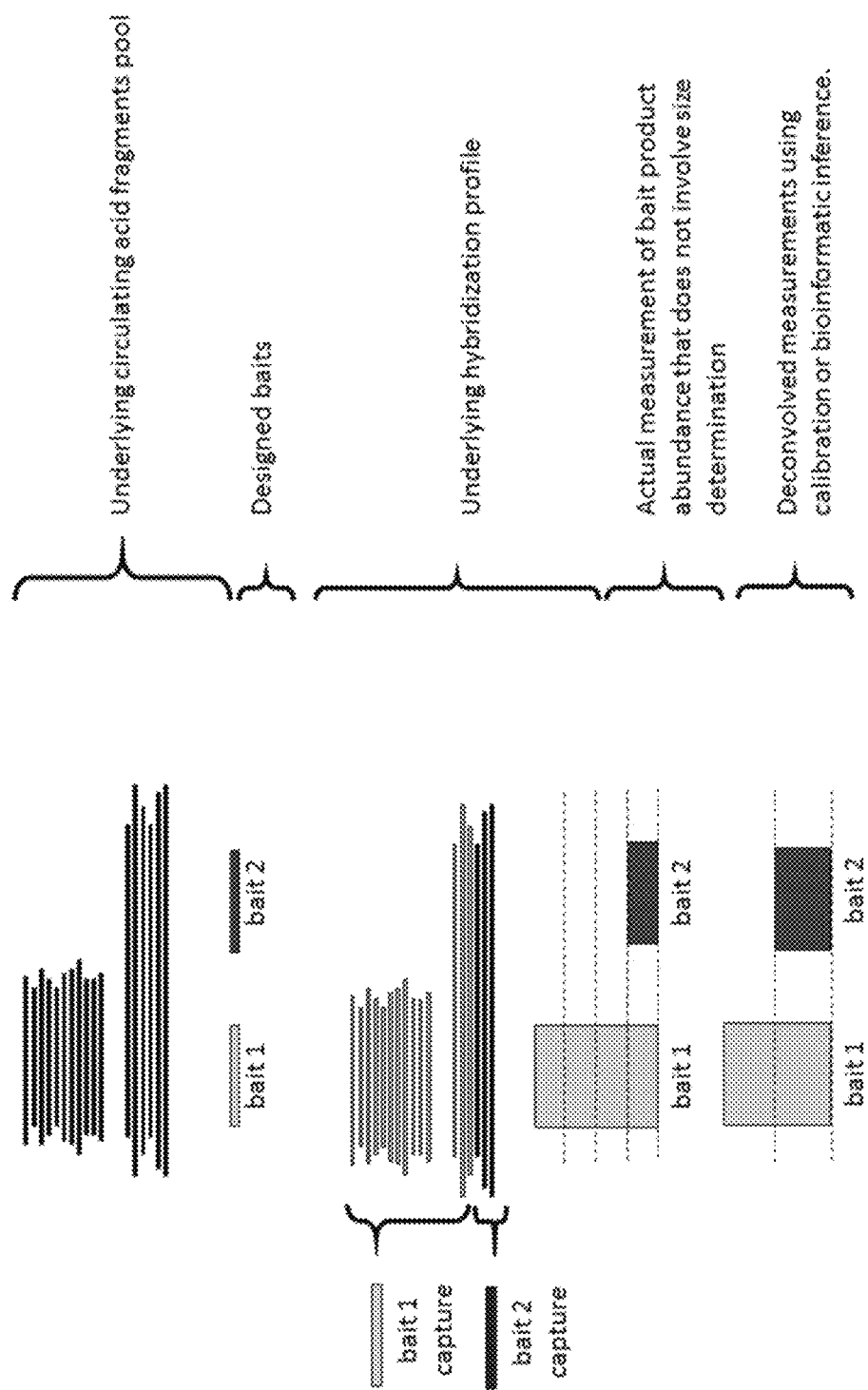
FIG. 8 illustrates hybridization capture of cfNA fragments with baits selective for silent (short) and active (long) cfDNA fragmentation patterns with discrimination between patterns determined by measuring amounts of cfDNA hybridized to each bait.

Targeted methods for analyzing cfNA fragmentation patterns at clinically relevant genomic sites can provide a more robust readout at a fraction of the cost of deep sequencing.
Capturing cfDNA Fragments With Baits A collection of baits is designed to target multiple cfDNA fragments derived from genomic sites representing clinically relevant functions, as illustrated in FIG. 6. Each bait captures a mixture of short (e.g. <230 nt) and long (e.g. >230 nt) cfDNA fragments. The abundance of short reads and long reads is compared for distinct timepoints, conditions, and/or patient groups. A change in the relative abundance of short and long cfDNA fragments is indicative of a change in physiological or pathological conditions according to the clinically relevant functions represented by the set of baits.
Inferring Fragment Sizes From the Amounts of DNA Captured by Two or More Baits A set of baits is designed to distinguish between known cfNA fragmentation patterns without determining the sizes of captured fragments, as illustrated in FIG. 8. A biological sample with a mixture of short and long cfNA fragments is contacted by two baits which capture distinct cfNA fragments and have a preference toward shorter or longer fragments. For example, bait 1 may capture shorter fragments and bait 2 may capture longer fragments. The relative amount of NA fragments hybridized to bait 1 and bait 2 is then used to infer the relative abundance of short and long fragments at the targeted genomic region. A set of baits may target cfNA fragments derived from one genomic region or multiple genomic regions.
Mapping Sequences to References to Characterize cfDNA Fragmentation The relative abundance of short and long fragments derived from one or more genomic regions can be quantified by mapping the sequences of captured fragments to custom references (keywords) as illustrated in FIG. 7. This method does not require determining the absolute length of each captured fragment, mapping fragment sequences to a reference genome, or identifying the ends of individual fragments. Nucleic acids isolated from a biological sample with a mixture of short and long NA fragments are sequenced to determine the nucleotide bases in a representative number of NA fragments. Reference 1 and Reference 2 represent different portions of the genomic site (e.g. a transcriptionally active locus). In the example depicted in FIG. 7, Reference 1 matches both short and long NA fragments, whereas Reference 2 matches only the longer fragments. Each sequenced NA fragment is scored for a match to Reference 1 and Reference 2. An increase in the proportion of NA fragment sequences matching Reference 2 (or Reference 1 and Reference 2) relative to NA fragment sequence that only match Reference 1 indicates an increase in the relative abundance of longer NA fragments at the genomic site.
Use of NA Amplification to Detect NA Fragmentation Patterns Nucleic acid amplification can be used to observe NA fragmentation patterns without determining the lengths of individual NA fragments, identifying the ends of individual NA fragments, sequencing the fragments, or mapping their sequences to a reference genome.

Figure 9:
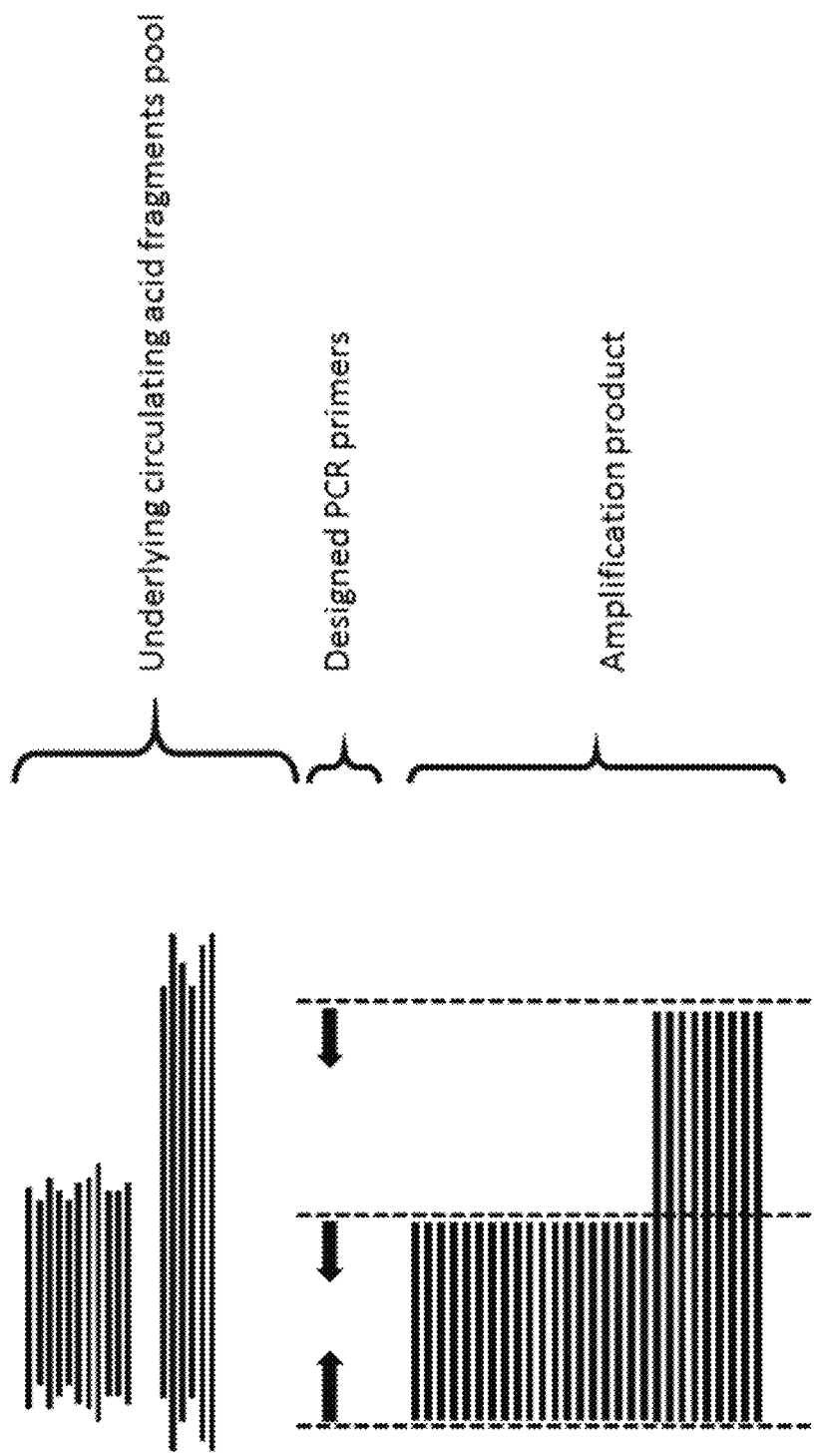
FIG. 9 illustrates using three probes in a competitive PCR reaction with subsequent deconvolution of the underlying fragment counts through accounting for amplification bias or directly calibrating against synthetic pools.

As illustrated in FIG. 9, a set of three primers can be designed to generate a mixture of short and long amplicons from cfNAs in a biological sample. A forward primer and one reverse primer hybridize to both short and long cfNA fragments, and a second reverse primer only hybridizes to the longer fragments. The relative abundance of short or long amplicons correlates with the abundance of short and long nucleic acid fragments in the biological sample.

Figure 10:
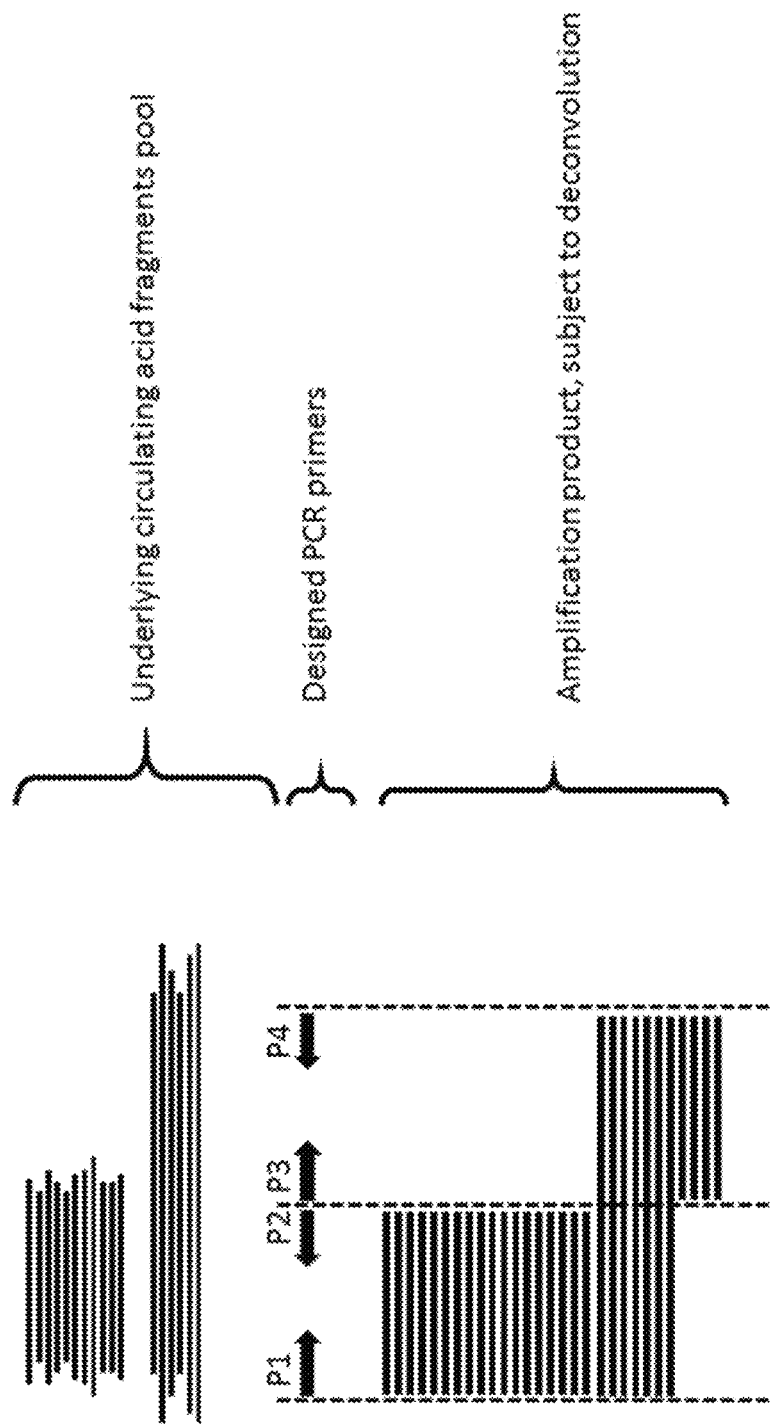
FIG. 10 illustrates using four probes in a competitive PCR reaction with subsequent deconvolution of the underlying counts.

As illustrated in FIG. 10, a set of four primers can be designed to generate a mixture of two short amplicons and a long amplicon from a heterogeneous population of NAs in a biological sample. A first pair of primers (P1 and P2) produces a short amplicon representing one portion of the genomic site and a second pair of primers (P3 and P4) produces a short amplicon representing another portion of the genomic site. A longer amplicon can be generated from the outer primers (P1 and P4). The relative abundance of the short and long amplicons correlates with the abundance of short and long nucleic acid fragments in the biological sample.

Figure 11:
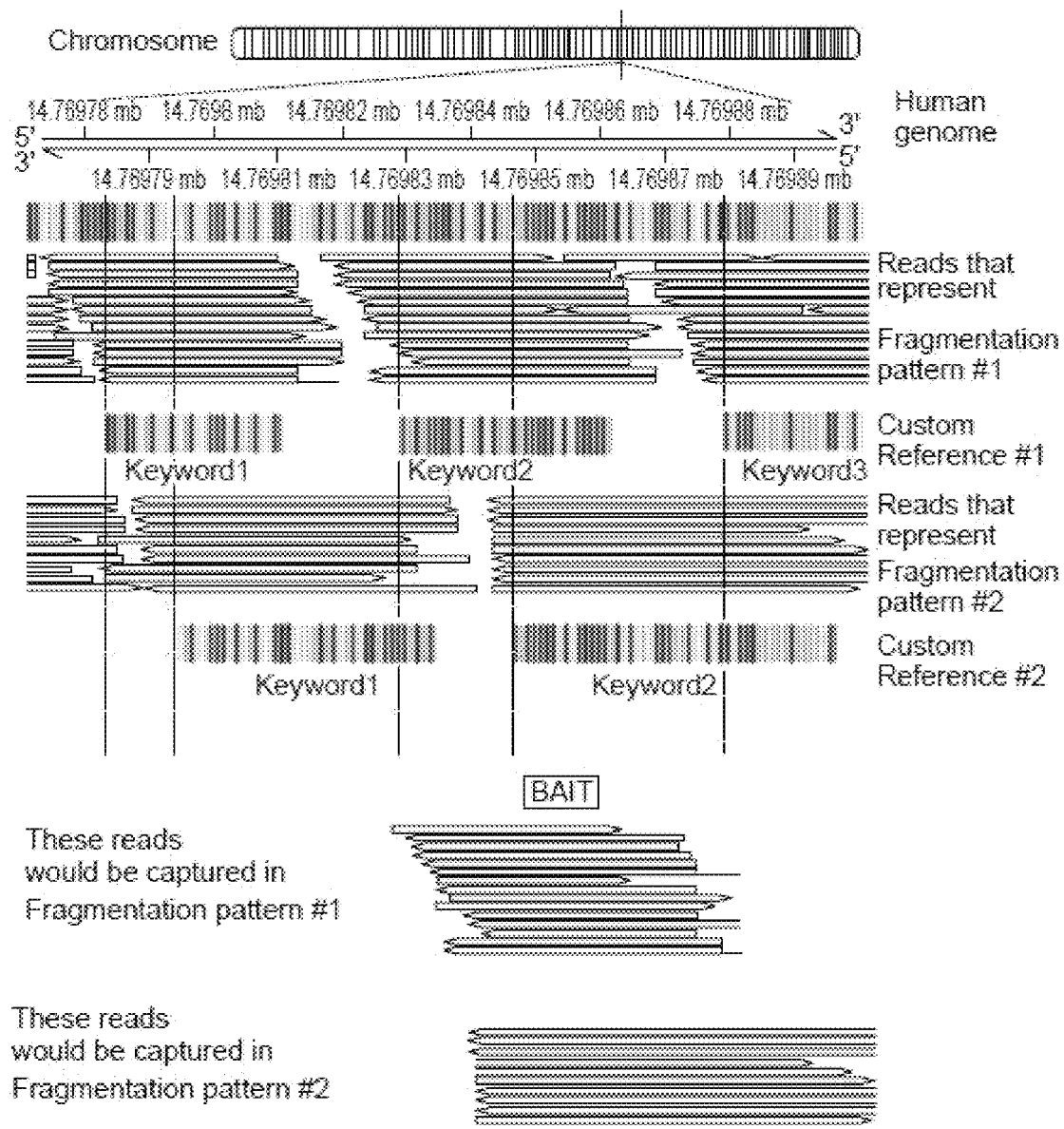
FIG. 11 illustrates the use of cfNA sequencing and custom references comprising multiple segments (keywords) to distinguish cfNA fragmentation patterns.

Nucleic acid amplification with the three primers of FIG. 9 or the four primers of FIG. 10 can be performed in competitive reactions with all three or four primers, or in separate reactions where the amount of each amplicon produced per amplification cycle is quantified. The principles for discriminating fragmentation patterns with three or four primers can be expanded by adding more primers to produce amplicons of various sizes representing additional or overlapping portions of the genomic site. Using multiple probes allows a plurality of overlapping polynucleotides to span a genomic region of interest.
Custom References Represent Different Fragmentation Patterns Custom references comprising one or more segments from a transcriptionally active locus (keywords) are designed to represent the cfNA fragments that are most abundantly or selectively present in a given fragmentation pattern in a genomic region. FIG. 11 illustrates two fragmentations patterns for a genomic region. Most cfNA fragments of Fragmentation pattern #1 overlap the keywords of Custom reference #1 and most cfNA fragments of Fragmentation pattern #2 overlap the keywords of Custom reference #2.

One method of comparing the relative abundance of the two fragmentation patterns in a biological sample is to sequence cfNA fragments derived from the genomic region and match the sequences via alignment-free methods to the keywords of Custom references #1 and #2. If fragmentation pattern #1 predominates, a higher percentage of the cfNA fragment sequences will match the keywords of Custom Reference #1. For this method, all cfNA fragments derived from a genomic region (e.g. transcriptionally active locus) can be enriched using tiled baits that cover the entire region and are not selective for either fragmentation pattern.

In another method, a comparison is made of the amounts of cfNA fragments captured by baits corresponding to the keywords of Custom References #1 and #2. An increase in the amount of cfNA fragments captured by Custom Reference #1 baits compared to the amount of cfNA fragments captured by Custom Reference #2 baits would indicate an increase in the proportion of Fragmentation pattern #1 compared to Fragmentation pattern #2.

Example 4. Comparing a Diseased Patient to a Healthy Control

Overall, methods of this system comprise extracting cfNAs from plasma, collecting cfNA fragments with baits, quantifying large and small cfNA fragments, and performing statistical tests to determine the presence or progression of a pathological or physiological condition. Biological samples from one or more patients and one or more healthy volunteers are collected through a non-invasive procedure such as a blood draw. A plurality of cfNA fragments are isolated using baits. In some embodiments, all cfNA fragments isolated from a biological sample are analyzed. In other embodiments, targeted cfNA fragments are captured from a nucleic acid fraction isolated from a biological sample. Captured cfNA pools are quantified for each biological sample. The median abundances of captured cfNA pools in healthy and diseased cohorts are identified and baits with the highest variation in sizes and/or abundances of cfNA fragments are identified. Variations in sizes and/or abundances can be compared by any suitable parametric or non-parametric mathematical relationship. For example, a first Pearson correlation is calculated between the cfDNA sizes and/or abundances in identified pools in a tested sample as compared to healthy cohorts. A second Pearson correlation is calculated between the cfDNA sizes and/or abundances in identified pools in a tested sample as compared to diseased cohorts. A disease, disorder, or condition is identified or diagnosed if the second Pearson correlation is stronger in magnitude than the first Pearson correlation.
Comparing a Healthy Control With an Induced Pharmacological Response Biological samples are collected from one or more patients and one or more healthy volunteer that received a targeted drug or treatment through a non-invasive procedure such as drawing blood in a blood draw. cfNAs are isolated from the collected biological samples. A plurality of cfNA fragments are isolated from fragments using baits that target genomic regions that are expected to be altered due to the drug: treatment interaction. The isolated pools are quantified for each sample and the median abundances of isolated pools in healthy and diseased cohorts are identified. Baits with the highest variation in sizes and/or abundances of cfNA fragments are identified. A first Pearson correlation between the cfNA sizes and/or abundances in identified pools in a tested sample vs. healthy cohorts is determined and a second Pearson correlation between the cfNA sizes or abundances in identified pools in a tested sample as compared to diseased cohorts is calculated. A disease, disorder, or condition is identified or diagnosed if the second Pearson correlation is stronger in magnitude than the first Pearson correlation.
Longitudinal Analysis Biological samples are collected from one or more patients and one or more healthy volunteer that received a targeted drug or treatment through a non-invasive procedure such as drawing blood in a blood draw. cfNAs are isolated from the collected biological samples. A plurality of cfNA fragments are isolated using baits that target genomic regions with the anticipated regulatory changes associated with a disease. The isolated pools are quantified for each sample and the abundances and/or sizes of isolated pools at all time points identified. Statistical methods for detecting changes in a longitudinal time series for each pool are performed. The disease, disorder, or condition is identified or diagnosed if a statistically-significant and sustained change is detected via Change Point analysis that detect distinct changes in time series data.

Example 5. Methods of Distinguishing Two Fragmentation Patterns

FIG. 12-18 present various methods of distinguishing between two cfDNA fragmentation patterns by enriching long cfDNA fragments. The top part of each figures illustrates a genomic region with a promotor and a transcriptional start site. The arrow represents an mRNA. This exemplary genomic region has two states: an off-state present in normal cells and an on-state present in diseased cells. In the Normal (off) state, the genomic DNA is wrapped around nucleosomes that consistently bind to the same segments of genomic DNA. In the Diseased (on) state, a complex of transcription factors binds to the promoter and an RNA polymerase often associates with a segment of DNA at a position where transcription is delayed or stalled.

Nucleosomes, transcription factors, polymerases and other DNA-binding proteins remain associated with the genomic DNA when a cell dies and protect the DNA segments that they bind to from degradation by nucleases acting during apoptosis, necrosis, or other forms of cell death. Consequently, cfDNA fragments released from dying cell into circulating blood have different fragmentation patterns depending upon the activation state before cell death. The Normal cfDNA fragmentation pattern has cfDNA fragments that overlap the three nucleosome binding sites and the Diseased cfDNA fragmentation pattern has cfDNA fragments that overlap the transcription factor binding site and the polymerase stall site.

Figure 12:
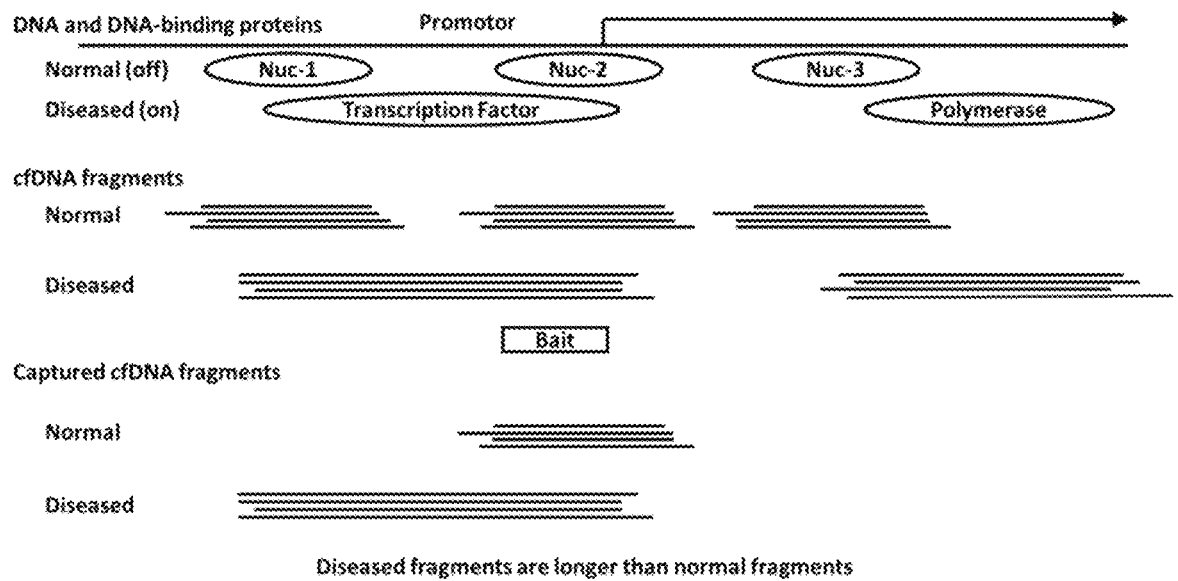
FIGS. 12-18 illustrate various methods of distinguishing between two cfNA fragmentation patterns.

The two fragmentation patterns can be distinguished using an oligonucleotide bait that captures cfDNA fragments comprising a sequence that overlaps a set of shorter cfDNA fragments protected by a nucleosome in normal cells and a set of longer cfDNA fragments protected by a transcription factor complex in diseased cells, as illustrated in FIG. 12. The captured cfDNA fragments are separated according to their size (length) by electrophoresis. An increase in the amount of long cfDNA fragments captured by the bait is indicative of the Diseased state.

Figure 13:
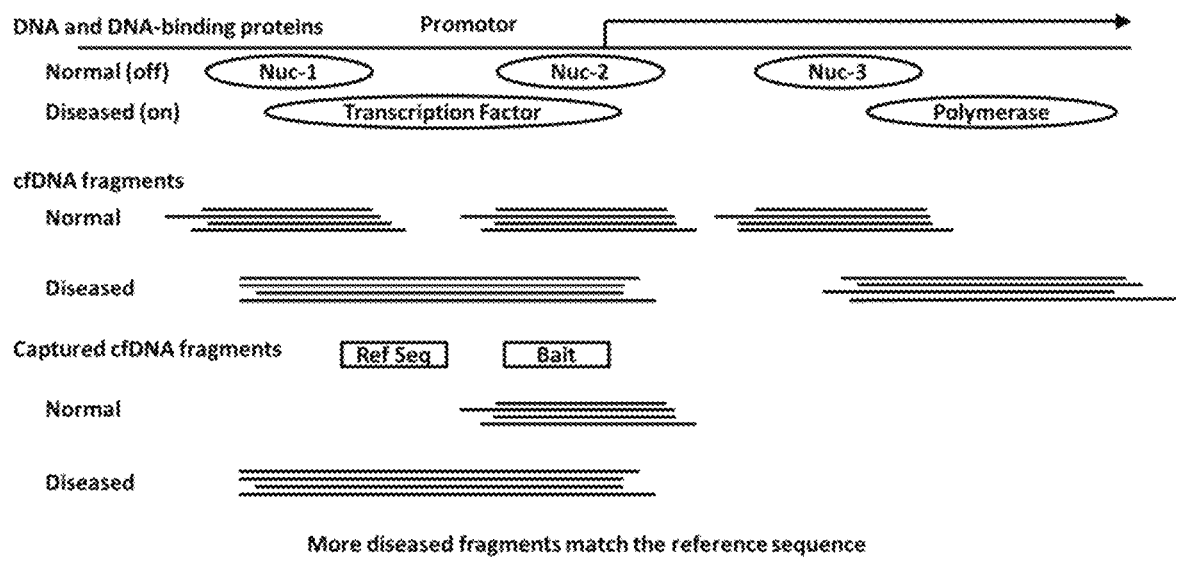

The two fragmentation patterns can be distinguished using an oligonucleotide bait that captures cfDNA fragments comprising a sequence that overlaps a set of shorter cfDNA fragments protected by a nucleosome in normal cells and a set of longer cfDNA fragments protected by a transcription factor complex in diseased cells, as illustrated in FIG. 13. The captured cfDNA fragments are sequenced. Each sequence is evaluated for a match to a reference sequence representing a portion of the DNA segment protected by the transcription factor in the Diseased state. An increase in the percentage of DNA sequences matching the reference sequence is indicative of the Diseased state.

Figure 14:
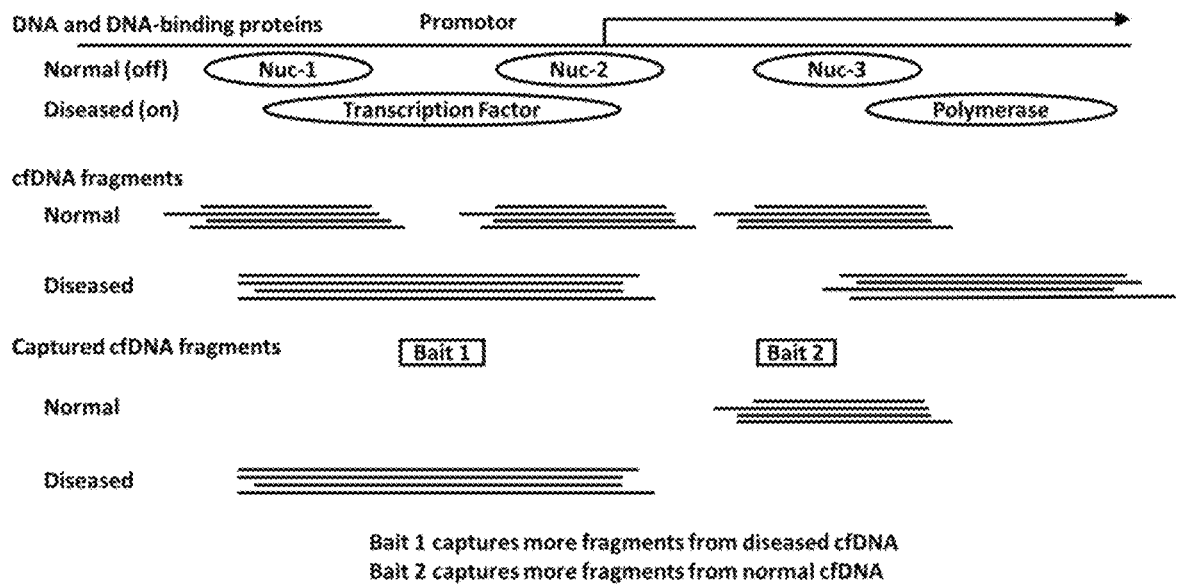

The two fragmentation patterns can be distinguished using two oligonucleotide baits, as illustrated in FIG. 14. Bait 1 captures long cfDNA fragments protected by the transcription factor in the Diseased state. Bait 2 captures shorter cfDNA fragments protected by a nucleosome in the Normal state. An increase in the relative amount of cfDNA fragments captured by Bait 1 is indicative of the Discased state.

Figure 15:
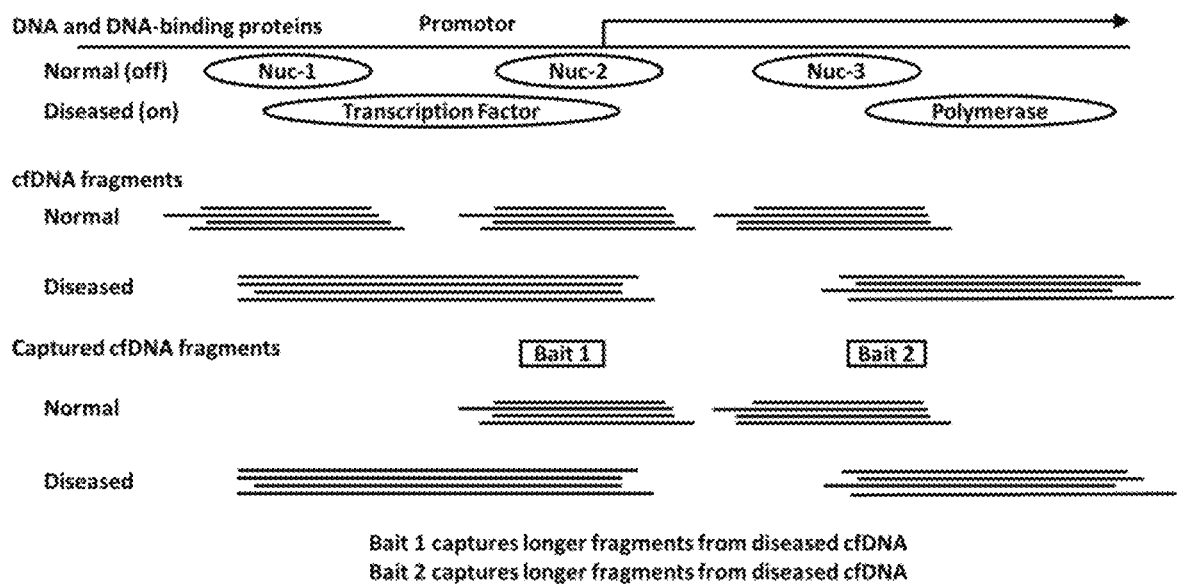

The two fragmentation patterns can be distinguished using two oligonucleotide baits, as illustrated in FIG. 15. Bait 1 captures long cfDNA fragments protected by the transcription factor in the Diseased state and shorter cfDNA fragments protected by a nucleosome in the Normal state. Bait 2 captures long cfDNA fragments protected by the polymerase in the Diseased state and shorter cfDNA fragments protected by a nucleosome in the Normal state. The sizes of the two populations of captured cfDNA fragments are compared by electrophoresis. An increase in the proportion of long cfDNA fragments associated with Baits 1 and 2 is indicative of the Diseased state. Confidence in the conclusion is increased by using two Baits.

Figure 16:
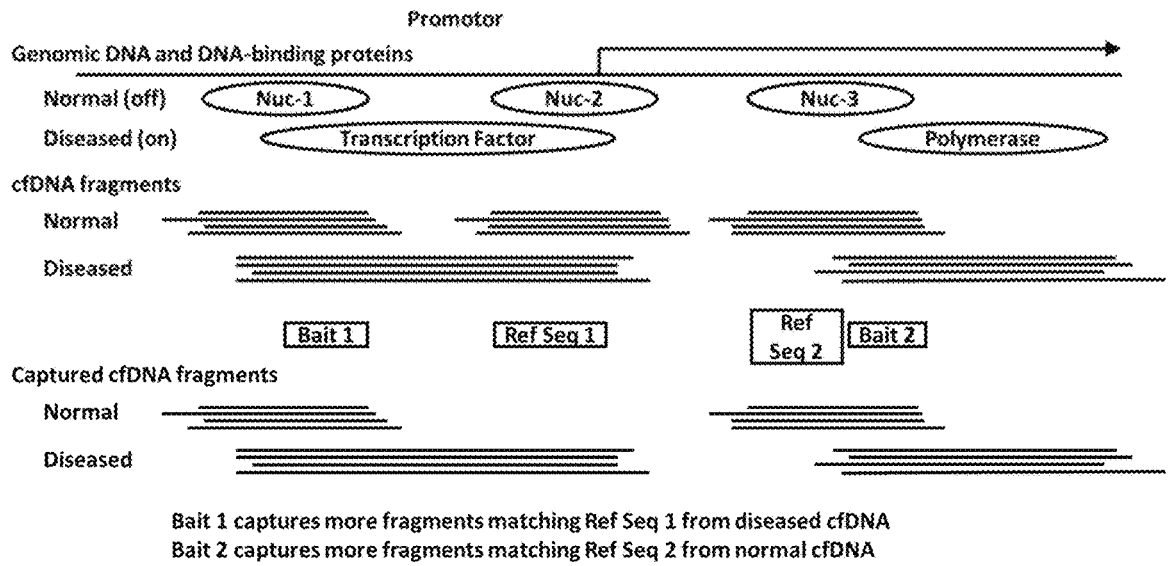

The two fragmentation patterns can be distinguished using two oligonucleotide baits, as illustrated in FIG. 16. Bait 1 captures long cfDNA fragments protected by the transcription factor in the Diseased state and shorter cfDNA fragments protected by a nucleosome in the Normal state. Bait 2 captures long cfDNA fragments protected by the polymerase in the Diseased state and shorter cfDNA fragments protected by a nucleosome in the Normal state. The captured cfDNA fragments are sequenced. The Diseased state is indicated by an increase in the number of captured cfDNA fragments with sequences matching a Reference Sequence 1 representing a portion of the DNA segment protected by the transcription factor in the Diseased state and a decrease in the number of captured cfDNA fragments with sequences matching a Reference Sequence 2 representing a portion of the DNA segment protected by a nucleosome in the Normal state.

Figure 17:
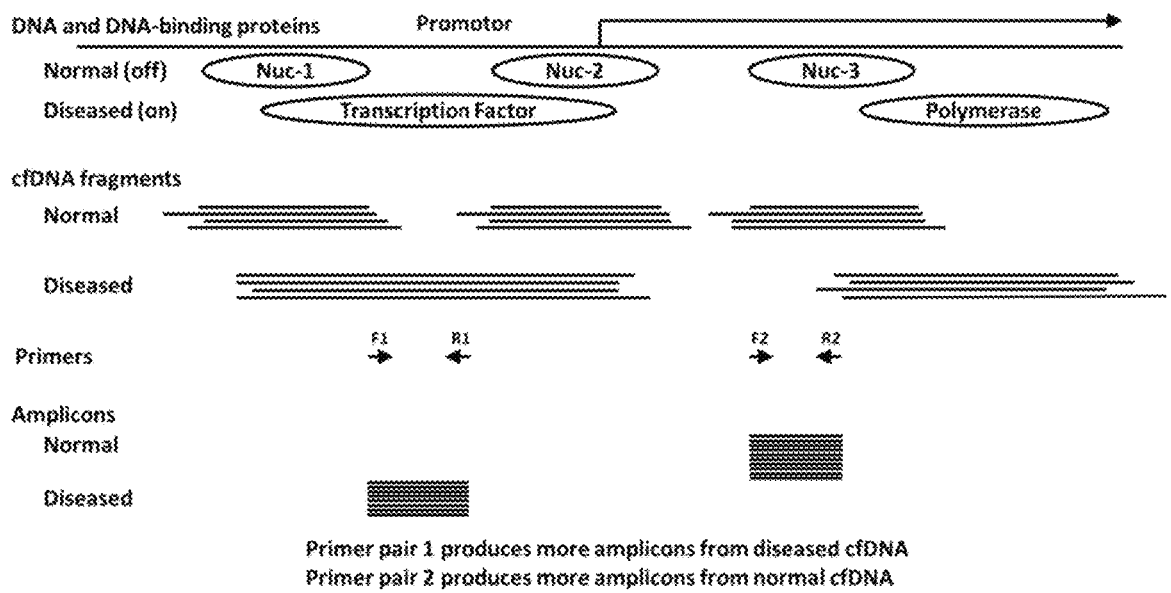

The two fragmentation patterns can be distinguished by amplifying segments of cfDNA representing the Diseased and Normal states, as illustrated in FIG. 17. For example, a cfDNA segment derived from cfDNA fragments protected by the transcription factor in the Discased state is amplified using the F1 and R1 primers and a cfDNA segment derived from cfDNA fragments protected by Nucleosome 3 in the Normal state is amplified using the F2 and R2 primers. A relative increase in the segment amplified by the first primer pair compared to the second primer pair is indicative of the Diseased state.

Figure 18:
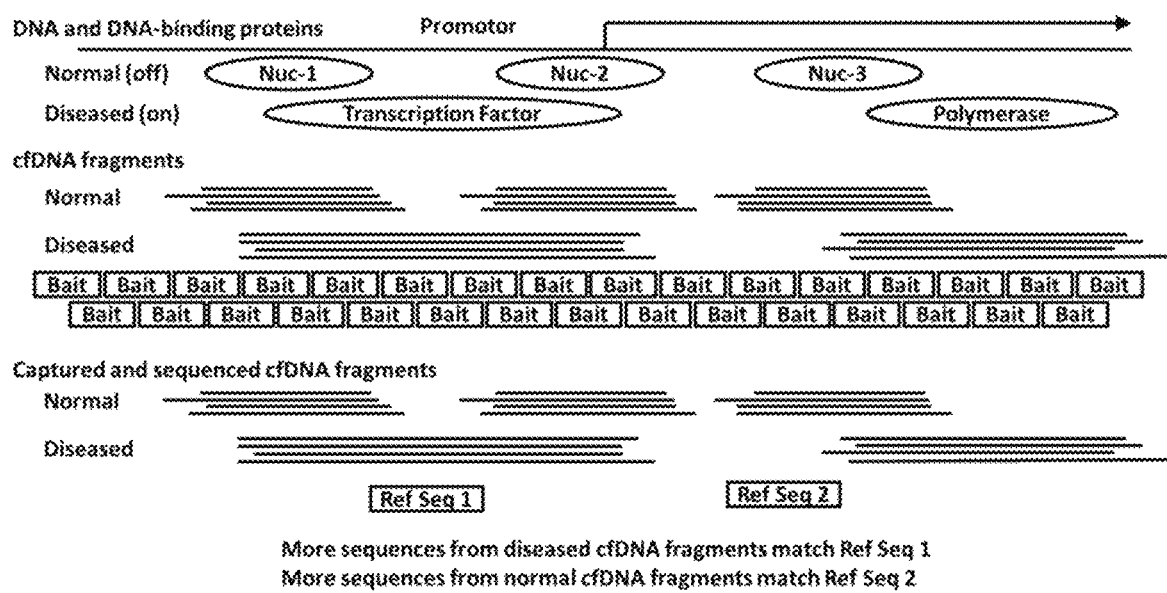

The two fragmentation patterns can be distinguished by using tiled baits to capture all cf DNA fragments derived from the entire genomic region as illustrated in FIG. 18. Sequences of the captured cfDNA fragments are matched by alignment-free methods to Reference Sequence 1 representing the DNA segment protected by the transcription factor in the Discased state and Reference Sequence 2 representing the DNA segment protected by Nucleosome 3 in the Normal state. An increase in sequences matching Reference Sequence 1 compared to Reference Sequence 2 indicates the Diseased state.

Example 6. Detecting Changes in cfDNA Fragmentation Patterns After Prednisone Treatment The cfDNA samples and whole genome sequencing data of Example 1 were further analyzed to determine whether low-dose glucocorticoid treatment induced changes that can be detected by the methods disclosed herein. Genomic regions within transcriptionally active loci on chromosome 5 (DUSP1) and chromosome 19 (SAE1) were analyzed to provide exemplary data. In some examples, transcriptional activation scores (TAS) from hybridization capture experiments were compared with simulated results from the paired-end whole-genome sequencing (WGS) dataset.

Some processes only involve the base call generation and at least one reference sequence. A reference sequence can be a substring of a TAL that is used in approximate string matching of WGS data. Specifically, the sequences obtained in WGS experiment are subjected to partial fuzzy matching against the reference sequence(s) to identify which WGS sequences bare a significant substring similarity with the reference sequence. The term "fuzzy" refers to the fact that the matching algorithm does not look for a perfect, position-by-position match when comparing two strings.

Gene regulation is driven by the promoter and the transcription machinery (Wärnmark et al, Activation functions 1 and 2 of nuclear receptors: molecular strategies for transcriptional activation. *Molecular Endocrinology.* 17 (10): 1901-9). Many genomic regions have been identified as drivers of the specific expression of genes and their unique RNAs. Transcription factors are proteins that are involved in transcribing DNA into RNA. Transcription factors include a wide variety of proteins, excluding RNA polymerase, that initiate and regulate the transcription of genes. Transcription factors possess DNA-binding domains that give them the ability to bind to specific sequences of DNA such as enhancer or promoter sequences. Some transcription factors bind to a DNA promoter sequence near the transcription start site and help form the transcription initiation complex. Other transcription factors bind to regulatory sequences, such as enhancer sequences, and can either stimulate or repress transcription of the related gene. These regulatory sequences can be thousands of base pairs upstream or downstream from the gene being transcribed.

Figure 19:
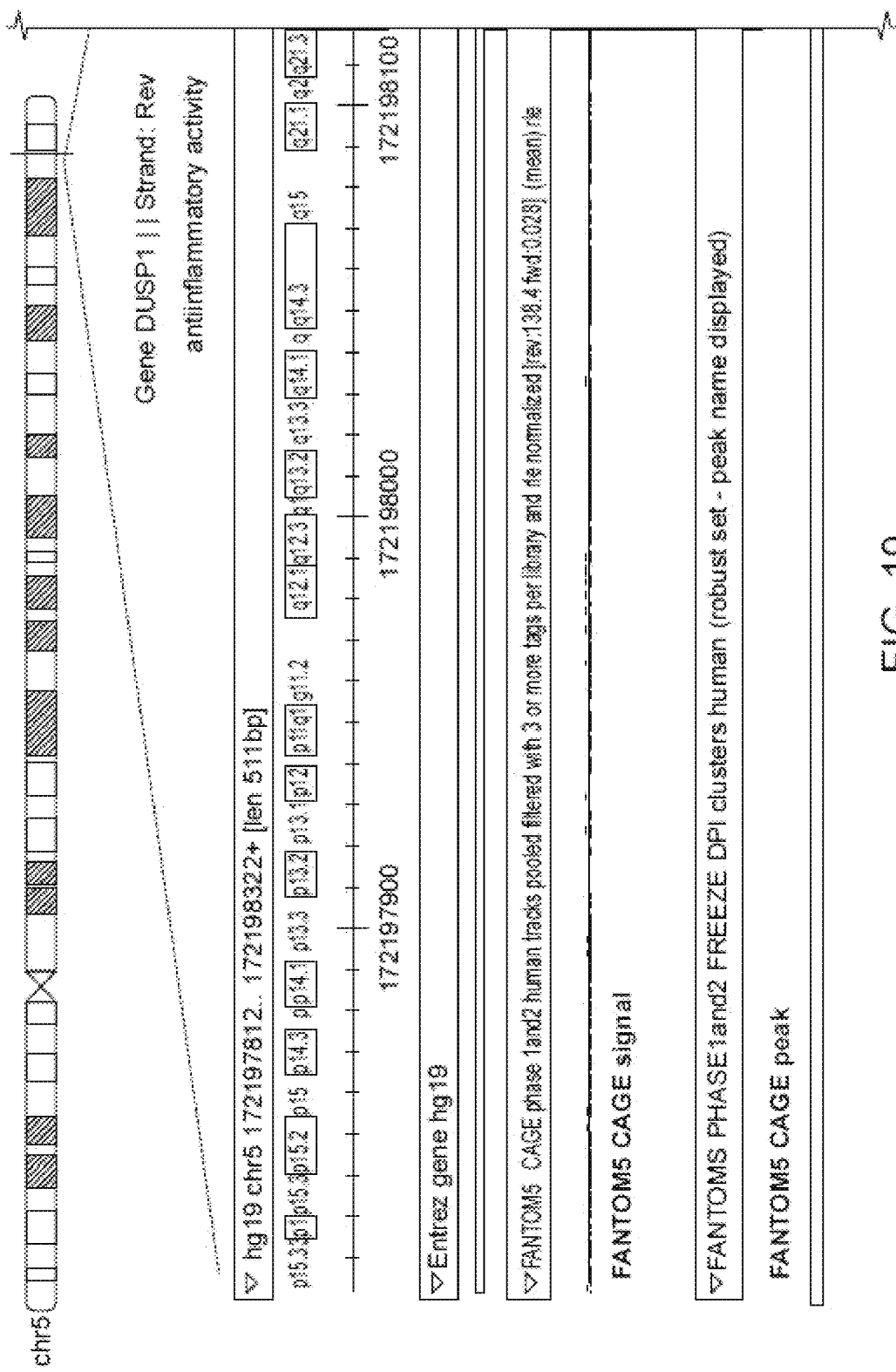
FIG. 19 illustrates a Cap Analysis of Gene Expression (CAGE) signal in the p1promoter region of DUSP1 and a Transcriptionally Active Locus (TAL) with a cfNA fragmentation pattern that differs between transcriptionally silent and active states.
Figure 19:
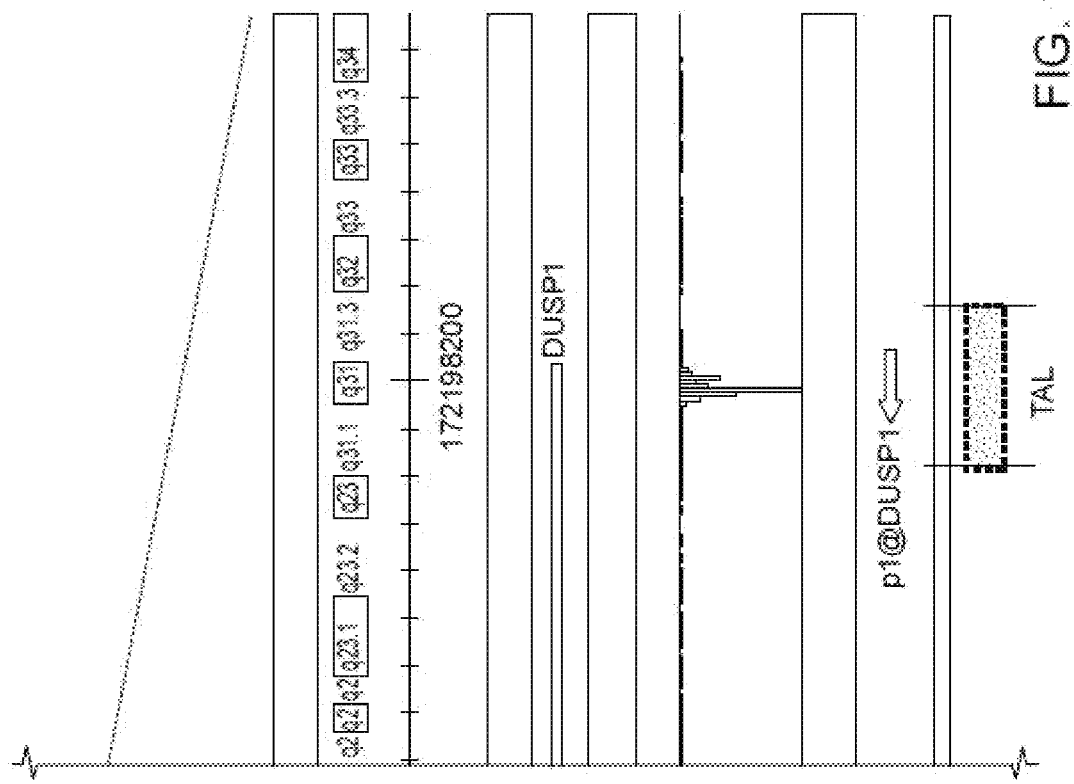

FIG. 19 shows an example of a genomic region involved in transcription initiation that was discovered by the Cap Analysis of Gene Expression (CAGE) technique (Kanamori-Katayama et al. Unamplified cap analysis of gene expression on a single-molecule sequencer. *Genome Res.* 2011 July; 21(7):1150-9). In the FANTOM5 project, transcription initiation events across the human genome were mapped at a single base-pair resolution and their frequencies were monitored by CAGE (Noguchi et al. FANTOM5 CAGE profiles of human and mouse samples. *Sci Data* 4, 170112 (2017)). A peak in CAGE signal is observed in the promoter region of DUSP1, identified as p1 promoter of DUSP1 (FIG. 19).

A Transcriptionally Active Locus (TAL) is a genomic region with an open and active chromatin architecture that enable transcription. Such regions mediate precisely controlled patterns of gene expression and may include known classes of transcriptional regulatory elements, such as core promoters, proximal promoters, distal enhancers, silencers, insulators/boundary elements, and locus control regions described in public databases, e.g. FANTOM5 or Encyclopedia of DNA Elements (ENCODE). Additional regulatory elements as well as novel regions can be identified in independent studies. A TAL may also represent a genomic region involved in acceleration, deceleration, backtracking, pausing and release of the pol II transcription elongation complex. An example of the TAL for gene DUSP1 is shown in FIG. 19.

The bloodstreams deliver nutrients and oxygen to tissues, carry out immunological surveillance, and remove the waste from dying cells. The latter includes nucleic acids from normal cells that died as part of cellular turnover within or outside the bloodstream. (Hummel et al. Cell-free DNA release under psychosocial and physical stress conditions. *Transl Psychiatry* 8, 236 (2018)). Some of these cellular debris carry the transcriptional footprint of original cell function. (Ulz et al. Inferring expressed genes by whole-genome sequencing of plasma DNA. *Nat Genet* 48, 1273-1278 (2016)). The distribution of counts and lengths of the cfDNA fragments in the bloodstream can be affected by the presence of DNA-bound protein complexes including pol II transcription elongation complexes prior to and during cell death. Disclosed herein are methods to capture specific cell-free nucleic acids within transcriptionally active loci and enable dynamic surveillance of changes in biological pathways associated with disease progression and response to drug or treatment. Some of these methods involve hybridization capture and characterization of the capture product.

Hybridization-based capture is one of the most powerful and versatile tools to allow rapid and selective target enrichment. Hybridization capture methods typically involve denaturing DNA by heating and then contacting the denatured DNA with single-stranded DNA or RNA oligonucleotides (called also "probes" or "baits") specific to a region of interest to allow the baits to hybridize to the target DNA (Kozarewa et al. (2015). Overview of target enrichment strategies. *Curr. Protoc. Mol. Biol.* 112:7.21.1-7.21.23). RNA baits are preferred in some embodiments because RNA: DNA duplexes have better hybridization efficiency and stability than DNA: DNA hybrids. (Lesnik and Freier (1995). Relative thermodynamic stability of DNA, RNA, and DNA:RNA hybrid duplexes: relationship with base composition and structure. *Biochemistry* 34, 10807-10815). Non-specific unbound molecules are washed away, and the enriched DNA is eluted for further analysis.

Figure 20:
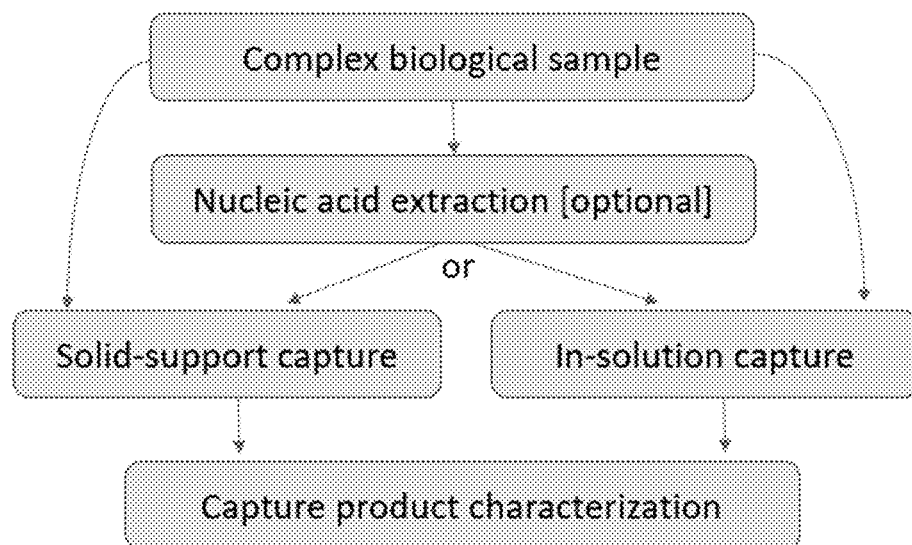
FIG. 20 illustrates various processes used in conjunction with hybridization capture.

As shown in FIG. 20, hybridization capture can be carried out in solution or on a solid support. In "solid-phase," DNA probes are bound to a solid support, such as a glass microarray slide (Albert et al. (2007). Direct selection of human genomic loci by microarray hybridization. *Nat. Methods* 4, 903-905). In a "solution-capture," free DNA or RNA probes are biotinylated, allowing them to isolate the targeted fragment-probe heteroduplexes using magnetic streptavidin beads (Gnirke et al. (2009). Solution hybrid selection with ultra-long oligonucleotides for massively parallel targeted sequencing. *Nat. Biotechnol.* 27, 182-189). Alternatively, the capture can be carried out on the surface of a plastic tube by immobilized antibodies specific for RNA-DNA hybrids (Ferenczy et al. Diagnostic performance of Hybrid Capture human papillomavirus deoxyribonucleic acid assay combined with liquid-based cytologic study. *Am J Obstet Gynecol* 1996;175:651-656). The unreacted RNA probe is not immobilized on the tube surface and is therefore eliminated by washing. Detection of the hybrids is done with an alkaline phosphatase-conjugated RNA-DNA antibody, followed by incubation in a chemiluminescent substrate. Alternatively, an ultrashort qPCR can efficiently capture and amplify targeted cfDNA fragments (Oreskovic A, Lutz BR (2021) Ultrasensitive hybridization capture: Reliable detection of <1 copy/mL short cell-free DNA from large-volume urine samples. *PLoS ONE* 16(2):e0247851).

Figure 21:
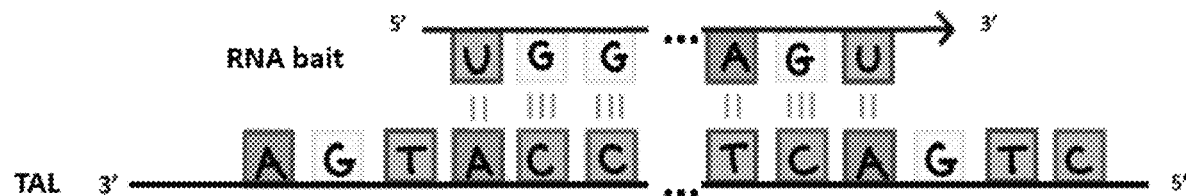
FIG. 21 illustrates the hybridization-based capture where a bait (or probe) is complementary to the nucleic acid sequence of a Transcriptionally Active Locus (TAL).

Hybridization-based capture requires a bait (or probe) that is complementary to the template region of DNA (FIG. 21). Similar to the primer design in PCR, capture baits should be optimally designed. Shorter baits produce inaccurate, non-specific DNA capture product, and long baits result in a slower hybridizing rate. The structure of the bait should be relatively simple and contain no internal secondary structure to avoid internal folding. Bait design involves cfDNA fragment count and length consideration.

Figure 22:
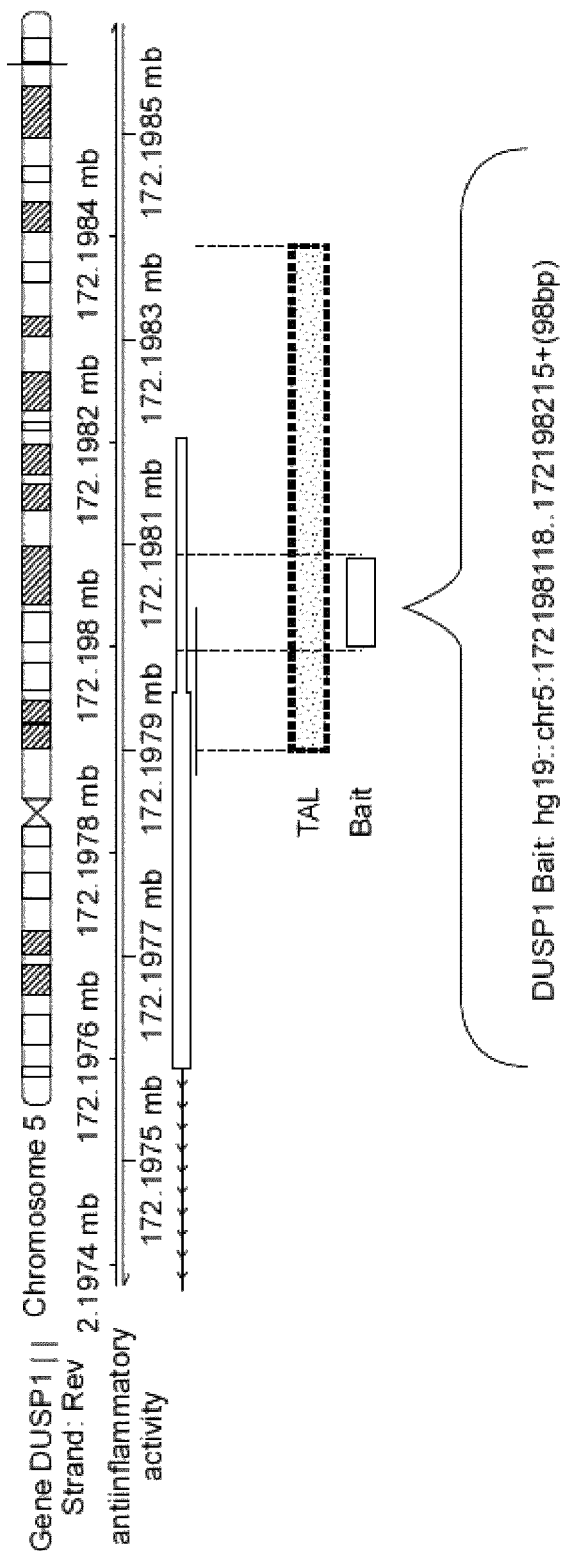
FIG. 22 illustrates an exemplary bait for capturing cfNA fragments associated with the TAL of DUSP1.
Figure 23:
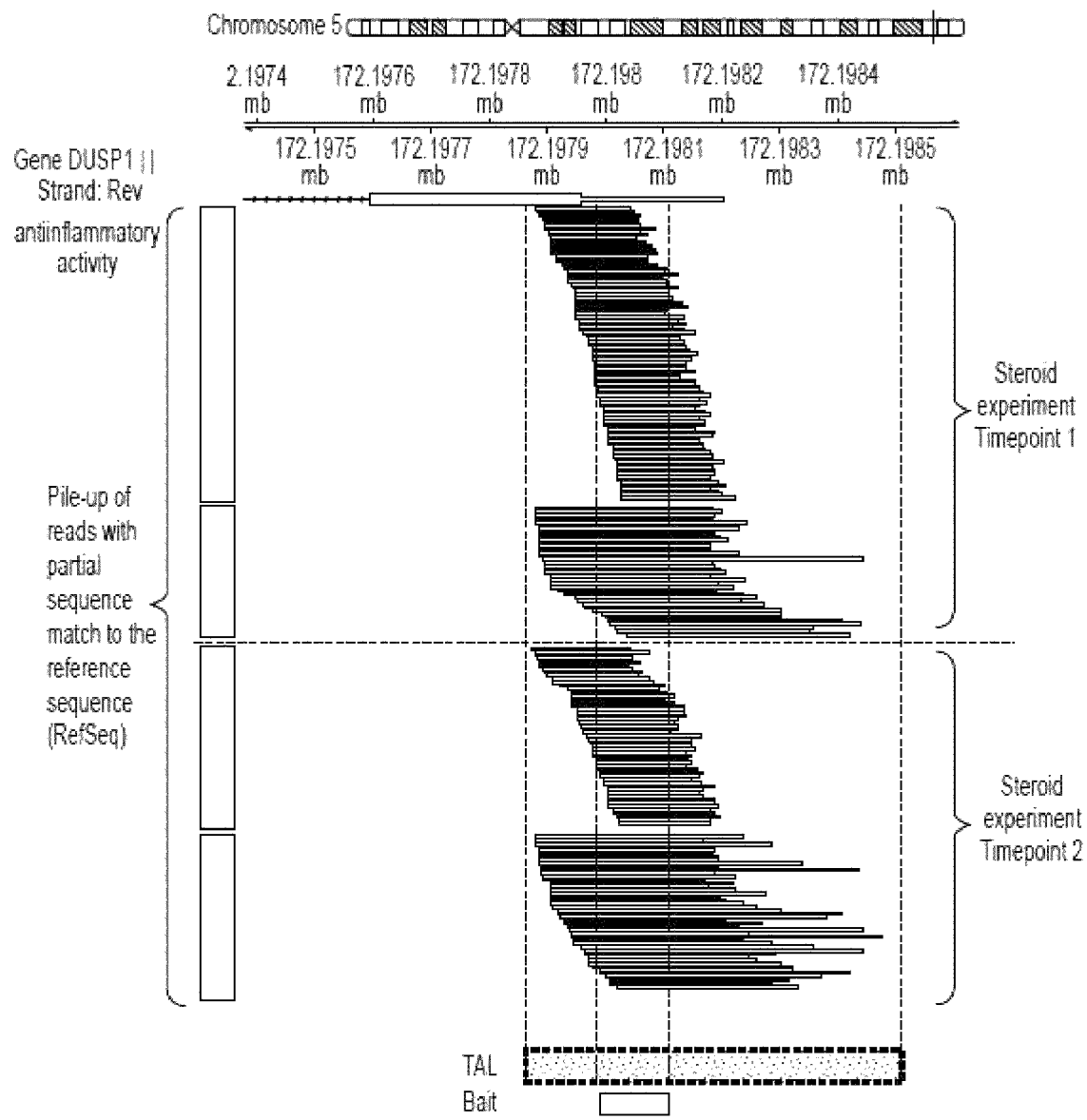
FIG. 23 illustrates a simulation wherein cfNA fragments derived from the TAL of DUSP1 are captured by the exemplary bait.
Figure 24:
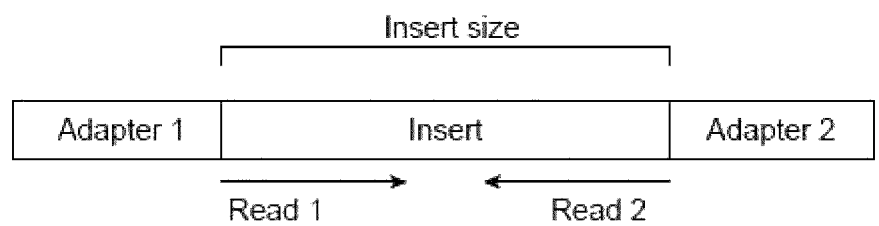
FIG. 24 illustrates a cfDNA fragment flanked by sequencing adapters. The length of sequence reads can be longer than the length of the cfDNA fragment.
Figure 25:
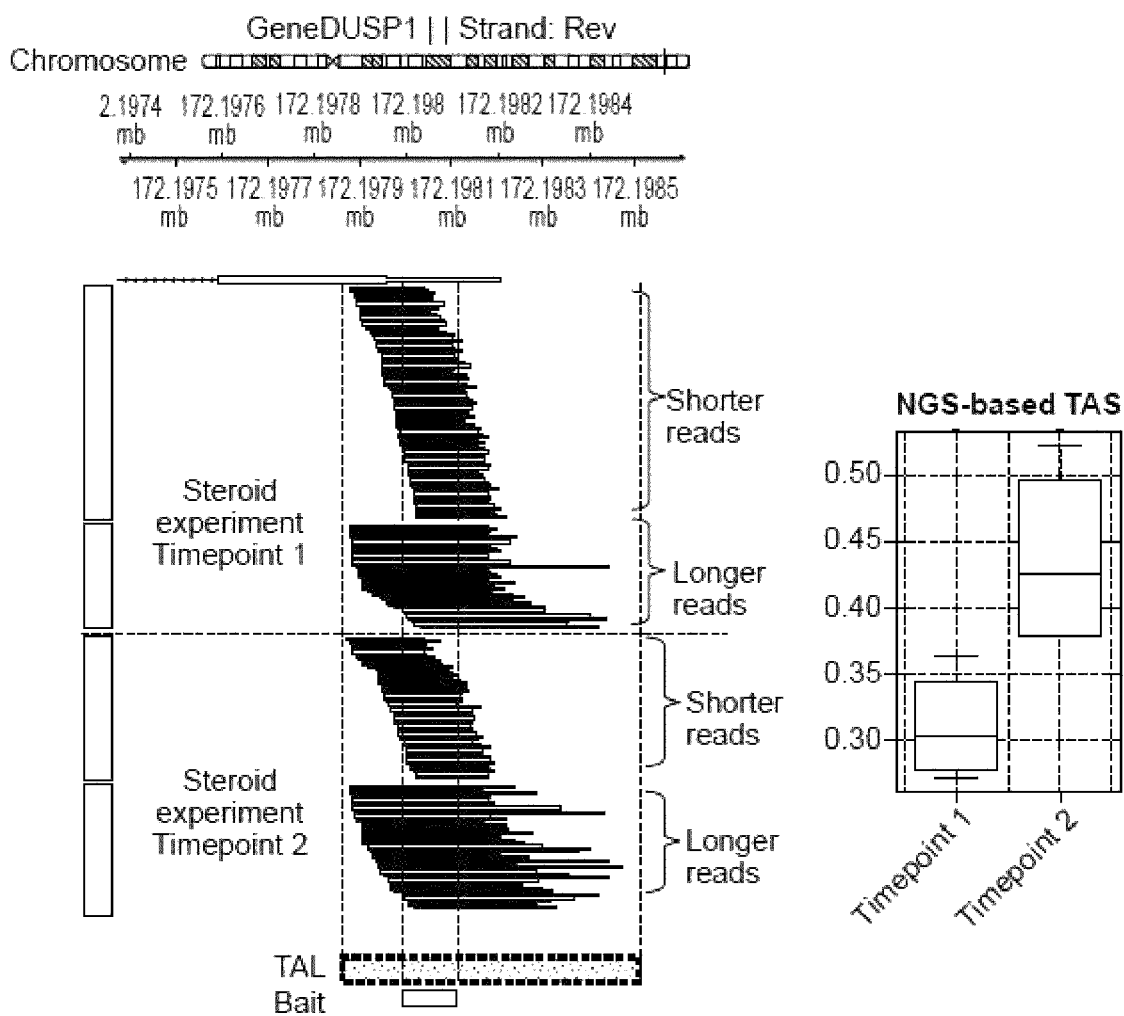
FIG. 25 illustrates a simulation wherein cfNA fragments derived from the TAL of DUSP1 are captured by the exemplary bait. The captured cfNA fragments at two timepoints are categorized into groups of long and short cfNA fragments. The right panel illustrates a TAS calculated from the fraction of long cfNA fragments.

FIG. 22 shows an example of a bait for hybridization capture of cfDNA derived from a transcriptionally active locus at the DUSPI promoter. FIG. 23 and FIG. 25 show all NGS sequence reads representing cfDNA fragments that could have been captured by the bait of FIG. 22 from a blood sample collected at timepoint 1 and a blood sample collected at timepoint 2. In FIGS. 23 and 25, the sequence reads are stratified based on cfDNA fragment length. Sequencing adapters were ligated to either end of the cfDNA, so its apparent length when measured by a Bioanalyzer is longer than the length of the isolated cfDNA fragments as shown in FIG. 24. The "shorter" reads have insert sizes of 140-200 bp and the "longer" reads have insert sizes of 270-400 bp. A TAS score was calculated from the fraction of longer peak concentration to total cfDNA concentration (sum of concentrations among shorter and longer peaks).

Figure 26:
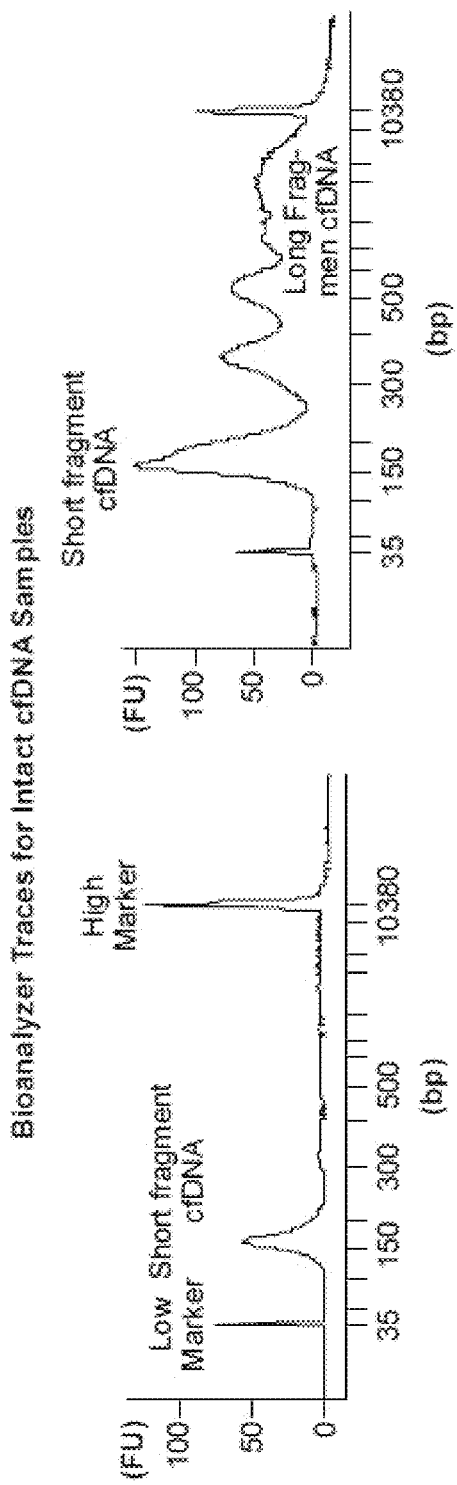
FIG. 26 illustrates Bioanalyzer traces of two cfNA samples. Both samples have a predominant peak of shorter cfDNA fragments at approximately 167 base pairs, which is the size of cfDNA fragments protected by a mononucleosome. The trace in the right has a higher fraction of long cfDNA fragments indicative of transcriptional activity.
Figure 27:
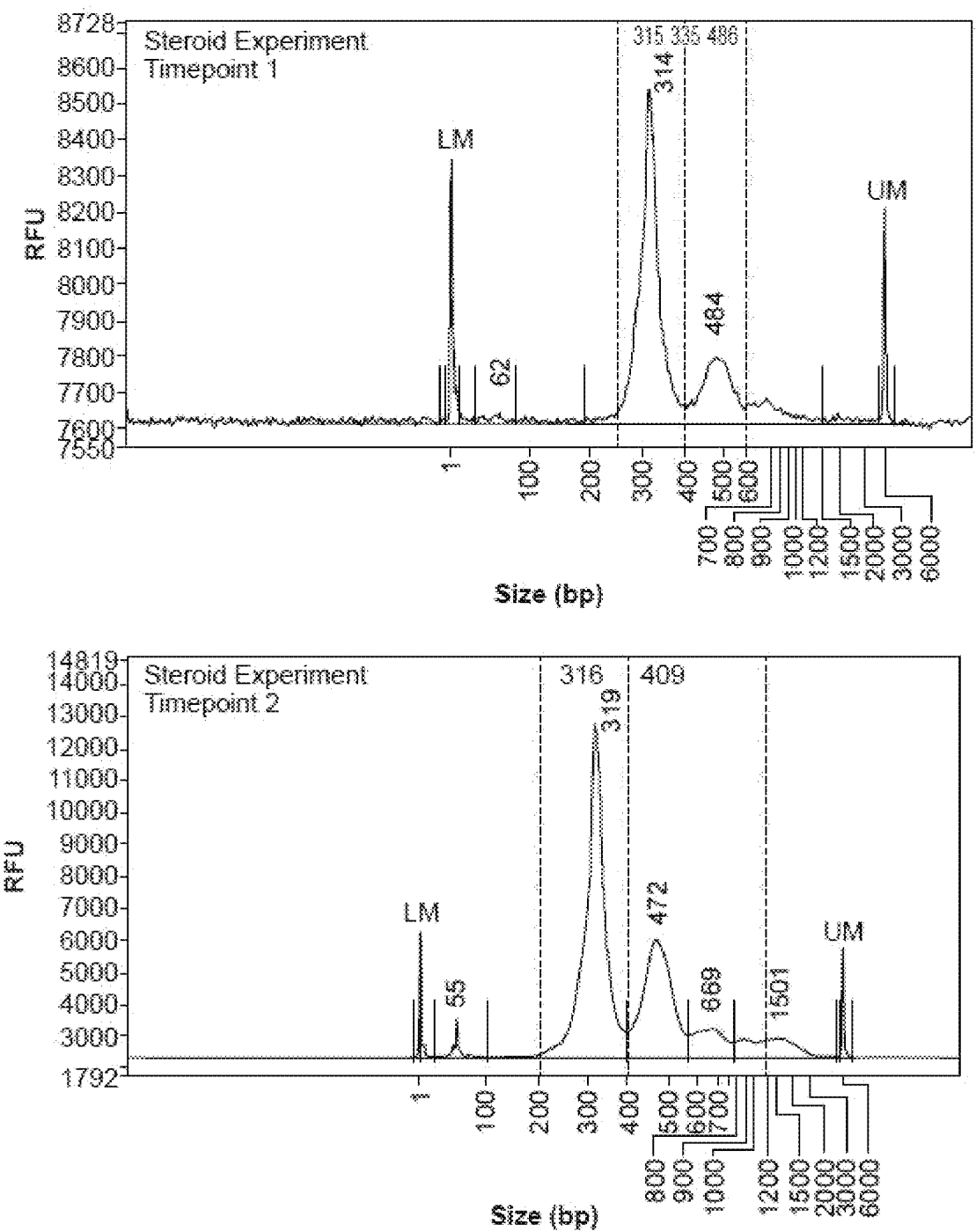
FIG. 27 illustrates Bioanalyzer traces of cfNA samples captured by the bait from the TAL of DUSP1. The mononucleosome peak is shifted right because the cfNA is flanked by sequencing adaptors. The fraction of long cfDNA fragments is higher at Timepoint 2.

Bioanalyzer, Tape station, Fragment Analyzer or other similar instruments can be used to assess the quality, length, and purity of cfDNA. FIG. 26 shows examples of appropriate traces. While not all cfDNA samples have identical size distributions, a typical trace shows a predominant short (mononucleosomal) cfDNA peak at approximately 167 base pairs. After the nucleic acids are separated by electrophoresis, they are normalized to a ladder and two DNA markers are then represented as a virtual band. The Bioanalyzer software then automatically calculates the size and concentration of each band. In the prednisone experiment, Agilent 2100 Bioanalyzer and High Sensitivity DNA Kit were used to assess the quantity, quality and size distribution of the enrichment products in steroid experiment according to the manufacturer's instructions (FIG. 27).

Figure 28A:
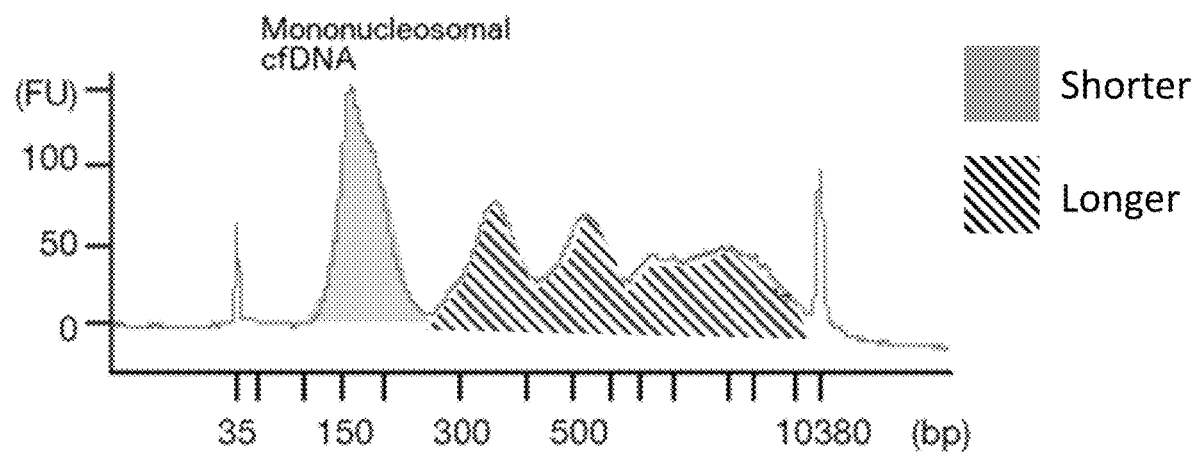
FIGS. 28A-B illustrate a method of distinguishing short and long fragments from a Bioanalyzer trace. The length of the short fragments is consistent with the size of DNA protected by a mononucleosome.
Figure 28B:
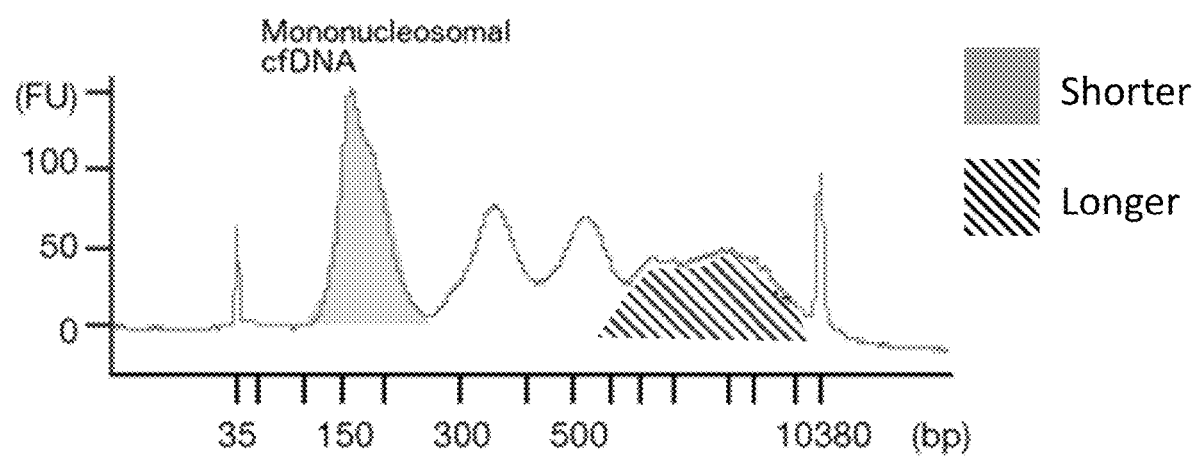
Figure 29:
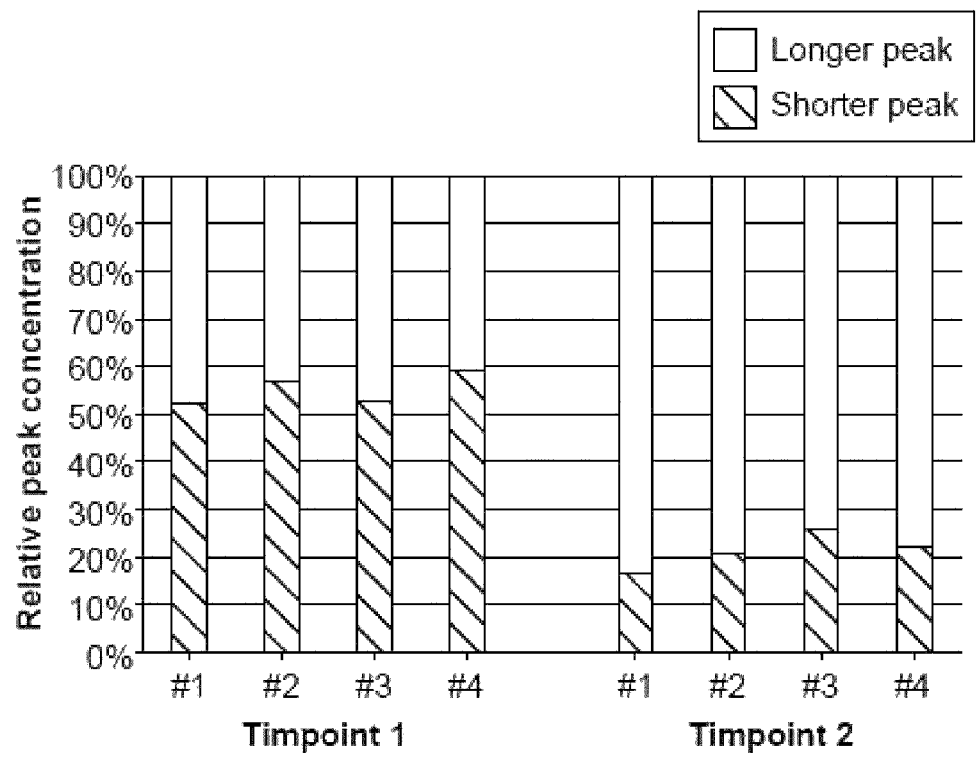
FIG. 29 illustrates transcriptional activation scores determined from cfDNA fragments captured by the bait. The increase in measured TAS at Timepoint 2 is consistent with expectations from the NGS simulation of FIG. 25.
Figure 29:
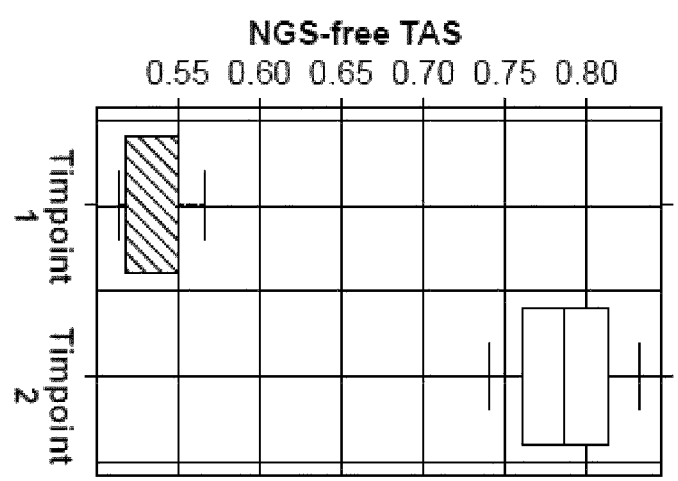
Figure 30A:
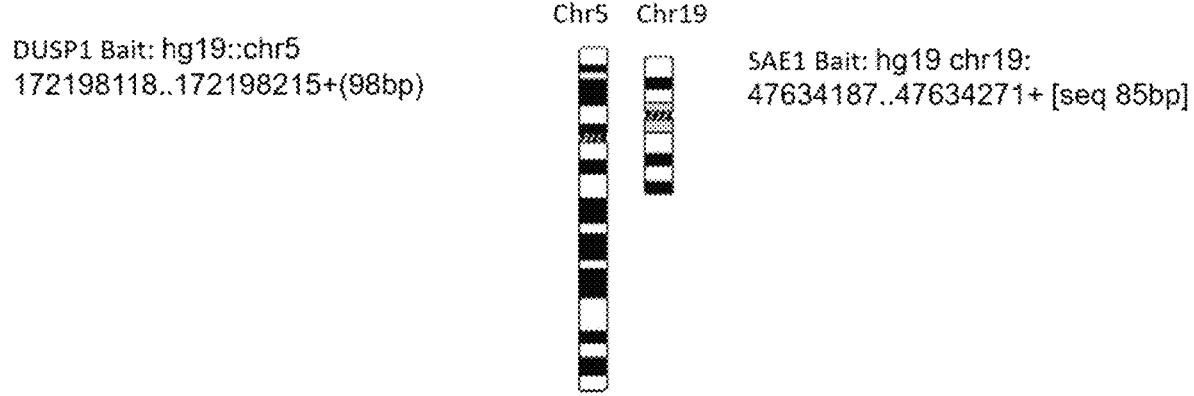
FIGS. 30A-D illustrates a two-bait system for capturing cfDNA derived from TALs associated with two genes involved in glucocorticoid metabolism—DUSP1 and SAE1.
Figure 30B:
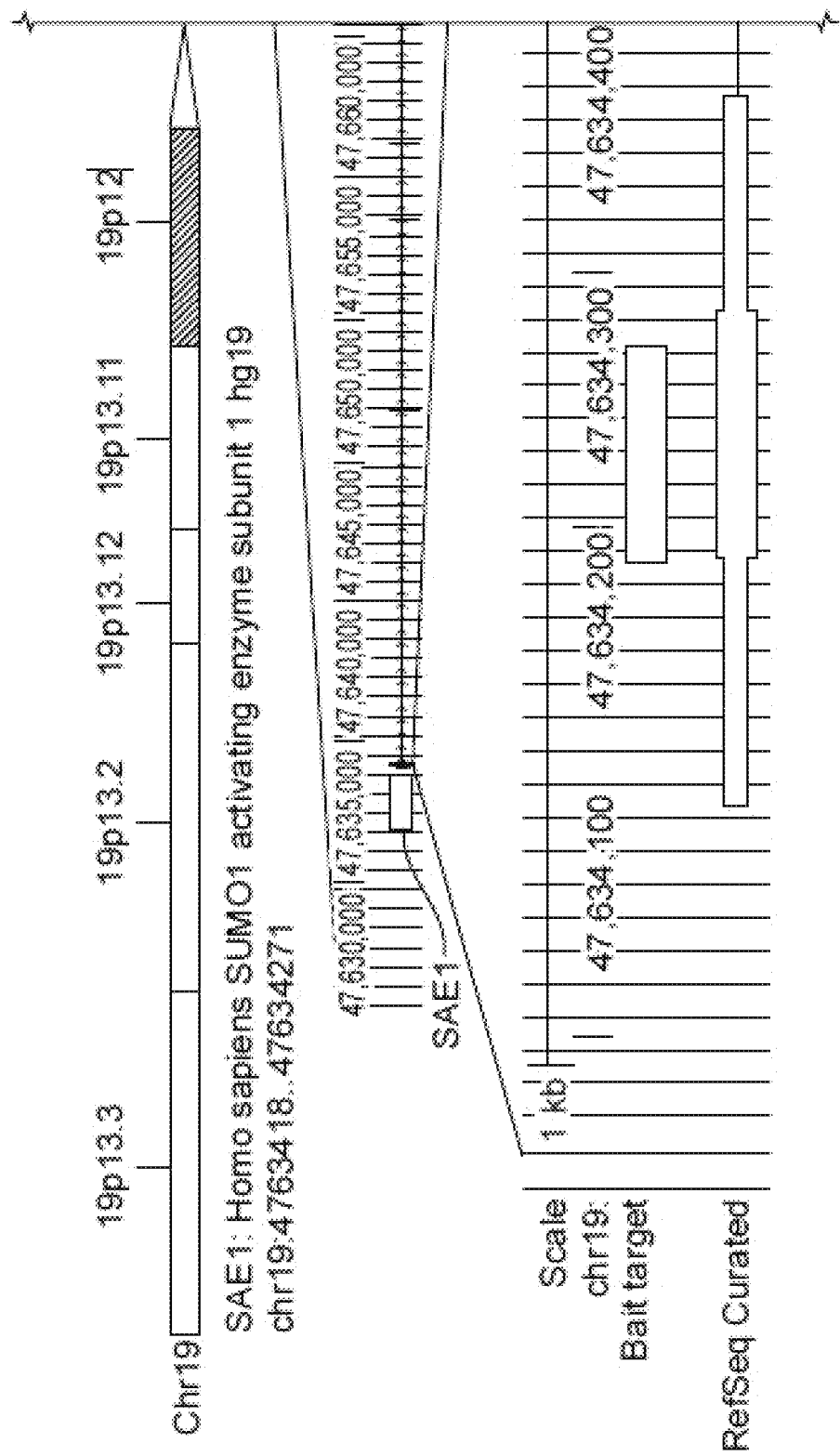
Figure 30B:
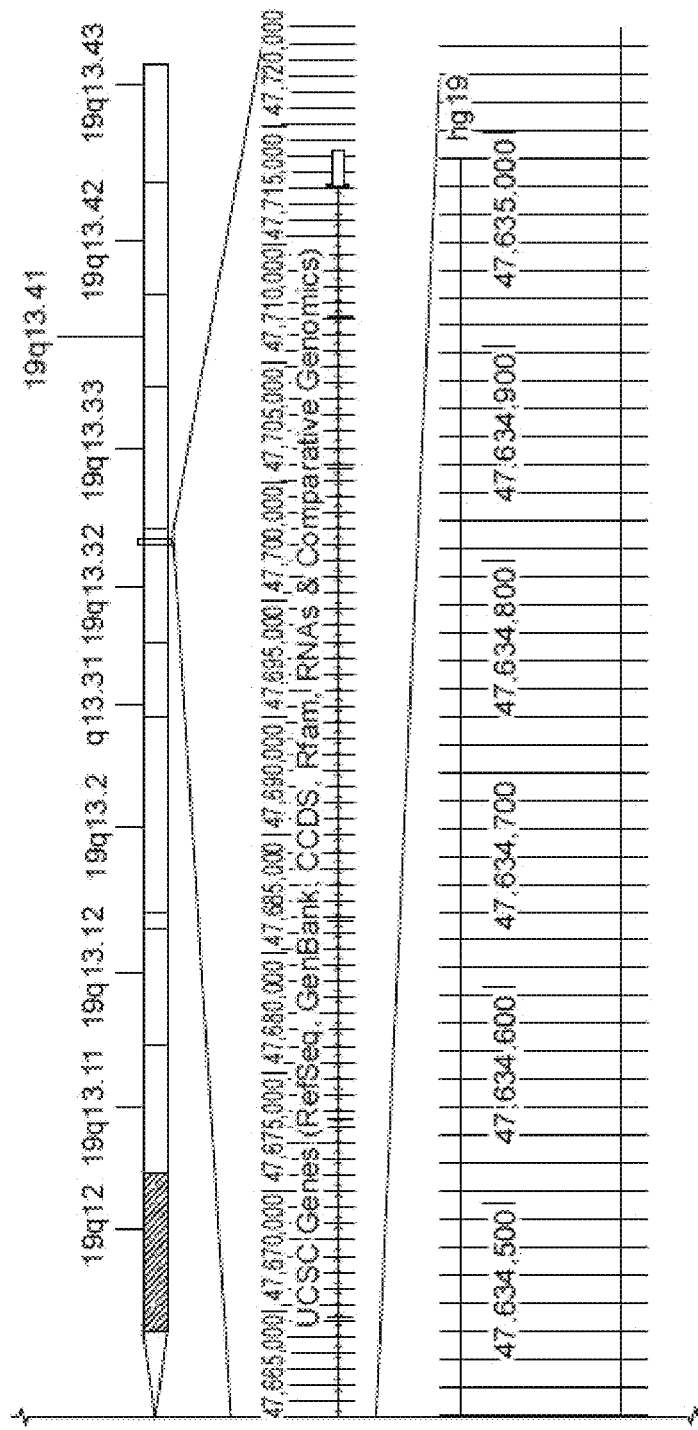
Figure 30C:
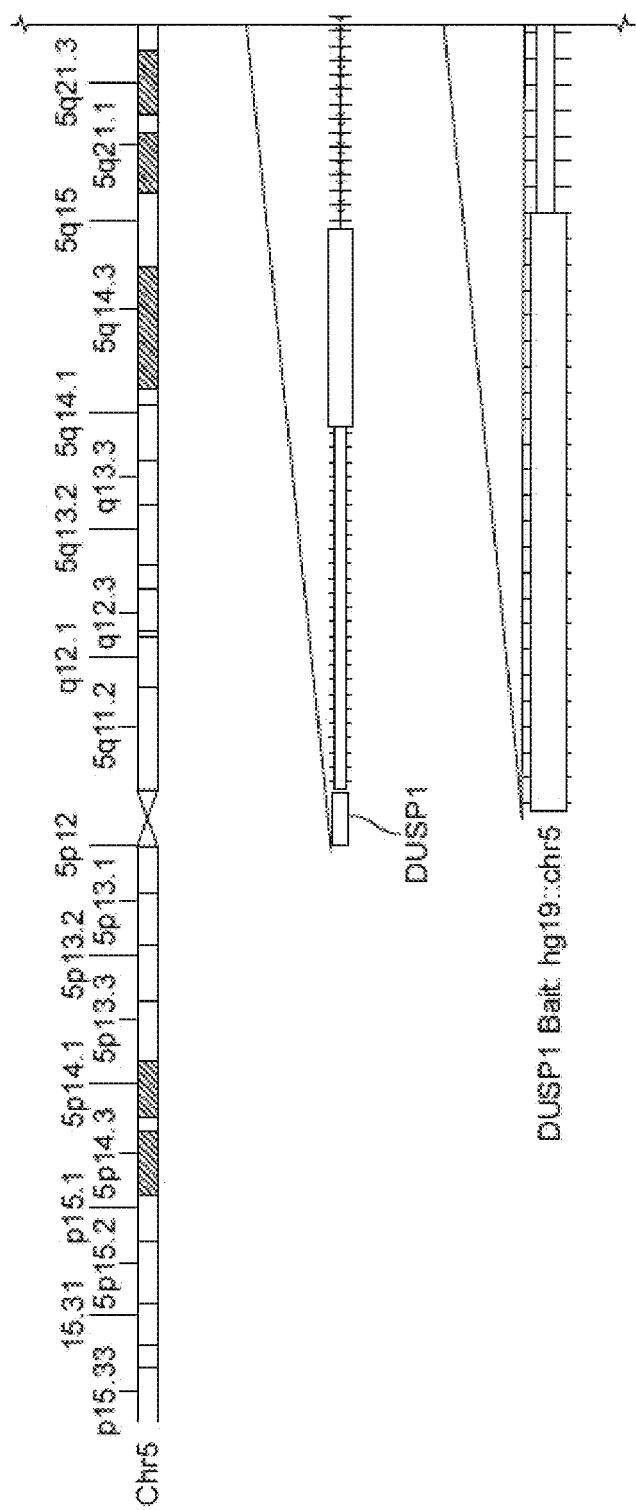
Figure 30C:
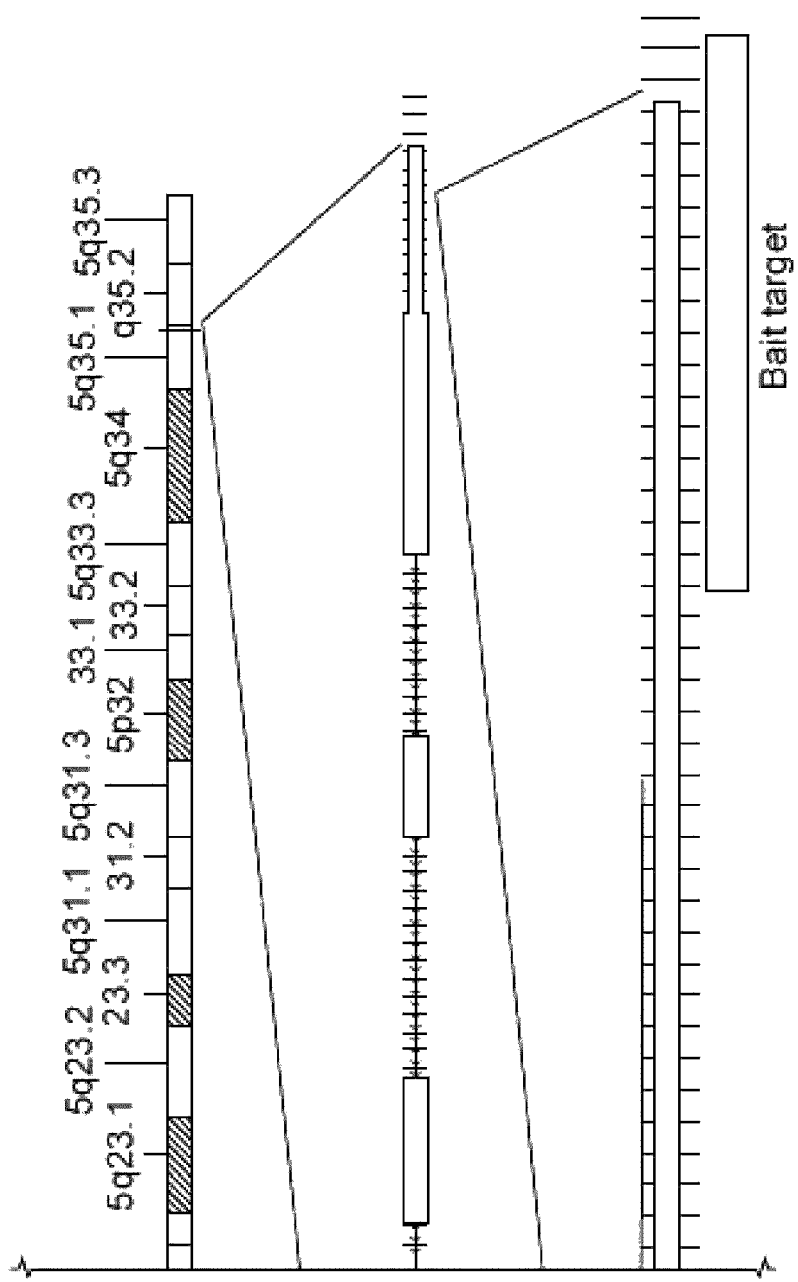
Figure 30D:
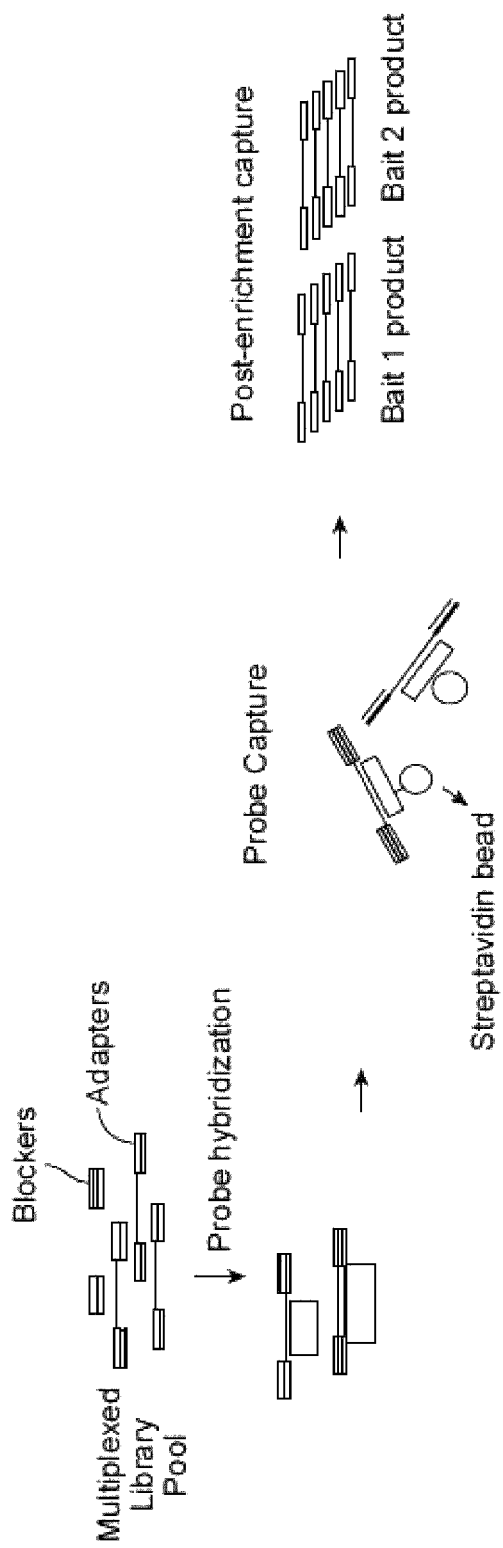

The fragment sizes of cfDNA and the concentrations for each peak in the electropherogram were determined by were determined with Agilent 2100 Bioanalyzer software. In some examples, the mononucleosome-protected cfDNA peak is categorized as short and all longer fragment cfDNA peaks are categorized as long (or non-canonical) as illustrated in FIG. 28A. In other examples, the mononucleosome-protected cfDNA peak is categorized as short and a specific peak(s) of cfDNA sizes is categorized as long as illustrated in FIG. 28B. Like the NGS-based analysis, a TAS score was defined as a fraction of longer peak concentration to total cfDNA concentration (sum of concentrations among shorter and longer peaks). In the steroid experiment, an NGS-free TAS score was produced for every blood draw (#1, #2, #3, and #4), and the measurements were compared. between timepoints, resulting in statistically significant change between timepoints (FIG. 29) consistent with the one observed in the simulated TAS analysis from NGS data (FIG. 25).

Alternative techniques can also be used to determine a cfDNA fragment length distribution. Size distributions can be measured by electrophoresis, imaging, and dye quantification. It can also be achieved via paired-end NGS sequencing that determines the insert size after aligning the reads to a reference. It can be also determined via single-end sequencing where the entirety of the NA fragment is base called and the number of the called nucleotides is equal to NA fragment length.

Figure 31:
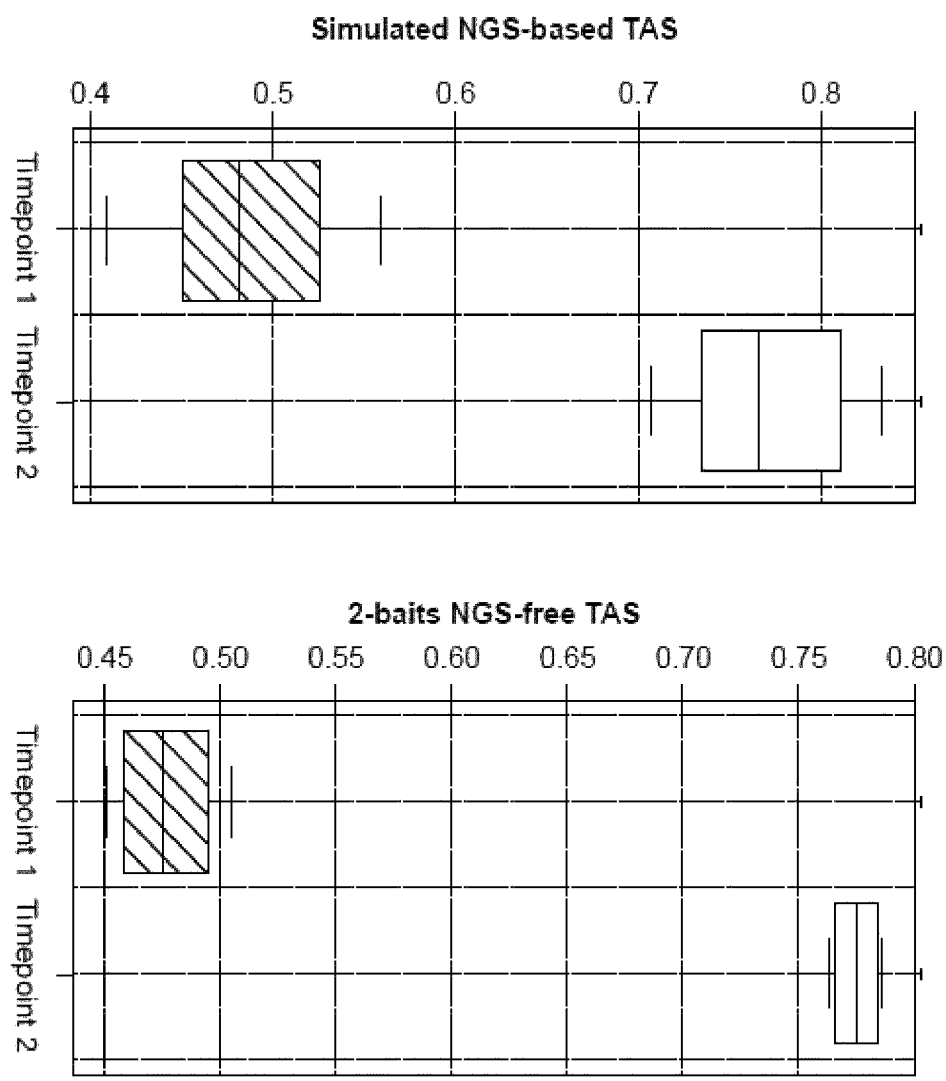
FIG. 31 compares simulated (NGS-based) and actual two-bait transcriptional activation scores using the two-bait system of FIG. 31 to analyze cfDNA isolated from glucocorticoid treatment experiment.
Figure 32:
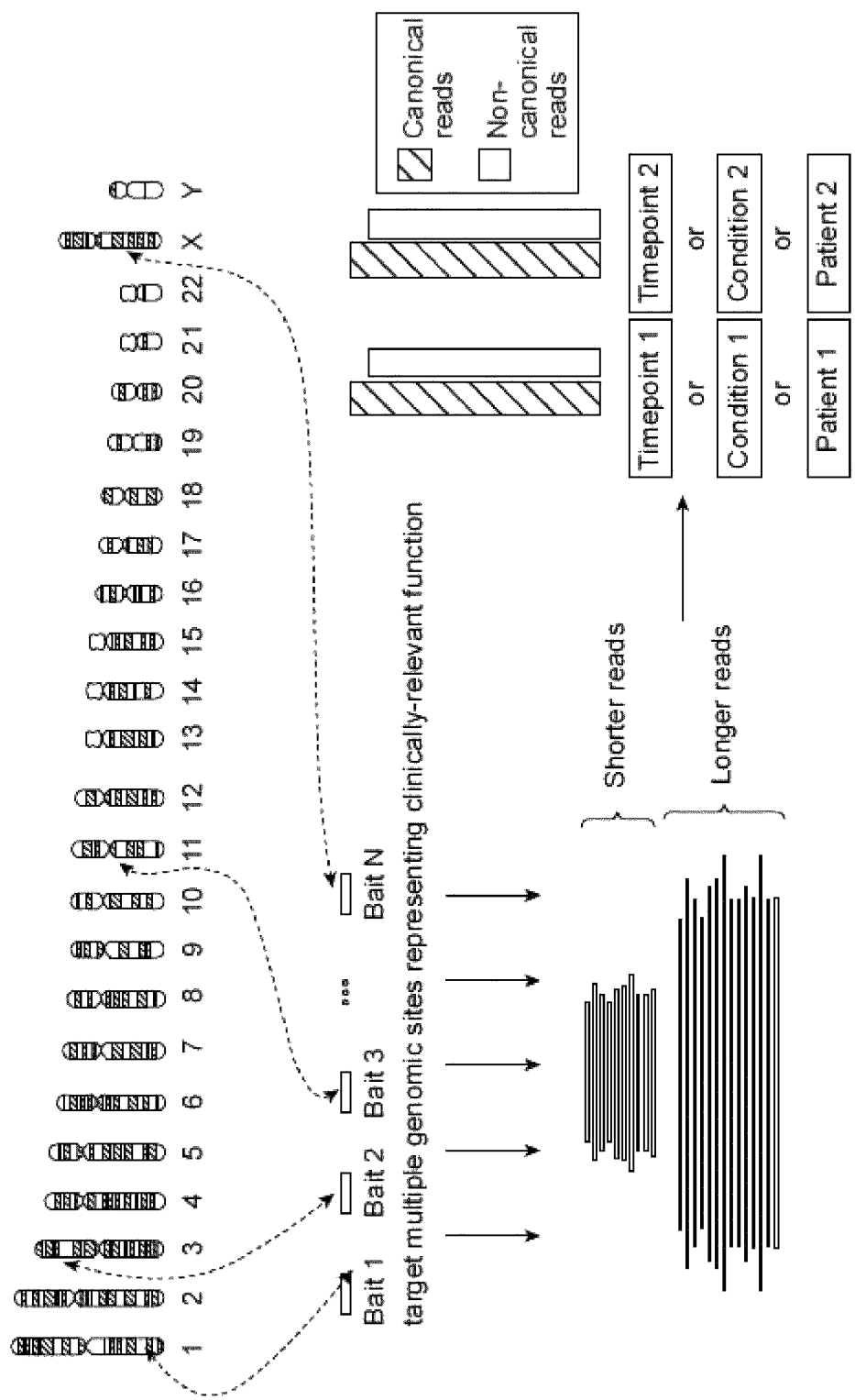
FIG. 32 illustrates an N-bait composite read-out system.

Next, a two-bait system, representing two distinct genomic loci mapped to two genes involved in glucocorticoid metabolism'DUSP1 and SAE1—was used to capture enrichment product in the same manner described above, see an expanded two-bait schematic in FIGS. 30A-D. Since both baits were mixed a single tube, a single NGS-free TAS value was generated to characterize the captured cfDNA from two genomic regions. FIG. 31 compares simulated results based on NGS data with actual results from hybridization capture experiments. In both methods, a significant difference was observed between timepoints. The two-bait system can be extended to an N-bait composite read-out system as shown in FIG. 32, where N is more than two. Also, hybridization capture using the SAE1 bait alone coupled to bioanalyzer analysis yielded TAS results consistent with the results for SUSP1 and the DUSP1/SAE1 pair.

Figure 33:
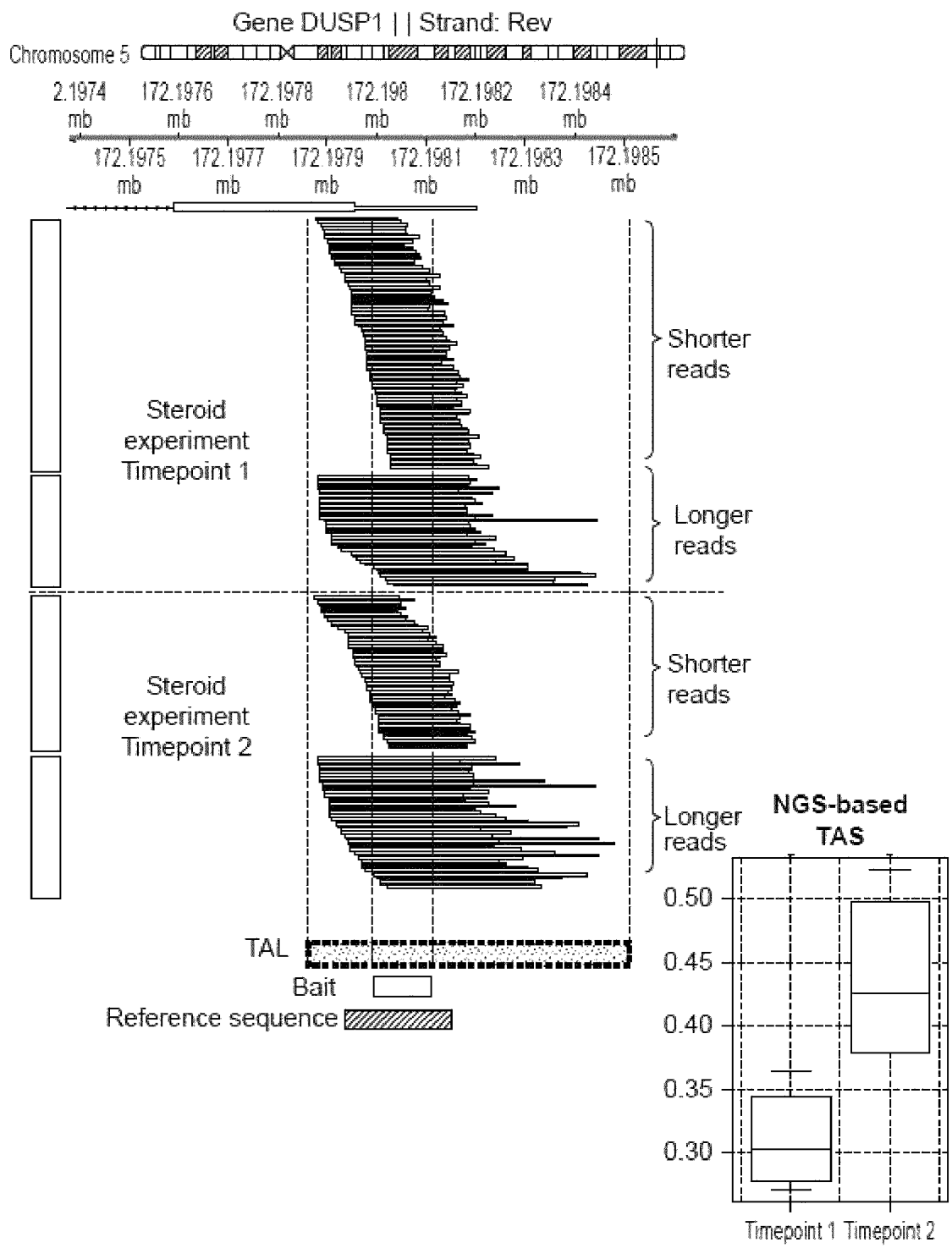
FIG. 33 illustrates a simulated example of characterizing cfDNA fragments that hybridize the bait by an alignment-free comparison of sequences of the cfDNA fragments to a reference sequence.
Figure 34:
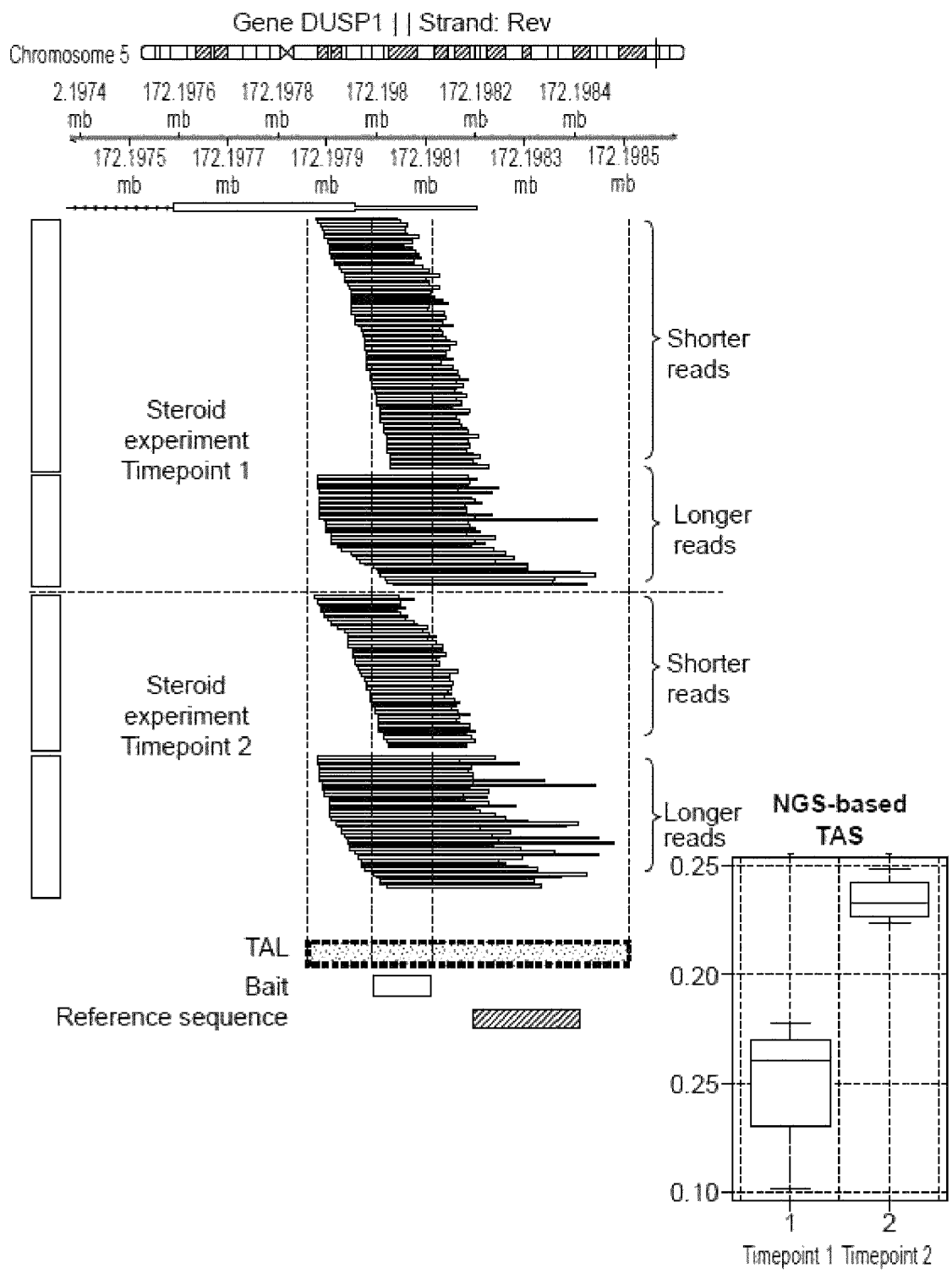
FIG. 34 illustrates a simulated example of quantifying a relative amount of cfDNA fragment sequences aligning to sequences distal to an end of a bait.
Figure 35:
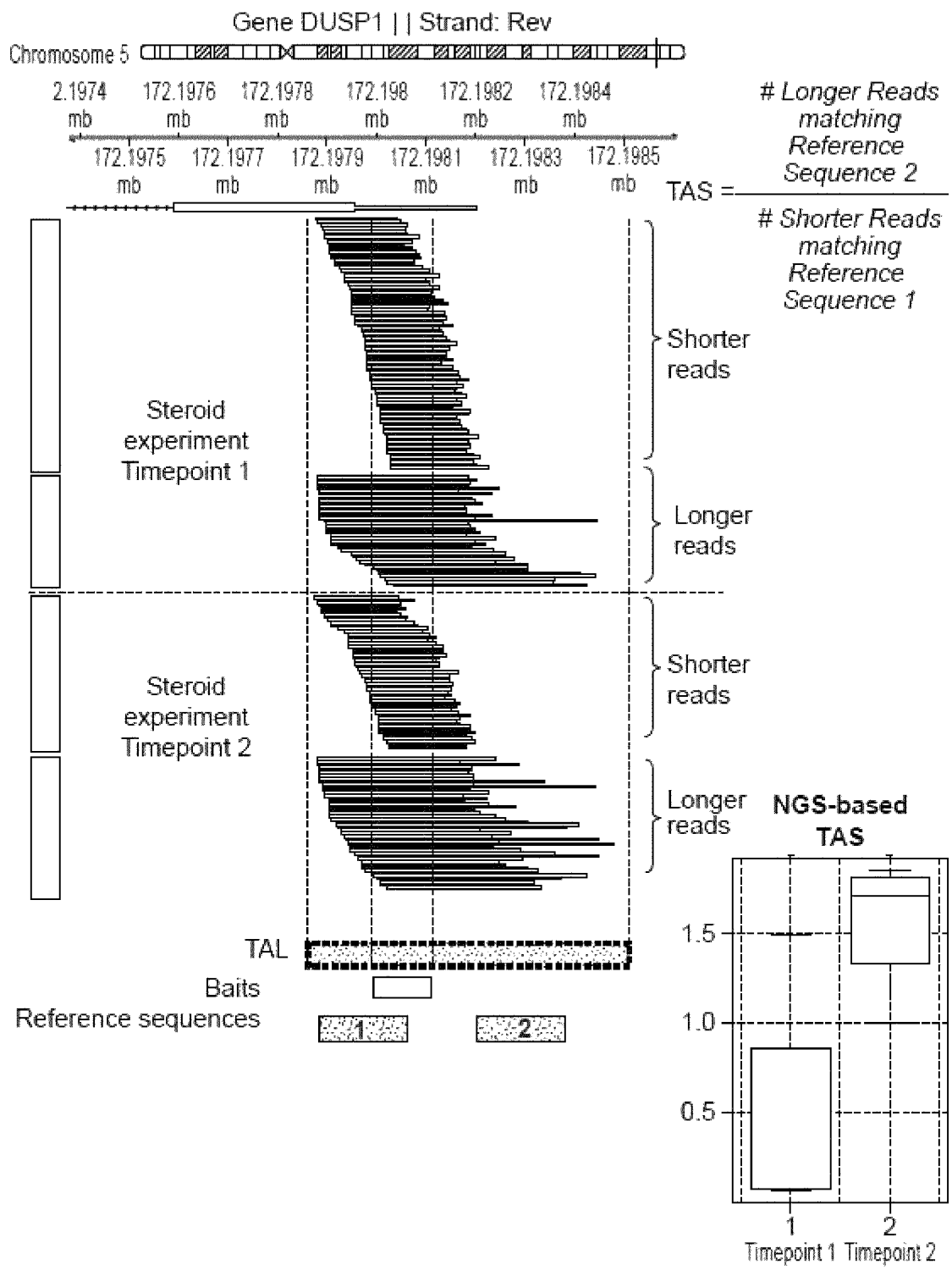
FIG. 35 illustrates a simulated example of characterizing cfDNA fragments that hybridize to a bait by counting a number of cfDNA fragments comprising a sequence matching each of two or more identified subregions within a transcriptionally active locus.
Figure 36:
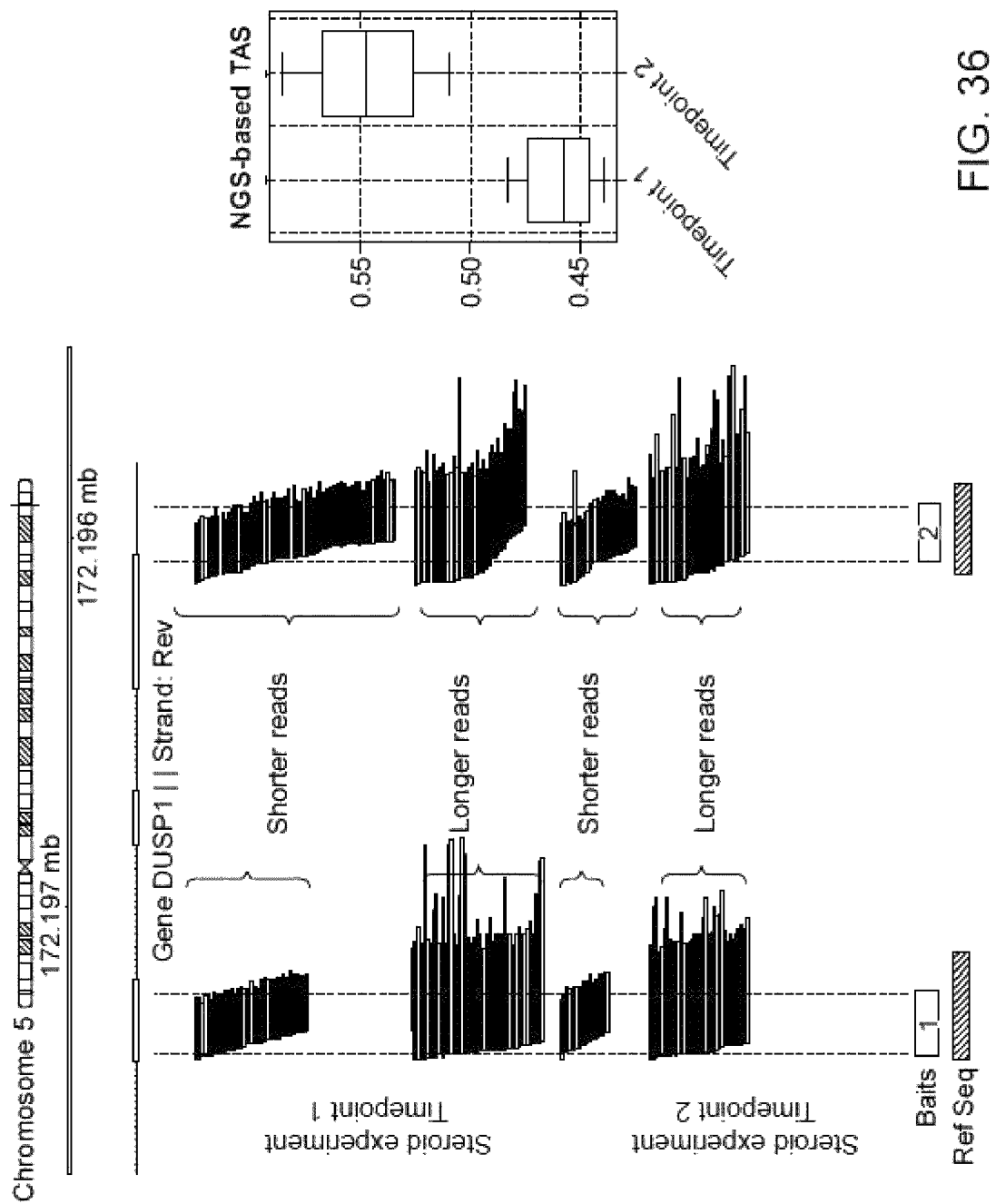
FIG. 36 illustrates a simulated example of characterizing cfDNA fragments that hybridize to two baits within one transcriptionally active locus.
Figure 37:
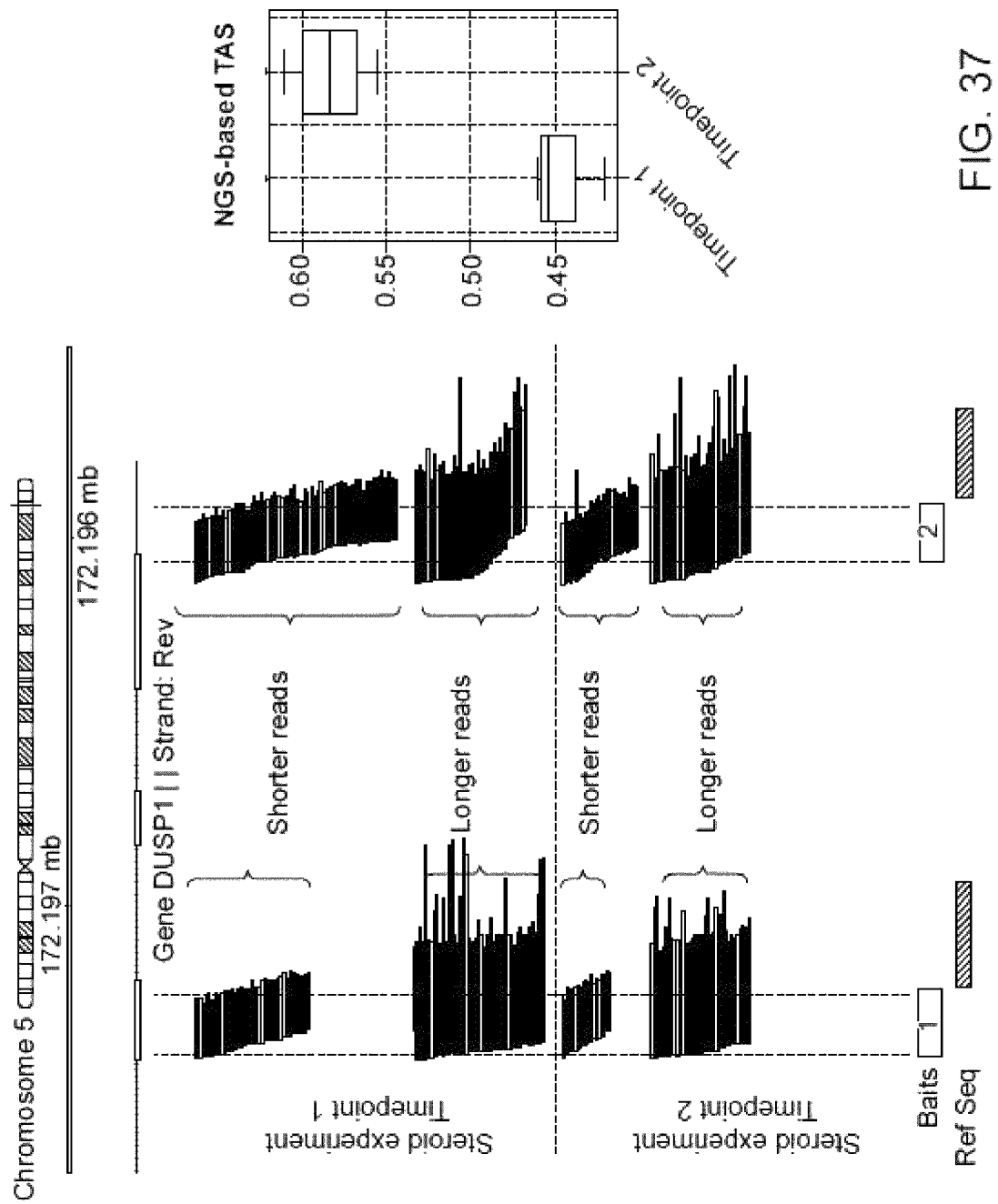
FIG. 37 illustrates a simulated example of characterizing cfDNA fragments that hybridize to two baits within one transcriptionally active locus with alignment free matching to reference sequences indicative of long cfDNA fragments.

FIG. 33, FIG. 34 and FIG. 35 shows simulated examples where cfDNA fragments derived from the DUSP1 promoter region are captured with the DUSP1 bait. The captured fragments are sequenced and then alignment free methods are used to identify fragments matching references overlapping the bait (FIG. 33), distal to the bait (FIG. 34) or two sequences representing different fragmentation patterns (FIG. 35). A simulated TAS is then determined based on the lengths of the matching fragments. In each case, the simulated transcriptional activation score indicates increased transcriptional activity at Timepoint 2. In some embodiments, a weighted score can be re-defined using parametric (such as linear regression), a non-parametric (such as artificial neural networks) models, e.g. an arbitrary ratio after the counts and size distributions for each reference sequence match are obtained.

To be counted as a match, a sequence read must have a continuous overlap of 40 bases with up to 1 mismatch permitted. Alternatively, matching can be performed using an edit distance, e.g. Levenshtein distance, that accounts for character insertions, deletions and substitutions. Edit distance is a string metric. This metric provides a manner for detecting the closeness of two strings to one another by identifying the minimum number of alterations that must occur to transform one string into the other.

Additional loci having statistically significant changes in TAS between timepoints were studied using NGS-free methods. For example, an ultramer RNA oligonucleotide of 85 bases (hg19 chr19: 47634187-47634271) was manufactured to target small ubiquitin-like modifier (SUMO) activating enzyme subunit 1 (SAE1).

cfDNA hybridizing to the SAE1 bait was captured from the eight cfDNA libraries representing the two timepoints in the prednisone experiment by overnight hybridization. Bait-target hybrids were bound to streptavidin-coated magnetic beads and sequestered with a magnet, while non-target cfDNA was washed away. Agilent 2100 Bioanalyzer and High Sensitivity DNA Kit were used to assess the quantity, quality and size distribution of enrichment products from the steroid experiment according to the manufacturer's instructions. The fragment sizes of the cfDNAs (+sequencing adaptors) were determined via Agilent 2100 Bioanalyzer software.

Transcriptional activation scores (TAS) calculated as previously described revealed a statistically significant change between timepoints consistent with the results for the DUSP1locus and simulated changes observed by NGS-derived TAS analysis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Non-Limiting List of Exemplary Embodiments

In addition to the aspects and embodiments described and provided elsewhere in this disclosure, the following non-limiting list of particular embodiments are specifically contemplated.

1. A method of characterizing cell-free nucleic acid (cfNA) fragments derived from a genomic region, comprising:
   a) contacting a composition comprising cfNA with an oligonucleotide bait comprising a sequence complementary to a sequence of the genomic region, and
   b) characterizing a fragmentation pattern of the cfNA fragments that hybridize to the oligonucleotide bait,
   wherein characterizing the fragmentation pattern does not comprise identifying genomic locations of the cfNA fragments or determining fragment lengths from the genomic locations of the cfNA fragments.

2. The method of embodiment 1, wherein the oligonucleotide bait is conjugated to an affinity tag.

3. The method of embodiment 2, wherein the affinity tag is biotin.

4. The method of embodiment 1, wherein the oligonucleotide bait is conjugated to a solid surface.

5. The method of embodiment 4, wherein the solid surface is a bead.

6. The method of embodiment 4, wherein the solid surface is a planar surface.

7. The method of any of embodiments 1-6, wherein the cfNA fragments are cell-free deoxyribonucleic acid (cfDNA) fragments 8. The method of any of embodiments 1-7, wherein the cfNA fragments are cell-free ribonucleic acid (cfRNA) fragments.

9. The method of any of embodiments 1-8, wherein characterizing the fragmentation pattern of the cfNA fragments comprises analyzing sizes or abundances of the cfNA fragments.

10. A method of characterizing cfNA fragments derived from a genomic region, comprising:
    a) contacting a composition comprising cfNA with an oligonucleotide bait, and
    b) analyzing abundance of the cfNA fragments that hybridize to the oligonucleotide bait,
    wherein the oligonucleotide bait comprises a sequence complementary to a sequence of the genomic region,
    wherein analyzing abundance of the cfNA fragments comprises sequencing the cfNA fragments and performing an alignment-free sequence comparison of the cfNA fragment nucleotide sequences to a reference sequence, and
    wherein the genomic region comprises the reference sequence.

11. A method of characterizing cfNA fragments derived from a genomic region, comprising:
    a) contacting a composition comprising cfNA with an oligonucleotide bait, and
    b) analyzing sizes of cfNA fragments that hybridize to the oligonucleotide bait,
    wherein the oligonucleotide bait comprises a sequence complementary to a sequence of the genomic region.

12. The method of embodiment 11, wherein analyzing sizes of the cfNA fragments comprises performing an electrophoretic separation.

13. The method of embodiment 12, wherein the electrophoretic separation comprises gel or capillary electrophoresis.

14. The method of embodiment 12, wherein the electrophoretic separation comprises microfluidic separation of cfNA fragments.

15. The method of any of embodiments 11-14, wherein the method comprises comparing mobilities of cfNA fragments to a known standard.

16. The method of embodiment 11, wherein analyzing sizes of the cfNA fragments comprises
   i. stretching the cfNA fragments, and
   ii. acquiring an image of the cfNA fragments.

17. The method of embodiment 11, wherein analyzing sizes of the cfNA fragments comprises capturing an end of a cfNA fragment in an optical trap or flow-stretching a cfNA fragment.

18. The method of embodiment 11, wherein analyzing sizes of the cfNA fragments comprises:
   i. contacting the cfNA fragments with a dye,
   ii. separating the cfNA fragments into droplets,
   iii. flowing the droplets past a detector,
   iv. measuring the fluorescence of each cfNA fragment, and
   v. calculating a size from the fluorescence intensity, wherein fluorescence of the dye is enhanced by contact with the cfNA fragments.

19. The method of any of embodiments 11-18, further comprising comparing an amount of long cfNA fragments comprising at least 230 nucleotides to an amount of short cfNA fragments comprising less than 230 nucleotides.

20. The method of embodiment 19, wherein the long cfNA fragments comprise at least 255, 270, 185 or 310 nucleotides.

21. The method of embodiment 19 or embodiment 20, wherein the short cfNA fragments comprise less than 220, 205, 190, or 175 nucleotides.

22. The method of any of embodiments 19-21, wherein an increased abundance of long cfNA fragments is indicative of a medical condition.

23. The method of embodiment 22, wherein a ratio of long cfNA fragments to short cfNA fragments of at least 0.01, 0.05, 0.1, 0.2, 0.25, 0.3, 0.35 or 0.4 is indicative of a medical condition.

24. A method of characterizing cfNA fragments derived from a genomic region, comprising:
   a) contacting a composition comprising cfNA with an oligonucleotide bait, and
   b) sequencing cfNA fragments that hybridize to the oligonucleotide bait and
   c) performing an alignment-free sequence comparison of the cfNA fragment nucleotide sequences to a reference sequence,
   wherein the oligonucleotide bait comprises a bait sequence complementary to a sequence of the genomic region, and wherein the genomic region comprises the reference sequence.

25. The method of embodiment 23, further comprising:
   quantifying a relative amount of cfNA fragment sequences aligning to sequences distal to a first end of the oligonucleotide bait versus cfNA fragment sequences aligning to sequences distal to a second end of the oligonucleotide bait.

26. A method of characterizing cfNA fragments derived from a genomic region, comprising:
   a) contacting a composition comprising cfNA with an oligonucleotide bait, and
   b) sequencing cfNA fragments that hybridize to the oligonucleotide bait and
   c) identifying two or more subregions within the genomic region:
   d) counting a number of cfNA fragments comprising a sequence matching each subregion, wherein the oligonucleotide bait comprises a sequence complementary to a sequence of the genomic region.

27. The method of embodiment 26, wherein a cfNA fragment matches a subregion if:
   a) a sequence of the fragment is identical to the sequence of the subregion, or
   b) a sequence of the fragment is assigned to the subregion via approximate string matching.

28. A method of characterizing cfNA fragments derived from a genomic region, comprising:
   a) contacting a composition comprising cfNA with a first oligonucleotide bait and a second oligonucleotide bait,
   b) analyzing the cfNA fragments that hybridize to the first oligonucleotide bait, and
   c) analyzing the cfNA fragments that hybridize to the second oligonucleotide bait,
   wherein the first oligonucleotide bait and the second oligonucleotide bait comprise sequences complementary to sequences of the genomic region, and
   wherein the method does not comprise identifying genomic locations or lengths of the cfNA fragments.

29 The method of embodiment 28, further comprising comparing the cfNA fragments that hybridize to the first bait with cfNA fragments that hybridize to the second bait.

30. The method of any of embodiment 28 or embodiment 29, wherein the first oligonucleotide bait and the second oligonucleotide bait are conjugated to an affinity tag.

31. The method of embodiment 30 wherein the affinity tag is biotin.

32. The method of any of embodiments 28-31, wherein the first oligonucleotide bait and the second oligonucleotide bait are conjugated to a solid surface.

33. The method of embodiment 32, wherein the solid surface is a bead.

34. The method of embodiment 32, wherein the solid surface is a planar surface.

35. The method of any of embodiments 10-34, wherein the cfNA fragments are cell-free deoxyribonucleic acid (cfDNA) fragments.

36. The method of any of embodiments 10-34, wherein the cfNA fragments are cell-free ribonucleic acid (cfRNA) fragments.

37. The method of any of embodiments 28-36, wherein analyzing the cfNA fragments that hybridize to the first oligonucleotide bait and the second oligonucleotide bait comprises measuring an amount of cfNA fragments that hybridize to the first oligonucleotide bait and an amount of cfNA fragments that hybridize to the second oligonucleotide bait.

38. The method of any of embodiments 28-36, wherein analyzing the cfNA fragments that hybridize to the first oligonucleotide bait and the second oligonucleotide bait comprises analyzing sizes of the cfDNA fragments.

39. The method of embodiment 38, wherein analyzing sizes of the cfDNA fragments comprises sequencing the cfNA fragments and performing alignment-free sequence comparison of the cfNA fragment nucleotide sequences to a reference sequence,
   wherein the genomic region comprises the reference sequence.

40. The method of embodiment 38, wherein analyzing sizes of the cfDNA fragments comprises performing electrophoresis.

41. The method of embodiment 40, wherein the electrophoresis is gel or capillary electrophoresis.

42. The method of any of embodiment 37, wherein analyzing sizes of the cfDNA fragments comprises microfluidic separation of cfNA fragments.

43. The method of any of embodiments 40-42, wherein the method further comprises comparing the mobilities of cfNA fragments to a known standard.

44. The method of any of embodiment 38, wherein analyzing sizes of the cfNA fragments comprises
   a) stretching the cfNA fragments, and
   b) acquiring an image of the cfNA fragments.

45. The method of embodiment 44, wherein stretching the cfNA fragments comprises capturing an end of a cfNA fragment in an optical trap or flow-stretching a cfNA fragment.

46. The method of any of embodiment 38, wherein the cfNA is cfDNA, and wherein analyzing sizes of the cfDNA fragments comprises:
   a) contacting the cfDNA fragments with a dye,
   b) separating the cfDNA fragments into droplets,
   c) flowing the droplets past a detector,
   d) measuring the fluorescence of each cfDNA fragment, and
   e) inferring fragment size from the fluorescence intensity, wherein fluorescence of the dye is enhanced by contact with the cfDNA fragments.

47. The method of any of embodiments 38-46, further comprising comparing an amount of long cfNA fragments comprising at least 230 nucleotides to an amount of short cfNA fragments comprising less than 230 nucleotides.

48. The method of embodiment 47, wherein the long cfNA fragments comprise at least 255, 270, 185 or 310 nucleotides.

49. The method of embodiment 47 or embodiment 48, wherein the short cfNA fragments comprise less than 220, 205, 190, or 175 nucleotides.

50. The method of any of embodiments 47-49, wherein an increased abundance of long cfNA fragments is indicative of a medical condition.

51. The method of embodiment 50 wherein a ratio of long cfNA fragments to short cfNA fragments of at least 0.2, 0.25, 0.3, 0.35 or 0.4 is indicative of a medical condition.

52. The method of any of embodiments 28-36, wherein analyzing cfNA fragments that hybridize to the first oligonucleotide bait and the second oligonucleotide bait comprises sequencing the cfNA fragments and performing alignment-free sequence comparison of the cfNA fragment nucleotide sequences to a reference sequence, wherein the genomic region comprises the reference sequence.

53. The method of any of embodiments 28-36, further comprising
   a) quantifying a relative amount of cfNA fragment sequences aligning to sequences distal to a first end of the first oligonucleotide bait versus cfNA fragment sequences aligning to sequences distal to a second end of the first oligonucleotide bait:
   b) quantifying a relative amount of cfNA fragment sequences aligning to sequences distal to a first end of the second oligonucleotide bait versus cfNA fragment sequences aligning to sequences distal to a second end of the second oligonucleotide bait.

54. A method of characterizing cfNA fragments derived from a genomic region, comprising:
   a) collecting a first set of cfNA fragments from a biological sample by hybridization capture with a first oligonucleotide bait comprising a sequence complementary to a first sequence of the genomic region;
   b) collecting a second set of cfNA fragments from a biological sample by hybridization capture with a second oligonucleotide bait comprising a sequence complementary to a second sequence of the genomic region; and
   c) comparing the first set of cfNA fragments and second set of cfNA fragments,
   wherein characterizing the fragmentation pattern does not comprise identifying genomic locations or lengths of the first set of cfNA fragments or the second set of cfNA fragments.

55. The method of embodiment 54, wherein the first oligonucleotide bait and the second oligonucleotide bait are conjugated to affinity tags.

56. The method of embodiment 55, wherein the affinity tags are biotin.

57. The method of embodiment 54, wherein the first oligonucleotide bait and the second oligonucleotide bait are conjugated to a solid surface.

58. The method of embodiment 57, wherein the solid surface is a bead.

59. The method of embodiment 57, wherein the solid surface is a planar surface.

60. The method of any of embodiments 54-59, wherein the cfNA fragments are cfDNA fragments 61. The method of any of embodiments 54-60, wherein the cfNA fragments are cfRNA fragments.

62. The method of any of embodiments 54-61, wherein characterizing the fragmentation pattern of the cfNA fragments comprises analyzing sizes or abundances of the cfNA fragments.

63. A method of characterizing cfNA fragments derived from a genomic region, comprising
   a) collecting a first set of cfNA fragments from a biological sample by hybridization capture with a first oligonucleotide bait comprising a sequence complementary to a first sequence of the genomic region;
   b) collecting a second set of cfNA fragments from a biological sample by hybridization capture with a second oligonucleotide bait comprising a sequence complementary to a second sequence of the genomic region; and
   c) analyzing abundance of the first set of cfNA fragments and the second set of cfNA fragments.

64. The method of embodiment 63, wherein analyzing abundance of the cfNA fragments comprises sequencing the cfNA fragments and performing alignment-free sequence comparison of the cfNA fragments nucleotide sequences to a reference sequence, wherein the genomic region comprises the reference sequence.

65. A method of characterizing cfNA fragments derived from a genomic region, comprising:
   a) collecting a first set of cfNA fragments from a biological sample by hybridization capture with a first oligonucleotide bait comprising a sequence complementary to a first sequence of the genomic region;
   b) collecting a second set of cfNA fragments from a biological sample by hybridization capture with a second oligonucleotide bait comprising a sequence complementary to a second sequence of the genomic region; and
   c) analyzing sizes of the first set of cfNA fragments and the second set of cfNA fragments.

66. The method of embodiment 65, wherein analyzing sizes of the cfNA fragments comprises performing an electrophoretic separation.

67. The method of embodiment 66, wherein the electrophoretic separation comprises gel or capillary electrophoresis.

68. The method of embodiment 66, wherein the electrophoretic separation comprises microfluidic separation of cfNA fragments.

69. The method of any of embodiments 65-68, wherein the method comprises comparing mobilities of cfNA fragments to a known standard.

70. The method of embodiment 65, wherein analyzing sizes of the cfDNA fragments comprises
a) stretching the cfNA fragments, and
b) acquiring an image of the cfNA fragments.

71. The method of embodiment 65, wherein analyzing sizes of the cfNA fragments comprises capturing an end of a cfNA fragment in an optical trap or flow-stretching a cfNA fragment.

72. The method of embodiment 65, wherein analyzing sizes of the cfNA fragments comprises:
a) contacting the cfNA fragments with a dye,
b) separating the cfNA fragments into droplets,
c) flowing the droplets past a detector,
d) measuring the fluorescence of each cfNA fragment, and
e) calculating a size from the fluorescence intensity,
f) wherein fluorescence of the dye is enhanced by contact with the cfNA fragments.

73. The method of any of embodiments 65-72, further comprising
a) comparing an amount of large cfNA fragments comprising at least 230 nucleotides to an amount of short cfNA fragments comprising less than 230 nucleotides for the first set of cfNA fragments; and
b) comparing an amount of long cfNA fragments comprising at least 230 nucleotides to an amount of short cfNA fragments comprising less than 230 nucleotides for the second set of cfNA fragments.

74. The method of embodiment 73, wherein the long cfNA fragments comprise at least 255, 270, 185 or 310 nucleotides.

75. The method of embodiment 73 or embodiment 74, wherein the short cfNA fragments comprise less than 220, 205, 190, or 175 nucleotides.

76. The method of any of embodiments 73-75, wherein an increased abundance of long cfNA fragments in the first set of cfDNA fragments is indicative of a medical condition.

77. The method of embodiment 76 wherein a ratio of long cfNA fragments to short cfNA fragments of at least 0.2, 0.25, 0.3, 0.35 or 0.4 the first set of cfNA fragments is indicative of a medical condition.

78. A method of characterizing cfNA fragments derived from a genomic region, comprising:
a) collecting a first set of cfNA fragments from a biological sample by hybridization capture with a first oligonucleotide bait comprising a sequence complementary to a first sequence of the genomic region;
b) collecting a second set of cfNA fragments from a biological sample by hybridization capture with a second oligonucleotide bait comprising a sequence complementary to a second sequence of the genomic region;
c) sequencing the first set of cfDNA fragments and the second set of cfDNA fragments; and
d) performing alignment-free sequence comparison of the cfNA fragment nucleotide sequences to a reference sequence, wherein the genomic region comprises the reference sequence.

79. The method of embodiment 78, further comprising: quantifying a relative amount of cfNA fragment sequences aligning to sequences distal to an end of the first oligonucleotide bait versus cfNA fragment sequences aligning to sequences distal to a second end of the first oligonucleotide bait.

80. A method of characterizing cfNA fragments derived from a genomic region, comprising:
a) collecting a first set of cfNA fragments from a biological sample by hybridization capture with a first oligonucleotide bait comprising a sequence complementary to a first sequence of the genomic region;
b) collecting a second set of cfNA fragments from a biological sample by hybridization capture with a second oligonucleotide bait comprising a sequence complementary to a second sequence of the genomic region;
c) sequencing the first set of cfNA fragments and the second set of cfNA fragments;
d) identifying two or more subregions within the genomic region; and
e) counting a number of cfNA fragments matching each subregion.

81. The method of embodiment 80, wherein a cfNA fragment matches a subregion if:
a sequence of the fragment is identical to the sequence of the subregion, or
a sequence of the fragment is assigned to the subregion via approximate string matching.

82. A method of characterizing cfNA fragments derived from a genomic region, comprising comparing an amount the cfNA fragments that comprise a first portion of the genomic region with an amount of the cfNA fragments that comprise a second portion of the genomic region.

83. The method of embodiment 82, wherein the amounts of the cfNA fragments that comprise the first portion and the second portion of the genomic region are determined by a method comprising amplification of the portions of the genomic region.

84. The method of embodiment 83, wherein the amplification is performed by PCR, loop mediated isothermal amplification, nucleic acid sequence-based amplification, strand displacement amplification, or multiple displacement amplification.

85. A method of characterizing cfNA fragments derived from a genomic region, comprising:
a) sequencing the cfNA fragments derived from the genomic region; and
b) comparing an amount of cfNA fragment sequences matching a first set of reference sequences representing a first fragmentation pattern to an amount of cfNA fragment sequences matching a second set of reference sequences representing a second fragmentation pattern.

86. The method of embodiment 85, wherein the cfNA fragment sequences matching the first and second sets of reference sequences are identified by alignment-free sequence comparisons.

87. The method of any of embodiments 1-86, wherein the composition comprising cfNA is plasma, serum, saliva, urine, blood components, cerebrospinal fluid, pleural fluid, amniotic fluid, peritoneal fluid, ascitic fluid, abdominopelvic washings/lavage, serous effusions, tracheobronchial or bronchoalveolar lavage.

88. The method of embodiment 87, wherein the composition comprising cfNA is plasma.

89. The method of any of embodiments 1-88, wherein the genomic region comprises at least one nucleotide of a promotor, a transcriptional start site, a DNase I-hypersensitive site, a Pol II pausing site, a first exon, or an intron to exon boundary.

90. The method of embodiment 89, wherein the genomic region comprises a first exon.

91. The method of embodiment 89, wherein the genomic region comprises an active transcriptional start site.

92. The method of any one of embodiments 1-91, wherein expression or post-cell death fragmentation of the genomic region is altered in a medical condition.

93. A method of characterizing cfNA fragments comprising:
   a) enriching a population of long cfNA fragments from a biological sample, and
   b) comparing an amount of the long cfNA fragments to a reference.

94. The method of embodiment 93, wherein the cfNA fragments are long cfNA fragments.

95. The method of embodiment 93 or embodiment 94, wherein the long cfNA fragments are derived from a genomic region.

96. The method of any of embodiments 94-95, the long cfNA fragments comprise at least 190, at least 200, at least 210, at least 220, at least 230, at least 240, or at least 250 contiguous nucleotides.

97. The method of any of embodiments 93-96, wherein the biological sample is plasma or serum.

98. The method of any of embodiments 93-97, wherein enriching a population of long cfNA fragments from a biological sample comprises contacting the biological sample with one or more different oligonucleotide baits to yield captured cfNA fragments.

99. The method of embodiment 98, wherein the one or more different oligonucleotide baits comprise an oligonucleotide bait with a sequence complementary to the sequence of a genomic region protected by a DNA-binding protein.

100. The method of embodiment 99, wherein the DNA-binding protein is not a histone.

101. The method of any of embodiments 98-100, wherein enriching a population of long cfNA fragments from a biological sample further comprises performing an electrophoretic separation on the captured cfNA fragments.

102. The method of embodiment 93, wherein comparing an amount of the long cfNA fragments to a reference comprises comparing an amount of long cfNA fragments captured by the one or more oligonucleotide baits to a total amount of cfNA fragments captured by the one or more oligonucleotide baits.

103. The method of any one of embodiments 93-102, wherein comparing the amount of the long cfNA fragments to a reference comprises measuring an amount of the captured cfNA fragments.

104. The method of any one of embodiment 93-103, wherein comparing an amount of the long cfNA fragments to a reference comprises sequencing the long cfNA fragments and matching the long cfNA fragments to a reference sequence comprising less than 1000 nucleotides.

105. The method of any one of embodiment 93-104, wherein enriching a population of long cfNA fragments from a biological sample comprises amplifying a segment of the long cfNA fragments.

106. A method of analyzing a cfNA fragmentation pattern comprising characterizing cfNA fragments derived from two or more genomic regions according to the methods of embodiments 1-105.

107. The method of any one of embodiments 1-106, wherein the genomic region comprises a start site or first exon of a steroid responsive gene.

108. The method of embodiment 107, wherein the steroid responsive gene is a glucocorticoid responsive gene, an anti-inflammatory gene, or a neutrophil activation signature gene.

109. The method of embodiment 108, wherein the glucocorticoid responsive gene is FKBP5, ECHDC3, IL1R2 or ZBTB16.

110. The method of embodiment 108, wherein the anti-inflammatory gene is DUSP1, TSC22D3, IRAK3, or CD163.

111. The method of embodiment 108, wherein the neutrophil activation signature gene is BCL2 or MCL1.

112. The method of any one of embodiments 1-111, wherein the genomic region comprises a start site or first exon of a vascular marker gene or an angiogenesis gene.

113. The method of embodiment 112, wherein the vascular marker gene is an endothelial cell marker gene, a pericyte marker gene or an integrin gene.

114. The method of embodiment 113, wherein the endothelial cell marker gene is PECAM1, CDH5, VWF, or EPHB4.

115. The method of embodiment 113, wherein the pericyte marker gene is CSPG4, ACTA2, or DES.

116. The method of embodiment 113, wherein the integrin gene is ITGAV or ITGB3.

117. The method of embodiment 112, wherein the angiogenesis gene is a vessel destability gene, a vessel stability gene, or a notch family gene.

118. The method of embodiment 117, wherein the vessel destability gene is HIF1AN, VEGFA, PGF, FLT1, KDR, NR4A1, FGF2, FGFR1, or FGFR2.

119. The method of embodiment 117, wherein the vessel stability gene is ANGPT1, ANGPT2, TEK, PDGFB, PDGFRB, TGFB1, TGFBR1, or ENG.

120. The method of embodiment 117, wherein the notch family gene is NOTCH1, NOTCH3, DLL4, or JAG1.

121. The method of any one of embodiments 1-120, wherein the genomic region is selected from first 5 exons of EphB4 gene.

122. A method of evaluating a medical condition in a subject comprising characterizing a fragmentation pattern of cfNA fragments derived from a genomic region according to the method of any one of embodiments 1-121.

123. A method of adaptive immunotherapy for the treatment of cancer in a subject comprising:
   a) administering a first course of a first immunotherapy compound to the subject;
   b) acquiring a longitudinal cell-free DNA fragmentation profile for one or more genes associated with angiogenesis and/or vasculogenesis from the subject; and
   c) administering a second course of immunotherapy to the subject; wherein the second course of immunotherapy comprises:
   i. a second immunotherapy compound if the cell-free DNA fragmentation profile is indicative of an insufficient response to the first immunotherapy compound; or
   ii. a second course of the first immunotherapy compound if the cell-free DNA fragmentation profile is not indicative of an insufficient response to the first immunotherapy compound.

124. The method of embodiment 123, wherein the cancer is lung cancer, melanoma, gastrointestinal carcinoid tumor, colorectal cancer or pancreatic cancer.

125. The method of embodiment 123 or embodiment 124, wherein acquiring a longitudinal cell-free DNA fragmentation profile comprising acquiring a first biological sample from the subject at a T0 time-point prior to administering a first dose of the first course of the first immunotherapy compound and acquiring one or more biological samples from the subject after administering the first dose of the first course of the first immunotherapy compound.

126. The method of embodiment 125, wherein the one or more biological samples acquired after administering the first dose of the first course of the first immunotherapy compound are acquired on the same day that a dose of the of the first course of the first immunotherapy compound is administered.

127. The method of any one of embodiments 123-126, wherein the cell-free DNA fragmentation profile comprises sizes of DNA fragments derived from enhancers, promoters, first exons or promoter-proximal transcriptional pause sites of the one or more genes associated with angiogenesis and/or vasculogenesis.

128. The method of embodiment 127, wherein an increase over time of large cell-free DNA fragments derived from enhancers, promoters, first exons or promoter-proximal transcriptional pause sites of the one or more genes associated with angiogenesis and/or vasculogenesis is indicative of an insufficient response to the first immunotherapy compound.

129. The method of any one of embodiments 123-128, wherein the first immunotherapy compound and the second immunotherapy compound are selected from the group consisting of pembrolizumab, nivolumab, atezolizumab, durvalumab, and avelumab.

130. A method of treating a medical condition in a subject comprising: administering a course of therapy to the subject, and acquiring a longitudinal cell-free DNA fragmentation profile of one or more genomic regions from the subject;
    wherein the a longitudinal cell-free DNA fragmentation profile indicates that the subject has responded to the course of therapy.

131. A method of treating a medical condition in a subject comprising:
    acquiring a cell-free DNA fragmentation profile of one or more genomic regions from the subject; and
    administering a course of therapy to the subject,
    wherein the cell-free DNA fragmentation profile indicates that the course of therapy is indicated for the subject.

132. A method of characterizing cfNA fragments derived from at least two genomic regions comprising a first genomic region and a second genomic region, comprising:
    a) contacting a composition comprising cfNA with a first oligonucleotide bait comprising a sequence complementary to a sequence of the first genomic region,
    b) contacting the composition with a second oligonucleotide bait comprising a sequence complementary to a sequence of the second genomic region,:
and
    c) analyzing abundance, size and sequence context of the cfNA fragments that hybridize to the at least two oligonucleotide baits.

133. The method of embodiment 132, wherein the first oligonucleotide bait enriches a population of small cfNA fragments from the composition and the second oligonucleotide bait enriches a population of long cfNA fragments from the composition.

134. The method of embodiment 132 or 133, further comprising contacting the composition with a third oligonucleotide bait comprising a sequence complementary to a sequence of the first genomic region.

135. The method of embodiment 134, wherein the third oligonucleotide bait enriches a population of small cfNA fragments from the composition.

136. The method of any of embodiments 132-135, further comprising contacting the composition with a fourth oligonucleotide bait comprising a sequence complementary to a sequence of the second genomic region.

137. The method of embodiment 136, wherein the fourth oligonucleotide bait enriches a population of long cfNA fragments from the composition.

138. The method of any of embodiments 132-137, wherein step (a) and step (b) occur simultaneously.

139. The method of any of embodiments 132-138, wherein the at least two genomic regions further comprises a third genomic region; wherein the method further comprises contacting the composition with a fifth oligonucleotide bait comprising a sequence complementary to a sequence of the third genomic region.

140. The method of embodiment 139, wherein the fifth oligonucleotide bait enriches a population of short cfNA fragments from the composition.

141. The method of embodiment 139 or embodiment 140, wherein the contacting the composition with the fifth oligonucleotide bait occur simultaneously with step (a) and step (b).

142. The method of any of embodiments 139-141, further comprising contacting the composition with a sixth oligonucleotide bait comprising a sequence complementary to a sequence of the third genome region.

143. The method of embodiment 142, wherein the sixth oligonucleotide bait enriches a population of long cfNA fragments from the composition.

144. The method of embodiment 141, wherein the contacting the composition with the sixth oligonucleotide bait occur simultaneously with contacting the composition with the fifth oligonucleotide bait, step (a), and step (b).

145. The method of any of embodiments 132-144, wherein the analyzing abundance, size and sequence context of the cfNA fragments does not comprise identifying genomic locations or lengths of the cfNA fragments.

146. The method of any of embodiments 132-145, wherein the first oligonucleotide bait, the second oligonucleotide bait, the third oligonucleotide bait, the fourth oligonucleotide bait, the fifth oligonucleotide bait, and/or the sixth oligonucleotide bait is conjugated to an affinity tag.

147. The method of embodiment 146, wherein the affinity tag is biotin.

148. The method of any of embodiments 132-147, wherein the oligonucleotide bait is conjugated to a solid surface.

149. The method of embodiment 148, wherein the solid surface is a bead.

150. The method of embodiment 149, wherein the solid surface is a planar surface.

151. The method of any of embodiments 132-150, wherein the cfNA fragments are cell-free deoxyribonucleic acid (cfDNA) fragments.

152. The method of any of embodiments 132-150, wherein the cfNA fragments are cell-free ribonucleic acid (cfRNA) fragments.

153. The method of any of embodiments 132-152, wherein the analyzing abundance, size and sequence context of the cfNA fragments comprises calculating a transcriptional activity score (TAS).

154. The method of any of embodiments 132-152, wherein the analyzing abundance, size and sequence context of the cfNA fragments comprises performing an electrophoretic separation.

155. The method of embodiment 154, wherein the electrophoretic separation comprises gel or capillary electrophoresis.

156. The method of embodiment 155, wherein the electrophoretic separation comprises microfluidic separation of cfNA fragments.

157. The method of any of embodiments 132-156, wherein the method comprises comparing mobilities of cfNA fragments to a known standard.

158. The method of any of embodiments 132-152, wherein the analyzing abundance, size and sequence context of the cfNA fragments comprises
   i. stretching the cfNA fragments, and
   ii. acquiring an image of the cfNA fragments.

159. The method of any of embodiments 132-152, wherein the analyzing abundance, size and sequence context of the cfNA fragments comprises capturing an end of a cfNA fragment in an optical trap or flow-stretching a cfNA fragment.

160. The method of any of embodiments 132-152, wherein the analyzing abundance, size and sequence context of the cfNA fragments comprises:
   i. contacting the cfNA fragments with a dye,
   ii. separating the cfNA fragments into droplets,
   iii. flowing the droplets past a detector,
   iv. measuring the fluorescence of each cfNA fragment, and
   v. calculating a size from the fluorescence intensity;
   wherein fluorescence of the dye is enhanced by contact with the cfDNA fragments.

161. The method of any of embodiments 132-160, further comprising comparing an amount of long cfNA fragments comprising at least 230 nucleotides to an amount of short cfNA fragments comprising less than 230 nucleotides.

162. The method of embodiment 161, wherein the long cfNA fragments comprise at least 255,270, 185 or 310 nucleotides.

163. The method of embodiment 161 or embodiment 162, wherein the short cfNA fragments comprise less than 220, 205, 190, or 175 nucleotides.

164. The method of any of embodiments 161-163, wherein an increased abundance of long cfNA fragments is indicative of a medical condition.

165. The method of embodiment 164, wherein a ratio of long cfNA fragments to short cfNA fragments of at least 0.2, 0.25, 0.3, 0.35 or 0.4 is indicative of a medical condition.

166. The method of any of embodiments 132-152, wherein the analyzing abundance, size and sequence context of the cfNA fragments comprises sequencing the cfDNA fragments and performing alignment-free sequence comparison of the cfNA fragment nucleotide sequences to a reference sequence;
   wherein the genomic region comprises the reference sequence.

167. The method of embodiment 166, further comprising:
   quantifying a relative amount of cfNA fragment sequences aligning to sequences distal to an end of the oligonucleotide bait versus cfNA fragment sequences aligning to sequences distal to a second end of the oligonucleotide bait.

168. The method of any of embodiments 132-152, wherein the analyzing abundance, size and sequence context of the cfNA fragments comprises sequencing the cfNA fragments, identifying two or more subregions within the genomic region, and counting a number of cfNA fragments comprising a sequence matching each subregion.

169. The method of embodiment 168, wherein a cfNA fragment matches a subregion if:
   a) a sequence of the fragment is identical to the sequence of the subregion, or.
   b) a sequence of the fragment is assigned to the subregion via approximate string matching.

170. A method of characterizing cfNA fragments derived from at least two genomic regions comprising a first genomic region and a second genomic region, comprising:
   a) collecting a first set of cfNA fragments from a biological sample by hybridization capture with a first oligonucleotide bait comprising a sequence complementary to a sequence of the first genomic region;
   b) collecting a second set of cfNA fragments from the biological sample by hybridization capture with a second oligonucleotide bait comprising a sequence complementary to a sequence of the second genomic region; and
   c) analyzing abundance, size and sequence context of the cfNA fragments that hybridize to the at least two oligonucleotide baits.

171. The method of embodiment 170, wherein the first oligonucleotide bait enriches a population of small cfNA fragments from the composition and the second oligonucleotide bait enriches a population of long cfNA fragments from the biological sample.

172. The method of embodiment 170 or 171, further comprising collecting a third set of cfNA fragments from the biological sample by hybridization capture with a third oligonucleotide bait comprising a sequence complementary to a sequence of the first genomic region.

173. The method of embodiment 172, wherein the third oligonucleotide bait enriches a population of small cfNA fragments from the composition.

174. The method of any of embodiments 170-173, further comprising collecting a fourth set of cfNA fragments from the biological sample by hybridization capture with a fourth oligonucleotide bait comprising a sequence complementary to a sequence of the second genomic region.

175. The method of embodiment 174, wherein the fourth oligonucleotide bait enriches a population of long cfNA fragments from the biological sample.

176. The method of any of embodiments 170-175, wherein step (a) and step (b) occur simultaneously.

177. The method of any of embodiments 170-176, wherein the at least two genomic regions further comprises a third genomic region; wherein the method further comprises collecting a fifth set of cfNA fragments from the biological sample by hybridization capture with a fifth oligonucleotide bait comprising a sequence complementary to a sequence of the third genomic region.

178. The method of embodiment 177, wherein the fifth oligonucleotide bait enriches a population of short cfNA fragments from the biological sample.

179. The method of embodiment 177 or embodiment 178, wherein the collecting a fifth set of cfNA fragments from the biological sample occur simultaneously with step (a) and step (b).

180. The method of any of embodiments 170-179, further comprising collecting a sixth set of cfNA fragments from the biological sample by hybridization capture with a sixth oligonucleotide bait comprising a sequence complementary to a sequence of the third genomic region.

181. The method of embodiment 180, wherein the sixth oligonucleotide bait enriches a population of long cfNA fragments from the biological sample.

182. The method of embodiment 180 or embodiment 181, wherein the collecting a sixth set of cfNA fragments from the biological sample occur simultaneously with collecting a fifth set of cfNA fragments from the biological sample, step (a), and step (b).

183. The method of any of embodiments 170-182, wherein the analyzing abundance, size and sequence context of the cfNA fragments does not comprise identifying genomic locations or lengths of the cfNA fragments.

184. The method of any of embodiments 170-183, wherein the first oligonucleotide bait, the second oligonucleotide bait, the third oligonucleotide bait, the fourth oligonucleotide bait, the fifth oligonucleotide bait, and/or the sixth oligonucleotide bait is conjugated to an affinity tag.

185. The method of embodiment 184, wherein the affinity tag is biotin.

186. The method of any of embodiments 170-185, wherein the oligonucleotide bait is conjugated to a solid surface.

187. The method of embodiment 186, wherein the solid surface is a bead.

188. The method of embodiment 186, wherein the solid surface is a planar surface.

189. The method of any of embodiments 170-188, wherein the cfNA fragments are cell-free deoxyribonucleic acid (cfDNA) fragments.

190. The method of any of embodiments 170-189, wherein the cfNA fragments are cell-free ribonucleic acid (cfRNA) fragments.

191. The method of any of embodiments 170-190, wherein the analyzing abundance, size and sequence context of the cfNA fragments comprises calculating a transcriptional activity score (TAS).

192. The method of any of embodiments 170-191, wherein the analyzing abundance, size and sequence context of the cfNA fragments comprises performing an electrophoretic separation.

193. The method of embodiment 192, wherein the electrophoretic separation comprises gel or capillary electrophoresis.

194. The method of embodiment 193, wherein the electrophoretic separation comprises microfluidic separation of cfNA fragments.

195. The method of any of embodiments 170-194, wherein the method comprises comparing mobilities of cfNA fragments to a known standard.

196. The method of any of embodiments 170-195, wherein the analyzing abundance, size and sequence context of the cfNA fragments comprises
  i. stretching the cfNA fragments, and
  ii. acquiring an image of the cfNA fragments.

197. The method of any of embodiments 170-196, wherein the analyzing abundance, size and sequence context of the cfNA fragments comprises capturing an end of a cfNA fragment in an optical trap or flow-stretching a cfNA fragment.

198. The method of any of embodiments 170-197, wherein the analyzing abundance, size and sequence context of the cfNA fragments comprises:
  i. contacting the cfNA fragments with a dye,
  ii. separating the cfNA fragments into droplets,
  iii. flowing the droplets past a detector,
  iv. measuring the fluorescence of each cfNA fragment, and
  v. calculating a size from the fluorescence intensity;
  wherein fluorescence of the dye is enhanced by contact with the cfNA fragments.

199. The method of any of embodiments 170-198, further comprising comparing an amount of long cfNA fragments comprising at least 230 nucleotides to an amount of short cfNA fragments comprising less than 230 nucleotides.

200. The method of embodiment 199, wherein the long cfNA fragments comprise at least 255, 270, 185 or 310 nucleotides.

201. The method of embodiment 199 or embodiment 200, wherein the short cfNA fragments comprise less than 220, 205, 190, or 175 nucleotides.

202. The method of any of embodiments 199-201, wherein an increased abundance of long cfNA fragments is indicative of a medical condition.

203. The method of embodiment 202, wherein a ratio of long cfNA fragments to short cfNA fragments of at least 0.2, 0.25, 0.3, 0.35 or 0.4 is indicative of a medical condition.

204. The method of any of embodiments 170-190, wherein the analyzing abundance, size and sequence context of the cfNA fragments comprises sequencing the cfDNA fragments and performing alignment-free sequence comparison of the cfNA fragment nucleotide sequences to a reference sequence;
  wherein the genomic region comprises the reference sequence.

205. The method of embodiment 204, further comprising:
  quantifying a relative amount of cfNA fragment sequences aligning to sequences distal to an end of the oligonucleotide bait versus cfNA fragment sequences aligning to sequences distal to a second end of the oligonucleotide bait.

206. The method of any of embodiments 170-190, wherein the analyzing abundance, size and sequence context of the cfNA fragments comprises sequencing the cfNA fragments, identifying two or more subregions within the genomic region, and counting a number of cfNA fragments comprising a sequence matching each subregion.

207. The method of embodiment 206, wherein a cfNA fragment matches a subregion if:
  a) a sequence of the fragment is identical to the sequence of the subregion, or
  b) a sequence of the fragment is assigned to the subregion via approximate string matching.

208. The method of any of embodiments 132-207, wherein the composition or the biological sample comprising cfNA is plasma, serum, saliva, urine, blood components, cerebrospinal fluid, pleural fluid, amniotic fluid, peritoneal fluid, ascitic fluid, abdominopelvic washings/lavage, serous effusions, tracheobronchial or bronchoalveolar lavage.

209. The method of embodiment 208, wherein the composition or the biological sample comprising cfNA is plasma.

210. The method of any of embodiments 132-209, wherein the genomic region comprises at least one nucleotide of a promotor, a transcriptional start site, a DNase I-hypersensitive site, a Pol II pausing site, a first exon, or an intron to exon boundary.

211. The method of embodiment 210, wherein the genomic region comprises a first exon.

212. The method of embodiment 211, wherein the genomic region comprises an active transcriptional start site.

213. The method of any one of embodiments 132-212, wherein expression or post-cell death fragmentation of the genomic region is altered in a medical condition.

214. The method of any one of embodiments 132-213, wherein the genomic region comprises a start site or first exon of a steroid responsive gene.

215. The method of embodiment 214, wherein the steroid responsive gene is a glucocorticoid responsive gene, an anti-inflammatory gene, or a neutrophil activation signature gene.

216. The method of embodiment 215, wherein the glucocorticoid responsive gene is FKBP5, ECHDC3, IL1R2 or ZBTB16.

217. The method of embodiment 215, wherein the anti-inflammatory gene is DUSP1, TSC22D3, IRAK3, or CD163.

218. The method of embodiment 215, wherein the neutrophil activation signature gene is BCL2 or MCL1.

219. The method of any one of embodiments 132-218, wherein the genomic region comprises a start site or first exon of a vascular marker gene, endothelial cell marker gene, or an angiogenesis gene.

220. The method of embodiment 219, wherein the vascular marker gene is an endothelial cell marker gene, a pericyte marker gene, or an integrin gene.

221. The method of embodiment 220, wherein the endothelial cell marker gene is PECAM1, CDH5, VWF, or EPHB4.

222. The method of embodiment 220, wherein the pericyte marker gene is CSPG4, ACTA2, or DES.

223. The method of embodiment 220, wherein the integrin gene is ITGAV or ITGB3.

224. The method of embodiment 219, wherein the angiogenesis gene is a vessel destability gene, a vessel stability gene, or a notch family gene.

225. The method of embodiment 224, wherein the vessel destability gene is HIF1AN, VEGFA, PGF, FLT1, KDR, NR4A1, FGF2, FGFR1, or FGFR2.

226. The method of embodiment 224, wherein the vessel stability gene is ANGPT1, ANGPT2,TEK, PDGFB, PDGFRB, TGFB1, TGFBR1, or ENG.

227. The method of embodiment 224, wherein the notch family gene is NOTCH1, NOTCH3,DLL4, or JAG1.

228. The method of any one of embodiments 132-227, wherein the genomic region is selected from first 5 exons of EphB4 gene.

229. A method of evaluating a medical condition in a subject comprising characterizing a fragmentation pattern of cfDNA fragments derived from at least two genomic regions according to the method of any one of embodiments 132-228.

230. A method of determining origin of a cell, comprising characterizing a fragmentation pattern of cfDNA fragments derived from a genomic region according to the method of any one of claims 1-229.

231. A method of adaptive immunotherapy for the treatment of cancer in a subject comprising:
 a) administering a first course of a first immunotherapy compound to the subject;
 b) acquiring a longitudinal cell-free DNA fragmentation profile for one or more genes associated with angiogenesis and/or vasculogenesis from the subject; and
 c) administering a second course of immunotherapy to the subject;
wherein the second course of immunotherapy comprises:
 i. a second immunotherapy compound if the cell-free DNA fragmentation profile is indicative of an insufficient response to the first immunotherapy compound; or
 ii. a second course of the first immunotherapy compound if the cell-free DNA fragmentation profile is not indicative of an insufficient response to the first immunotherapy compound.

232. The method of embodiment 231, wherein the cancer is lung cancer, melanoma, gastrointestinal carcinoid tumor, colorectal cancer or pancreatic cancer.

233. The method of embodiment 231 or embodiment 232, wherein acquiring a longitudinal cell-free DNA fragmentation profile comprising acquiring a first biological sample from the subject at a T0 time-point prior to administering a first dose of the first course of the first immunotherapy compound and acquiring one or more biological samples from the subject after administering the first dose of the first course of the first immunotherapy compound.

234. The method of embodiment 233, wherein the one or more biological samples acquired after administering the first dose of the first course of the first immunotherapy compound are acquired on the same day that a dose of the of the first course of the first immunotherapy compound is administered.

235. The method of any one of embodiment s 231-234, wherein the cell-free DNA fragmentation profile comprises sizes of DNA fragments derived from enhancers, promoters, first exons or promoter-proximal transcriptional pause sites of the one or more genes associated with angiogenesis and/or vasculogenesis.

236. The method of embodiment 235, wherein an increase over time of large cell-free DNA fragments derived from enhancers, promoters, first exons or promoter-proximal transcriptional pause sites of the one or more genes associated with angiogenesis and/or vasculogenesis is indicative of an insufficient response to the first immunotherapy compound.

237. The method of any one of embodiments 231-236, wherein the first immunotherapy compound and the second immunotherapy compound are selected from the group consisting of pembrolizumab, nivolumab, atezolizumab, durvalumab, and avelumab.

tic methods.

What is claimed is:

1. A method of characterizing cell-free (cfDNA) fragments, comprising:
 (a) obtaining a set of cfDNA fragments;
 (b) identifying cfDNA fragments of said set of cfDNA fragments, wherein said cfDNA fragments of said set of cfDNA fragments:
  (i) have a length greater than about 200 bp; and
  (ii) are derived from a genomic region, wherein said genomic region comprises at least one nucleotide of a promoter, and wherein said at least one nucleotide of said promoter is not derived from a transcriptional start site; and
 (c) evaluating said cfDNA fragments against a reference sequence associated with a pathological condition.

2. The method of claim 1, wherein (b) comprises sequencing said cfDNA fragments.

3. The method of claim 2, wherein sequencing said cfDNA fragments comprises next-generation sequencing.

4. The method of claim 2, wherein sequencing said cfDNA fragments comprises nanoball sequencing.

5. The method of claim 1, wherein, in (b), said cfDNA fragments are within a droplet reaction environment.

6. The method of claim 1, wherein (b) comprises performing quantitative polymerase chain reaction (qPCR).

7. The method of claim 1, wherein (b) comprises performing real-time polymerase chain reaction (rtPCR).

8. The method of claim 1, wherein said cfDNA fragments of said set of cfDNA fragments are greater than 250 bp in length.

9. The method of claim 1, wherein said cfDNA fragments of said set of cfDNA fragments are greater than 300 bp in length.

10. The method of claim 1, wherein said cfDNA fragments of said set of cfDNA fragments are greater than 200 bp and smaller than 1000 bp in length.

11. The method of claim 1, wherein said pathological condition is an autoimmune disease.

12. The method of claim 11, wherein said autoimmune disease is rheumatoid arthritis, multiple sclerosis, or lupus.

13. The method of claim 1, wherein (c) comprises comparing mobilities of said cfDNA fragments to a known standard.

14. The method of claim 13, wherein said known standard comprises a reference library based on clinical data.

15. The method of claim 13, wherein said known standard comprises a molecular weight reference set.

16. The method of claim 1, wherein (c) comprises comparing an amount of cfDNA sequences matching a first set of reference sequences to an additional amount of cfDNA sequences matching a second set of reference sequences.

17. The method of claim 16, wherein said first set of reference sequences and second set of reference sequences represents a first fragmentation pattern and second fragmentation pattern, respectively.

18. The method of claim 17, further comprising calculating a transcriptional activity score using said first fragmentation pattern and said second fragmentation pattern.

19. The method of claim 17, wherein said first fragmentation pattern and second fragmentation pattern reflects histone-protected DNA fragments.

20. The method of claim 19, wherein said second fragmentation pattern comprises regions having one or more epigenetic states indicative of said pathological condition.

21. The method of claim 19, wherein said second fragmentation pattern comprises regions having one or more genetic states indicative of said pathological condition.

* * * * *